US006656971B2

(12) United States Patent
Wu et al.

(10) Patent No.: US 6,656,971 B2
(45) Date of Patent: Dec. 2, 2003

(54) TRISUBSTITUTED CARBOCYCLIC CYCLOPHILIN BINDING COMPOUNDS AND THEIR USE

(75) Inventors: Yong-Qian Wu, Columbia, MD (US); Sergei Belyakov, Baltimore, MD (US); Gregory S. Hamilton, Cantonsville, MD (US); David Limburg, Baltimore, MD (US); Joseph P. Steiner, Mt. Airy, MD (US); Mark Vaal, Baltimore, MD (US); Ling Wei, Lutherville, MD (US); Douglas Wilkinson, Baltimore, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 10/057,203

(22) Filed: Jan. 25, 2002

(65) Prior Publication Data

US 2002/0165275 A1 Nov. 7, 2002

Related U.S. Application Data

(60) Provisional application No. 60/263,703, filed on Jan. 25, 2001, and provisional application No. 60/291,965, filed on May 21, 2001.

(51) Int. Cl.$^7$ ...................... A61K 31/166; C07C 237/20
(52) U.S. Cl. ...................... 514/599; 514/617; 564/156; 564/74
(58) Field of Search ................... 564/149, 152, 564/155, 156, 74; 514/599, 617

(56) References Cited

U.S. PATENT DOCUMENTS

| | | |
|---|---|---|
| 2,328,490 A | 8/1943 | Pöhls |
| 2,333,552 A | 11/1943 | Pöhls et al. |
| 2,395,484 A | 2/1946 | Jennings |
| 2,593,563 A | 4/1952 | Huffman |
| 2,635,535 A | 4/1953 | Jennings |
| 2,714,613 A | 8/1955 | Huebner et al. |
| 3,673,241 A | 6/1972 | Marxer |
| 3,821,200 A | 6/1974 | Stingl |
| 3,829,463 A | 8/1974 | Kornis et al. |
| 3,829,464 A | 8/1974 | Kornis et al. |
| 3,867,426 A | 2/1975 | Olin et al. |
| 3,872,157 A | 3/1975 | Brokke et al. |
| 3,876,797 A | 4/1975 | Biel |
| 3,880,642 A | 4/1975 | Baker et al. |
| 3,937,729 A | 2/1976 | Teach |
| 3,941,581 A | 3/1976 | Teach |
| 3,962,306 A | 6/1976 | Kuhle et al. |
| 3,981,914 A | 9/1976 | Mutsch et al. |
| 4,028,093 A | 6/1977 | Teach |
| 4,031,127 A | 6/1977 | Leone et al. |
| 4,041,070 A | 8/1977 | Asato et al. |
| 4,044,147 A | 8/1977 | Nelson |
| 4,072,711 A | 2/1978 | Asato et al. |
| 4,111,682 A | 9/1978 | Gutman |
| 4,225,708 A | 9/1980 | Kanbe et al. |
| 4,238,503 A | 12/1980 | Teach et al. |
| 4,245,037 A | 1/1981 | Tsujino et al. |
| 4,255,511 A | 3/1981 | Hirano et al. |
| 4,266,013 A | 5/1981 | Adachi et al. |
| 4,282,369 A | 8/1981 | Schirmer |
| 4,328,165 A | 5/1982 | Schirmer |
| 4,328,367 A | 5/1982 | Nagase |
| 4,373,017 A | 2/1983 | Masukawa et al. |
| 4,384,996 A | 5/1983 | Bollinger |
| 4,387,106 A | 6/1983 | De Vries et al. |
| 4,405,644 A | 9/1983 | Kabbe et al. |
| 4,410,697 A | 10/1983 | Tör ök et al. |
| 4,426,222 A | 1/1984 | Boroschewski et al. |
| 4,435,567 A | 3/1984 | Lugosi et al. |
| 4,473,579 A | 9/1984 | Devries |
| 4,536,341 A | 8/1985 | Rigterink et al. |

(List continued on next page.)

FOREIGN PATENT DOCUMENTS

| | | |
|---|---|---|
| CH | 459172 | 9/1968 |
| EP | 0053029A A1 | 6/1982 |
| EP | 0633145A B1 | 1/1995 |
| WO | WO8806451 A1 | 9/1988 |
| WO | WO9204370 A1 | 3/1992 |
| WO | WO9219254 A1 | 11/1992 |
| WO | WO9640633 A1 | 12/1996 |
| WO | WO9718828 A1 | 5/1997 |
| WO | WO9736869 A1 | 10/1997 |
| WO | WO9825950 A1 | 6/1998 |
| WO | WO9837882 A1 | 9/1998 |
| WO | WO9845259 A2 | 10/1998 |
| WO | WO9845259 A3 | 10/1998 |
| WO | WO99003571 A1 | 1/1999 |
| WO | WO 99/15164 | 4/1999 |
| WO | WO9959959 A1 | 11/1999 |
| WO | WO9962511 A1 | 12/1999 |
| WO | WO0117953 A1 | 3/2001 |
| WO | WO0248178 A3 | 6/2002 |
| WO | WO0248178 A2 | 6/2002 |
| WO | WO02059080 A3 | 8/2002 |

OTHER PUBLICATIONS

Agafonov, et al., Chemical Abstracts V. 109 #15 (1988).
Baetge, E. Edward, et al., "Neurite Outgrowth in PC12 Cells Deficient in CAP–43", Neuron, vol. 6 21–30, Jan. 1991.
Barinaga, M., "Neurotrophic Factors Enter The Clinic", Science 264: 722–744.

(List continued on next page.)

Primary Examiner—Alan L. Rotman
Assistant Examiner—Rita Desai
(74) Attorney, Agent, or Firm—Hansjorg Sauer

(57) ABSTRACT

The present invention relates to novel, non-peptidic small organic compounds having an affinity for cyclophilin (CyP)-type immunophilin proteins, and to pharmaceutical compositions comprising one or more of the said compounds. The invention further relates to the uses of these compounds and compositions for binding CyP-type proteins, inhibiting their peptidyl-prolyl isomerase activity, and for research, development, and therapeutic applications in a variety of medical disorders.

7 Claims, No Drawings

U.S. PATENT DOCUMENTS

| | | | |
|---|---|---|---|
| 4,554,654 | A | 11/1985 | Kato |
| 4,608,082 | A | 8/1986 | Craig et al. |
| 4,623,662 | A | 11/1986 | De Vries |
| 4,629,739 | A | 12/1986 | Davey et al. |
| 4,681,871 | A | 7/1987 | Teschemacher |
| 4,703,033 | A | 10/1987 | Seebach |
| 4,711,905 | A | 12/1987 | Sirrenberg et al. |
| 4,764,503 | A | 8/1988 | Wenger |
| 4,820,871 | A | 4/1989 | Kissener et al. |
| 4,855,478 | A | 8/1989 | Woolard |
| 4,868,210 | A | 9/1989 | Trivedi |
| 4,885,276 | A | 12/1989 | Witzel |
| 4,914,188 | A | 4/1990 | Dumont |
| 4,957,903 | A | 9/1990 | Ranby |
| 4,959,500 | A | 9/1990 | Schleifstein |
| 5,003,106 | A | 3/1991 | De Vries |
| 5,015,644 | A | 5/1991 | Roth et al. |
| 5,015,762 | A | 5/1991 | Schirmer et al. |
| 5,019,646 | A | 5/1991 | Furcht |
| 5,023,077 | A | 6/1991 | Gevas |
| 5,030,653 | A | 7/1991 | Trivedi |
| 5,057,610 | A | 10/1991 | Pastor |
| 5,059,614 | A | 10/1991 | Lepage |
| 5,091,571 | A | 2/1992 | Lee et al. |
| 5,099,059 | A | 3/1992 | Baker |
| 5,100,899 | A | 3/1992 | Calne |
| 5,116,816 | A | 5/1992 | Dreyfuss |
| 5,122,511 | A | 6/1992 | Patchett |
| 5,130,481 | A | 7/1992 | Khanna et al. |
| 5,134,121 | A | 7/1992 | Mobley |
| 5,166,429 | A | 11/1992 | Ito et al. |
| 5,187,270 | A | 2/1993 | Bernatowicz |
| 5,198,582 | A | 3/1993 | Oh et al. |
| 5,250,701 | A | 10/1993 | Abraham et al. |
| 5,250,717 | A | 10/1993 | Knapp |
| 5,273,989 | A | 12/1993 | Schwab |
| 5,276,182 | A | 1/1994 | Cardin et al. |
| 5,283,362 | A | 2/1994 | Hackl et al. |
| 5,284,826 | A | 2/1994 | Eberle |
| 5,288,914 | A | 2/1994 | Kirchhoff |
| 5,302,742 | A | 4/1994 | Landscheidt et al. |
| 5,315,011 | A | 5/1994 | Benicewicz et al. |
| 5,321,009 | A | 6/1994 | Baeder et al. |
| 5,326,856 | A | 7/1994 | Coughlin et al. |
| 5,330,993 | A | 7/1994 | Armistead et al. |
| 5,331,004 | A | 7/1994 | Denny et al. |
| 5,384,425 | A | 1/1995 | Ito et al. |
| 5,414,118 | A | 5/1995 | Yosizato et al. |
| 5,432,191 | A | 7/1995 | Abraham et al. |
| 5,449,612 | A | 9/1995 | Lepargneur et al. |
| 5,449,661 | A | 9/1995 | Nakamura et al. |
| 5,451,677 | A | 9/1995 | Fisher et al. |
| 5,462,927 | A | 10/1995 | Mureau et al. |
| 5,464,820 | A | 11/1995 | Burton et al. |
| 5,478,810 | A | 12/1995 | Stuber et al. |
| 5,545,719 | A | 8/1996 | Shashoua |
| 5,559,150 | A | 9/1996 | Soll |
| 5,567,831 | A | 10/1996 | Li |
| 5,576,335 | A | 11/1996 | Sueda et al. |
| 5,585,518 | A | 12/1996 | Marschner et al. |
| 5,612,378 | A | 3/1997 | Tianbao et al. |
| 5,614,547 | A | 3/1997 | Hamilton et al. |
| 5,614,550 | A | 3/1997 | Yoshida et al. |
| 5,621,010 | A | 4/1997 | Sueda et al. |
| 5,622,970 | A | 4/1997 | Armistead et al. |
| 5,624,894 | A | 4/1997 | Boder |
| 5,624,937 | A | 4/1997 | Reel et al. |
| 5,661,182 | A | 8/1997 | Abraham et al. |
| 5,696,135 | A | 12/1997 | Steiner et al. |
| 5,719,320 | A | 2/1998 | Jinbo |
| 5,721,256 | A | 2/1998 | Hamilton et al. |
| 5,723,075 | A | 3/1998 | Hayasaka et al. |
| 5,728,659 | A | 3/1998 | Naka et al. |
| 5,741,819 | A | 4/1998 | Illig et al. |
| 5,780,484 | A | 7/1998 | Zelle et al. |
| 5,786,378 | A | 7/1998 | Hamilton et al. |
| 5,795,908 | A | 8/1998 | Hamilton et al. |
| 5,798,355 | A | 8/1998 | Steiner et al. |
| 5,801,187 | A | 9/1998 | Li et al. |
| 5,801,197 | A | 9/1998 | Steiner |
| 5,811,434 | A | 9/1998 | Zelle |
| 5,840,305 | A | 11/1998 | Bukrinsky |
| 5,843,906 | A | 12/1998 | Chandrakumar |
| 5,843,960 | A | 12/1998 | Steiner |
| 5,846,979 | A | 12/1998 | Hamilton |
| 5,846,981 | A | 12/1998 | Steiner |
| 5,849,732 | A | 12/1998 | Suzuki et al. |
| 5,858,327 | A | 1/1999 | Pollak et al. |
| 5,859,031 | A | 1/1999 | Hamilton |
| 5,874,449 | A | 2/1999 | Hamilton |
| 5,898,029 | A | 4/1999 | Lyons |
| 5,945,450 | A * | 8/1999 | Takenouchi et al. ........ 514/381 |
| 5,972,924 | A | 10/1999 | Keep |
| 5,986,044 | A | 11/1999 | Cardin et al. |
| 5,994,398 | A | 11/1999 | John et al. |
| 6,005,008 | A | 12/1999 | Widdowson et al. |
| 6,028,223 | A | 2/2000 | Ruminski et al. |
| 6,030,991 | A | 2/2000 | Chan |
| 6,043,284 | A | 3/2000 | Arrowsmith et al. |
| 6,054,452 | A | 4/2000 | Hamilton et al. |
| 6,054,457 | A | 4/2000 | Setoi et al. |
| 6,080,753 | A | 6/2000 | Lyons |
| 6,083,986 | A | 7/2000 | Castle et al. |
| 6,093,742 | A | 7/2000 | Salituro et al. |
| 6,121,323 | A | 9/2000 | Merrill |
| 6,133,319 | A | 10/2000 | Widdowson |
| 6,444,643 | B1 | 9/2002 | Steiner |
| 2002/0137605 | A1 | 9/2002 | Hamilton |
| 2003/0005509 | A1 | 1/2003 | Steiner |

OTHER PUBLICATIONS

Basi, Guriqbal S., et al., "Primary Structure and Transcriptional Regulation of GAP–43, a Protein Associated with Nerve Growth", Cell, vol. 49, 785–791, Jun. 19, 1987.

Beck, Klaus D., "Mesencephalic Dopaminergic Neurons Protected by GDNF from Axotomy–Induced Degeneration in the Adult Brain", Nature, 373 (1995) 339–41.

Benowitz, Larry I., et al., "A Membrane Phosphoprotein Associated with Neural Development, Axonal Regeneration, Phospholipid Metabolism, and Synaptic Plasticity", TINS, vol. 10, No. 12, 1987.

Bierer, Barbara E., "Two Distinct Transmission Pathways in T Lymphocytes are Inhibited by Complexes Formed Between an Immunophilin and Either FK506 or Rapamycin", Proc. Natl. Acad. Sci. USA, vol. 87, pp. 9231–9235, Dec. 1990.

Bisby, M.A., "Dependence of GAP43 (B50, F1) Transport on Axonal Regeneration in Rat Dorsal Root Ganglion Neurons", Brain Research, 458 (1988) 157–161.

Bixby, John L., "Protein Kinase C is Involved in Laminin Stimulation of Neurite Outgrowth", Neuron 3(3):287–97 (1989).

Braun, W., "Three–Dimensional Structure and Actions of Immunosuppressants and Their Immunophilins", The FASEB Journal, vol. 9, Jan. 1995.

Bredt, Davis S., "Nitric Oxide Snthase Regulatory Sites", J. Biol. Chem. 267(16) 10976–81 (1992).

Burkhard, P. et al., "The Discovery of Steroids and Other Novel FKBP Inhibitors Using a Molecular Docking Program", J. Mol. Biol. (1999) 287, 853–858.

Calvo, Victor, et al., "Interleukin 2 Stimulation of p70 S6 Kinase Activity is Inhibited by te Immunosuppressant Rapamycin", Proc. Natl. Acad. Sci. USA, vol. 89, pp. 7571–7575, Aug. 1992.

Chan, et al., Chemical Abstracts vol. 126, 47207 (1996).

Chandrakumar, et al., Chemical Abstracts vol. 130, 25348 (1998).

Chong, M.S., et al., "GAP–43 mRNA in Rat Spinal Cord and Dorsal Root Ganglia Neurons: Development Changes and Re–expression Following Peripheral Nerve Injury", European Journal of Neuroscience, vol. 4, pp. 83–895, 1992.

Christner, Claudia, et al., "Synthesis and Cytotoxic Evaluation of Cycloheximide Derivatives as Potential Inhibitors of FKBP 12 with Neuroregenerative Properties", J. Med. Chem., 1999, 42, 3615–3622.

Chung, Jongkyeong, et al., "Rapamy cin–FKBP Specifically Blocks Growth–dependent Activation of and Signaling by the 70 kd S6 Protein Kinases", *Cell,* vol. 69, 1227–1236, Jun. 26 1992.

Comanita, et al., Chemical Abstracts V. 82, #21 (1975).

Connolly, M.A., et al., "GPI 1046 Elicits Neurite Outgrowth of Primary Sensory Neuronal Cultures", Society of Neuroscience, Abstract 677.13, vol. 23, 1997.

Costantini, Lauren C., et al., "A Novel Immunophilin Ligand: Distinct Branching Effects on Dopaminergic Nurons in Culture and Neurotrophic Actions after Oral Administration in an Animal Model of Parkinson's Disease", Neurobiology of Disease, 5(1998) 97–106.

Costantini, Lauren C., et al., "Immunophilin Ligands Can Prevent Progressive Dopaminergic Degeneration in Animal Models of Parkinson's Disease", European Journal of Neuroscience, 13 (2001) 1085–92.

Costantini, L.C., "Neuroprotective and Regenerative Effects of Immunophilin Ligands in an Animal Model of Parkinsons's Disease", Society for Neuroscience, vol. 23, 1997.

Dawson, Ted M., et al., "Immunosuppressant FK506 Enhances Phosphorylation of Nitric Oxide Synthase and Protects Against Glutamate Neurotoxicity", Proc. Natl. Acad. Sci. USA, vol. 90, pp. 9808–9812, Nov. 1993.

Dawson, Valina L., et al., "Mechanisms of Nitric Oxide—Mediated Neurotoxicity in Primary Brain Cultures", The Journal of Neuroscience, Jun. 1993, 13(6): 2651–2661.

Dawson, Valina L., et al., "Mitric Oxide Mediates Glutamate Neurotoxicity in Primary Cortical Cultures,", Proc. Natl. Acad. Sci. USA. vol. 88, pp. 6368–6371, Jul. 1991.

DeFranco, Anthony L., "Immunosuppressants at Work", Nature, vol. 352, 754–55, Aug. 29, 1991.

Desjarlais, et al., Chemical Abstracts vol. 74, 53338 (1971).

Dragovich, P.S., et al., "Structure–Based Design of Novel, Urea–Containing FKBP12 Inhibitors, Book of Abstracts", 211th American Chemical Society National Meeting.

Dumont, Francis, J., et al., "Distinct Mechanisms of Suppression of Murine T Cell Activation by the Related Macrolides FK–506 and Rapamycin", The Journal of Immunology, vol. 144, 251–258, No. 1, Jan. 1, 1990.

Dumont, Francis, J., et al., "The Immunosuppressive and Toxic Effects of FK–506 are Mechanistically Related: Pharmacology of a Novel Antagonist of FK–506 and Rapamycin", J. Exp. Med., 1992, 176, 751–760.

Dumont, Francis J., et al., "The Immunosuppressive Macrolides FK–506 and Rapamycin Act as Reciprocal Antagonists in Murine T Cells", The Journal of Immunology, vol. 144, 1418–1424, No. 4. Feb. 15, 1990.

Felix, et al., Chemical Abstracts vol. 93, 204202 (1980).

Ferrari, Stefano, et al., "The Immunosuppressant Rapamycin Induces Inactivation of p70s6k through Dephosphorylation of a Novel Set of Sites", The Journal of Biological Chemistry, vol. 268, No. 22, pp. 16091–16094, Aug. 5, 1993.

Fruman, David A., et al., "Calcineurin phosphatase activity in T lymphocytes is inhibited by FK506 and cyclosporin A", Proc. Natl. Acad. Sci. USA. 89 (1992) 3686–3690.

Fujita, Ko, et al., "Regulation of the Differentiation of PC12 Pheochromocytoma Cells", Environmental Health Perspectives, vol. 80, pp. 127–142, 1989.

Galta, Andrzej, et al., "A Rapamycin–Selective 25–kDa Immunophilin", Biochemistry, vol. 31, No. 8, 1992.

Galat, Andrzej, "Peptidylproline cis–trans–isomerases: Immunophilins", Eur. J. Biochem. 216, 689–707 (1993).

Gash, Don M., et al., "Functional recovery in parkinsonian monkeys treated with GDNF", Nature, 380 (1996) 252–255.

Gerlach, M., et al., "MPTP Mechanisms of Neurotoxicity and their Implications for Parkinson's Disease", European Journal of Pharmacology—Molecular Pharmacology Section, 208 (1991) 273–286.

Girard, Peggy R., et al., "Protein Kinase C and Its 80–Kilodalton Substrate Protein in Neuroblastoma Cell Neurite Outgrowth", Journal of Neurochemistry, vol. 54, No. 1, 300–306, 1990.

Gold, B.G., et al., "A Nonimmunosuppressant FKBP–12 Ligand Increases Nerve Regeneration", Experimental Neurology 147, 269–278 (1997).

Gold, B.G., et al., "FKBP Ligands Speed Functional Recovery and Nerve Regeneration in the Rat Sciatic Nerve Following Oral Administration", Society for Neuroscience, vol. 23, 1997.

Gold, Bruce G., "FK506 and the Role of the Immunophilin FKBP–52 in Nerve Regeneration", Drug Metabolism Reviews, 31(3), 649–663 (1999).

Gold, Bruce G., et al., "The Immunosuppressant FK506 Increases Functional Recovery and Nerve Regeneration Following Peripheral Nerve Injury", Restorative Neurology and Neuroscience, 6 (1994) 287–296.

Grabowski, et al., Chemical Abstracts V. 127 #17 (1997).

Grafstein, Bernice, et al., "Intracellular Transport in Neurons", Physiological Reviews, vol. 60, No. 4, 1167–1283, Oct. 1980.

Greene, Lloyd A., et al., "Establishment of a Noradrenergic Clonal Line of Rat Adrenal Pheochromocytoma Cells Which Respond to Nerve Growth Factor", Proc. Natl. Acad. Sci. USA, vol. 73, No. 7, pp. 2424–2428, Jul. 1976.

Guo, H., et al., "The Novel Small Molecule Immunophilin Ligand PI 1046 Stimulates Cholinergic Reinnervation of Deafferented Hippocampal Regions After Fimbria–Fornex Transection", Society for Neuroscience, Abstract 677.12, vol. 23, 1997.

Hamilton, G.S., et al., "FKBP12–Binding Domain Analogues of FK506 are Potent, Nonimmunosuppressive Neurotrophic Agents In Vitro and Promote Recovery in a Mouse Model of Parkinsons's Disease", Bioorganic & Medicinal Chemistry Letters, vol. 7, No. 13, pp. 1785–1790, 1997.

Hamilton, G.S., et al., "Immunophilins: Beyond Immunosuppression", Journal of Medicinal Chemistry, vol. 41, No. 26, Dec. 17, 1998.

Handschumacher, Robert E., et al., "Cyclophilin: A Specific Cytosolic Binding Protein for Cyclosporin A", Science, vol. 266:544–546, Nov. 1984.

Harrison, R.K., et al., "Substrate Specificities of the Peptidyl Prolyl Cis–Trans Isomerase Activities of Cyclophilin and FK–506 Binding Protein: Evidence for the Existence of a Family of Distinct Enzymes", Biochemistry, vol. 29, No. 16, Apr. 24, 1990.

Hashimoto, Seiichi, et al., "Blockage of Nerve Growth Factor Action in PC12h Cells by Staurosporine, a Potent Protein Kinase Inhibitor", Journal of Neurochemistry, vol. 53, No. 6, 1675–85, 1989.

Hicks, T.P., et al., "Alterations in the Form and Magnitude of Striatal Synaptic Plasticity in Slices from 6–OHDA–Lesioned Rats", Scoeity for Neuroscience, Abstract 677.11, vol. 23, 1997.

Hoffman, Paul N., "Expression of GAP–43, a Rapidly Transported Growth–Associated Protein, and Class II Beta Tubulin, a Slowly Transported Cytoskeletal Protein, are Coordinated in Regenerating Neurons", The Journal of Neuroscience, 893–97, Mar. 1989, 9(3).

Holt, D.A., et al., "Structure–Activity Studies of Synthetic FKBP Ligands as Peptidyl–Prolyl Isomerase Inhibitores", Bioorganic & Medicinal Chemistry Letters, vol. 4, No. 2, pp. 315–320, 1994.

Hsiang, J., et al., "The Effects of Nerve Growth Factor on the Development of Septal Cholinergic Neurons in Reaggregate Cell Cultures", Neuroscience, 29 (1989) 209–223.

Hsu, Linda, "The Effect of 12–O–Tetradecanoylphorbol–13–Acetate (TPA) on Axonal Elongation and Fasciculation", Anatomy and Embryology, 1989, 179:511–518.

Ito, Akira, et al., "The Complete Primary Structure of Calcineurin A, A Calmodulin Binding Protein Homologous with Protein Phosphatases 1 and 2A", Biochemical and Biophysical Research Communications, vol. 163, No. 3, pp. 1492–1497, 1989.

Ivery, M.T.G., et al., "Modeling the Interaction Between FK506 and FKBP12: A Mechanism for Formation of the Calcineurin Inhibitory Complex", Bioorganic & Medicinal Chemistry, vol. 5, No. 2, pp. 217–232, 1997.

Jackowski, Andre, "Neural Injury Repair: Hope for the Future as Barriers to Effective CNS Regeneration Become Clearer", British Journal of Neurosurgery (1995) 9, 303–317.

Jayaraman, Thottala, et al., "FK506 Binding Protein Associated with the Calcium Release Channel (Ryanodine Receptor)", The Journal of Biological Chemistry, vol. 267, No. 14, pp. 9474–9477, May 15, 1992.

Jin, Yong Jiu, et al., "The 25–kDa FK506–binding Protein is Localized in the Nucleus and Associates with Casein Kinae II and Nucleolin", Proc. Natl. Acad. Sci. USA, vol. 90, pp. 7769–7773, Aug. 1993.

Jin, Yong Jiu, et al., "Molecular Cloning of a Membrane––Associated Human FK506– and Rapamycin–binding Protein, FKBP–13", Proc. Natl. Acad. Sci. USA, vol. 88, pp. 6677–6681, Aug. 1991.

Jin, Yong Jiu, et al., "Molecular Cloning of a 25–kDa High Affinity Rapamycin Binding Protein, FKBP25", The Journal of Biological Chemistry, vol. 267, No. 16, pp. 10942–10945, Jun. 5, 1992.

Justice, R.M., et al., "The Detection of Proline Isomerase Activity in FK506–Binding Protein by Two–Dimensional 1H NMR Exchange Spectroscopy", Biochemical and Biophysical Research Communications, vol. 171, No. 1, 1990, pp. 445–450.

Kitamura, Yoshihisa, et al., "Suppressive Effect of FK–506, A Novel Immunosuppressant, Against MPTP–Induced Dopamine Depletion in the Striatum of Young C57BL/6 Mice", Journal of Neuroimmunology, 50 (1994) 221–224.

Klivenyl, P., et al., "Neuroprotective Effects of Creatine in a Transgenic Animal Model of Amyotrophic Lateral Sclerosis", Nature Medicine, vol. 5, No. 3, Mar. 1999.

Kofron, J.L., et al., "Determination of Kinetic Constants for Peptidyl Prolyl Cis–Trans Isomerases by an Improved Spectrophotometric Assay", Biochemistry 1991, 30, 6127–6134.

Kremlev, et al., Chemical Abstracts vol. 77, 34101 (1972).

Kuno, Takayoshi, et al., "Evidence for a Second Isoform of the Catalytic Subunit of Calmodulin–Dependent Protein Phosphatase (Calcineurin A)", Biochemical and Biophysical Research Communications. vol. 165. No. 3. pp. 1352–1358. 1989.

Kunz, Jeannette, et al., "Target of Rapamycin in Yeast, TOR2, Is an Essential Phosphatidylinositol Kinase Homology Required for G1 Progression", Cell, vol. 73, 585–596, May 7, 1993.

Kuo, Calvin J., "Rapamycin Selectively Inhibits Interleukin–2 Activation of p70 S6 Kinase", Nature, vol. 358, 70–73, Jul. 2, 1992.

Levi, A., et al., "The Mode of Action of Nerve Growth Factor in PC12 Cells", Molecular Neurobiology, vol. 2, 210–26, 1988.

LI, Linxi, et al., "Neurotrophic Agents Prevent Motoneuron Death Following Sciatic Nerve Section in the Neonatal Mouse", Journal of Neurobiology, 25, 7 (1994) 759–66.

Liang, S., et al., "Neuroimmunophilin Ligands Augment Serotonin Fiber Protection Following Lesions with Parachloroamphetamine (PCA)", Society for Neuroscience, Abstract 677.10, vol. 23, 1997.

Leiberman, A.R., "The Axon Reaction: A Review of the Principal Features of Perikaryal Responses to Axon Injury", Int. Rev. Neurobiol. 14:49–124 (1971).

Lin, Leu–Fen H., et al., "GDNF: A Glial Cell Line–Derived Neurotrophic Factor for Midbrain Dopaminergic Neurons", Science, 260 (1993) 1130–32.

Liu, J., et al., "Inhibition of T Cell Signaling by Immunophilin–Ligand Complexes Correlates with Loss of Calcineurin Phosphatase Activity", Biochemistry 1992, 31, 3896–3901.

Liu, Jun, et al., "Calcineurin is a Common Target of Cyclophilin–Cycloporin A and FKBP–FK506 Complexes", Cell, 66(4); 807–815 (1991).

Liu, Yuehueng, et al., "Dephosphorylation of Neuromodulin by Calcineurin", J. Biol. Chem. 264(22) 12800–04 (1989).

Lyons, W. Ernest, et al., "Immunosuppressant FK506 Promotes Neurite Outgrowth in Cultures of PC12 Cells and Sensory Ganglia", Proc. Natl. Acad. Sci. USA, vol. 91, pp. 3191–3195, Apr. 1994.

Magal, Ella, et al., "Effects of Ciliary Neuronotrophic Factor on Rat Spinal Cord Neurons In Vitro: Survival and Expression of Choline Acetyltransferase and Low–Affinity Nerve Growth Factor Receptors", Developmental Brain Research, 63 (1991) 141–150.

Maki, Noboru, et al., "Complementary DNA Encoding the Human T–Cell FK506–binding Protein, A Peptidylprolyl cis–trans Isomerase Distinct from Cyclophilin", Proc. Natl. Acad. Sci. USA, vol. 87, pp. 5440–5443, Jul. 1990.

Matsuoka, Ichiro, et al., "Cell–Type–specific Regulation of Nerve Growth Factor (NGF) Synthesis in Non–neuronal Cells: Comparison of Schwann Cells with Other Cell Types", The Journal of Neuroscience, Oct. 1991, 11(10):3165–3177.

Mattson, M.P., et al., "Intracellular Messengers in the Generation and Degeneration of Hippocampal Neuroarchitecture", Journal of Neuroscience Research, 21:447–464 (1988).

McKeon, Frank, "When Worlds Collide: Immunosuppressants Meet Protein Phosphatases", Cell, vol. 66, 823–826, Sep. 6, 1991.

McMahon, S.B., et al., "Peripheral Neuropathies and Neurotrophic Factors: Animal Models and Clinical Perspectives", Neurobiology 1995, 5:616–624.

Mehta, Sujata, et al., "Neurite Outgrowth and Protein Phosphorylation in Chick Embryonic Sensory Ganglia Induced by a Brief Exposure to 12–O–Tetradecanoylphorbol 13–Acetate", Journal of Neurochemistry, vol. 60, No. 3, 972–81, 1993.

Meiri, Karina F., et al., "Monoclonal Antibodies Show that Kinase C Phosphorylation of GAP–43 during Axonogenesis is Both Spatially and Temporally Restricted In Vivo", The Journal of Cell Biology, vol. 112, No. 5, 991–1005, Mar. 1991.

Morrison, Richard S., et al., "Inhibition of Protein Kinase C Activity Promotes the Neurotrophic Action of Epidermal and Basic Fibroblast Growth Factors", Brain Research, 473 (1998) 141–146.

Munroe, J.E., et al., "Aryl Alkyl Urease as Inhibitors of Influenza Virus", American Chemical Society, ed. 218, pt 1 (1999).

Navia, M.A., "Rational Design of New Immunosuppressive Drugs", Transplantation Proceedings, 31, 1097–1098 (1999).

Phelps, C.H., et al., "Commentary: Potential Use of Nerve Growth Factor to Treat Alzheimer's Disease", Neurobiology of Aging, vol. 10, pp. 205–207, 1989.

PR Newswire, Guilford Pharmaceuticals, Inc, "Guilford Pharmaceuticals Announces Completion of NIL–A Phase II Clinical Trial for Parkinson's Disease, First Clinical Evaluation of Neuroimmunophilin Ligands in Parkinson's Disease", Baltimore, Jul. 26, 2001.

Price, D.J., et al., Rapamycin–Induced Inhibition the the 70–Kilodalton S6 Protein Kinase, Science, vol. 257:973–977, Aug. 1992.

Reinhold, David, et al., "The Lack of a Role for Protein Kinase C in Neurite Extension and in the Induction of Ornithine Decarboxylase by Nerve Growth Factor in PC12 Cells", J. Biol. Chem. 264(6): 3538–44 (1989).

Rosenthal, A., et al., "Primary Structure and mRNA Localization of Protein F1, A Growth–Related Protein Kinase C Substrate Associated with Synaptic Plasticity", The EMBO Journal, vol. 6, No. 12, pp. 3641–3646, 1987.

Ross, D.T., et al., "The Novel Neuroimmunophilin Ligand GPI 1046 Stimulates Morphological Biochemical, and Behavioral Recovery in the Rat Intranigral 6–OHDA Parkinson's Disease Model", Society for Neuroscience, Abstract 677.7, vol. 23, 1997.

Ryba, M., et al., "Cyclosporine A Prevents Neurological Deterioration of Patients with SAH–A", Preliminary Report, Acta Neurochir (Wien) (1991) 112: 25–27.

Saika, Takanori, et al., "Effects of Nerve Crush and Transection on mRNA Levels for Nerve Growth Factor Receptor in the Rat Facial Motoneurons", Molecular Brain Research, 9 (1991) 157–160.

Sakaki, et al., Chemical Abstracts vol. 126, 212433 (1997).

Sauer, H., et al., "Functional and Anatomical Consequences of Chronic Treatment with Non–Immunosuppressive Immunophilin Ligands after Striatal 6–Hydroxy–Dopamine Lesions in the Rat", Society for Neuroscience, Abstract 677.8, vol. 23, 1997.

Schneider, H., et al., "Human Cyclophilin C: Primary Structure, Tissue Distribution, and Determination of Binding Specificity for Cyclosporins", Biochemistry 1994, 33, 8218–8224.

Schreiber, Stuart L., "Chemistry and Biology of the Immunophilins and Their Immunosuppressive Ligands", Science, vol. 251, 283–287, Jan. 18, 1991.

Schreiber, Stuart L., et al., "The Mechanism of Action of Cyclosporin A and FK506", Immunology Today, vol. 13, No. 4, 1992.

Schreyer, David J., et al., "Fate of GAP–43 in Ascending Spinal Axons of DRG Neurons After Peripheral Nerve Injury: Delayed Accumulation and Correlation with Regenerative Potential", The Journal of Neuroscience, Dec. 1991, 11(2), 3738–3751.

Sexton, Karen E., et al., "Thiourea Inhibitors of 15–Lipoxygenase", American Chemical Society, ed. 218, pt. 1 (1999).

Sharkey, John, et al., "Immunophilins Mediate the Neuroprotective Effects of FK506 in Focal Cerebral Ischaemia", Nature, vol. 371, 336–39, Sep. 22, 1994.

Shiga, Y., et al., "Cyclosporin A Protects Against Ischemia–Reperfusion Injury in the Brain", Brain Research, 595 (1992) 145–148.

Shoulson, Ira, "Experimental Therapeutics of Neurodegenerative Disorders: Unmet Needs", Science, vol. 282, Nov. 6, 1998.

Shrine, "NGF Receptors Can be Angels of Death", Bioworld Today, 5:1–2.

Simon, Ralph, et al., "Human CNTF and Related Cytokines: Effects on DRG Neurone Survival", Neuroreport, 7, (1995) 153–157.

Skene, J.H. Pate, et al., "Axonally Transported Proteins Associated with Axon Growth in Rabbit Central and Peripheral Nervous Systems"The Journal of Cell Biology, vol. 89, Apr. 1981, 96–103.

Skene, J.H. Pate, et al., "Changes in Axonally Transported Proteins During Axon Regeneration in Toad Retinal Ganglion Cells", The Journal of Cell Biology, vol. 89, Apr. 1981, 86–95.

Skene, J.H. Pate, "Axonal Growth–Associated Protein", Ann. Rep. Neurosci. 1989, 12:127–56.

Snipes, G.J., et al., "Regulation of Specific Neuronal and Non–Neuronal Proteins During Development and Following Injury in the Rat Central Nervous System", Progress in Brain Research, vol. 71, 155–75, F.J. Seil, E. Herbert and B.M. Carlson (Eds.).

Snyder, S.H., et al., "Immunophilins and the Nervous System", Nature Medicine, vol. 1, No. Jan. 1995.

Sommervaille, T., et al., "Time–Dependent Differences in the Increase in GAP–43, Expression in Dorsal Root Ganglion Cells After Peripheral Axomtomy", Neuroscience, vol. 45, No. 1, pp. 213–220, 1991.

Spitzfaden, C.,et al., Determination of the NMR Solution Structure of the Cyclosporin A– Cyclosporin A Complex, Journal of Biomolecular NMR, 4 (1994) 463–482.

Standaert, Robert F., et al., "Molecular Cloning and Overexpression of the Human FK–506–binding Protein FKBP", Nature, vol. 346, 671–674, Aug. 16, 1990.

Steiner, J.P., et al., Neurotrophic actions of Nonimmunosuppressive Analogues of Immunosuppressive Drugs FK506, Rapamycin and Cyclosporin A, Nature Medicine, vol. 3, No. 4.

Steiner, J.P., et al., Neurotrophic Immunophilin Ligands Stimulate Structural and Functional Recovery in Neurodegenerative Animal Models, Proc. Natl. Acad. Sci. USA, vol. 94, pp. 2019–2024, Mar. 1997 Neurobiology.

Steiner, J.P., et al., The Orally Active Neuroimmunophilin Kigand GPI–1046 promotes Structural functional Recovery in the Mouse MPTP Model of Parkinson's Disease, Society of Neuroscience, Abstract 677.6, vol. 23, 1997.

Steiner, Jospeh P., et al., "High Brain Densities of the Immunophilin FKPB colocalized with calcineurin", Nature, 584–587 vol. 358, Aug. 13, 1992.

Stichel, Christine, et al., Experimental Strategies to promote Axonal Regeneration After Traumatic Central Nervouse System Injury, Process in Neurobiology, vol. 56, pp. 119–148, 1998.

Streit, Wolfgang J., et al., "Response of Endogenous Glial Cells to Motor Neuron Degeneration Induced by Toxic Ricin", The Journal of Comparative Neurology, 268:248–263 (1988).

Swanson, Selene K.H., et al., "Cyclosporin–mediated inhibition of bovine calcineurin by cyclophilins A and B", Biochemistry, vol. 89, pp. 3741–3745, May 1992.

Tai, Ping–Kaung Ku, et al., "Association of a 59–Kilodalton Immunophilin with the Glucocorticoid Receptor Complex", Science, vol. 256, 1315–18, May 29, 1992.

Tanaka, T. et al., "Human Leukocyte Cathepsin G. Subsite Mapping with 4–Nitranilides, Chemical Modification, and Effect of Possible Cofactors", Biochem., 1985, 24, 2040–2047.

Teichner, Angela, et al., "Treatment with Cyclosporine A Promotes Axonal Regeneration in Rats Submitted to Transverse Section of the Spinal Cord", Journal fur Hirnforschung, 34 (1993) 3, 343–349.

Tetzlaff, W., et al., "Axon al Transport and Localization of B–50/GAP–43–like Immunoreactivity in Regenerating Sciatic and Facial Nerves of the Rat", The Journal of Neuroscience, Apr. 1989, 9(4), 1303–1313.

Tetzlaff, Wolfram, et al., "Response of Facial and Rubrospinal Neurons to Axotomy: Changesin mRNA Expression for Cytoskeletal Proteins and GAP–43", The Journal of Neuroscience, Aug. 1991, 11(8): 2528–2544.

Thoenen, H., et al., "Physiology of Nerve Growth Factor", Physiological Reviews, vol. 60, No. 4, 1284–1335, Oct. 1980.

Timerman, Anthony P., et al., "The Calcium Release Channel of Sarcoplasmic Reticulum is Modulated by FK–506–binding Protein", The Journal of Biological Chemistry, 268 (31): 22992–9 (1993).

Tindall, Richard S.A., "immunointervention with Cyclosporin A in Autoimmune Neurological Disorders", Journal Autoimmun., 1992 Apr., 5 Suppl. A:301–13.

Tomac, A., Et Al., "Protection and repair of the nigrostriatal dopaminergic system by GDNF in vivo", Nature, 373 (1995) 335–9.

Trupp, Miles, et al., "peripheral Expression of Biological Activities of GDNF, a New Neurotrophic Factor for Avian and Mammalian Peripheral Neurons", Journal of Cell Biology, 130 (1995) 137–148.

Tuszynski, Mark H., et al., "nerve Growth Factor Infusion in the Primate Brain Reduces Lesion–Induced Cholingergic Neuronal Degeneration", Journal of Neuroscience, 10, 11(1990) 2604–3614.

Valentine, H.L., et al., "The Neuroimmunophilin Ligand of GPI 1046 Stimulates Recovery Following Sciatic Nerve Injury", Society for Neuroscience, Abstract 677.9, vol. 23, 1997.

Van der Zee, Catharina E.E.M., et al., "Expression of Growth–Associated Protein B–50 (GAP43)in Dorsal Root Ganglia and Sciatic Nerve During Regenerative Sprouting", The Journal of Neuroscience, Oct. 1989, 9(10), 3505–3512.

Verge, V.M.K., et al., "Correlation Between GAP43 and Nerve Growth Factor Receptors in Rat Sensory Neurons", The Journal of Neuroscience, Mar. 1990, 10(3), 926–934.

Wang, G.T., et al., "Synthesis and FKBP Binding of Small Molecule Mimics of the Tricarbonyl Region of FK506", Bioorganic & Medicinal Chemistry Letters, vol. 4, No. 9, pp. 1161–1166, 1994.

Wang, M.S., et al., "Comparative Dose–Dependence Study of FK506 and Cyclosporin A on the Rate of Axonal Regeneration in the Rat Sciatic Nerve", The Journal of Pharmacology and Experimental Therapeutics, vol. 282, No. 2, 1997.

Wiese, U.H., et al., Differential Expression of Growth–Associated Protein (GAP–43) mRNA in Rat Primary Sensory Neurons After Peripheral Nerve Lesion: A Non–Radioactive In Situ Hybridisation Study:, Brain Res. 592:141–56 (1992).

Wiley, Ronald G., et al., "Suicide Transport: Destruction of Neurons by Retrograde Transport of Ricin, Abrin, and Modeccin", Science, vol. 216:889–890, May 1982.

Williams, Lawrence R., et al., "Continuous Infusion of Nerve Growth Factor Prevents Basal Forebrain Neuronal Death After Fimbria Fornix Transection", Proc. Natl. Acad. Sci., 83, (1986) 9231–9235.

Woolf, C.J., et al., "The Growth–Associated Protein GAP–43 Appears in Dorsal Root Ganglion Cells and in the Dorsal Horn of the Rat Spinal Cord Following Peripheral Nerve Injury", Neuroscience 34(2):465–78 (1990).

Wu, Yong–Qian, et al., "Synthesis and Biological Evaluation of Non–Peptidic Cyclophilin Ligands", Web Release Feb. 25, 2003, Available at: http://pubs3.acs.org/acs/journals/TOC.page?incoden=jmcmar&indecade=&involume=0&inissue=0.

* cited by examiner

TRISUBSTITUTED CARBOCYCLIC CYCLOPHILIN BINDING COMPOUNDS AND THEIR USE

A claim is hereby made for the benefit under 35 U.S.C. 119(e) of U.S. provisional application Ser. No. 60/263,703 filed Jan. 25, 2001, and of U.S. provisional application Ser. No. 60/291,965 filed May 21, 2001, both of which are incorporated herein by reference in their entirety.

The present invention relates to novel, non-peptidic small organic compounds having an affinity for cyclophilin (CyP)-type immunophilin proteins. The invention further relates to the uses of these compounds for binding CyP-type proteins, inhibiting their peptidyl-prolyl isomerase activity, and for research, development, and therapeutic applications in a variety of medical conditions.

Immunophilins are a group of proteins which are functionally characterized by their ability to bind certain immunosuppressive drugs. Two structurally and pharmacologically distinct classes of immunophilins are the FK506 binding proteins (FKBPs) and the cyclophilin (CyP) proteins. Although the prototypical members of these two protein families, FKBP12 and cyclophilin A, are both involved in the cellular mechanisms which mediate immunosuppression, they display selective affinities for very different types of immunosuppressants: members of the FKBP family bind to the macrolide antibiotics FK506 and rapamycin, whereas members of the CyP family bind to the cyclic undecapeptide Cyclosporin A (CsA).

Common to all immunosuppressant drugs is their ability to interfere with the intracellular signalling cascades of cells of the immune system. In the case of FK506 and CsA, binding of these drugs to their respective receptor proteins FKBP12 and cyclophilin A results in the cross-linking of the intracellular phosphatase calcineurin to the drug-receptor complex. The resulting inactivation of calcineurin eventually leads to the accumulation of phosphorylated calcineurin substrates, including the signaling protein NFAT (nuclear factor of activated T-cells). NFAT plays an important role in the regulation and transcriptional activation of genes involved in the T-cell activation prong of the immune response. Absent calcineurin activity, the T-cell activation cascade is interrupted because NFAT, in its phosphorylated state, cannot translocate to the cell nucleus.

Apart from its effects on the immune system, CsA has been shown to possess biological activity in the central nervous system. In rodent models of cerebral stroke, systemic treatment with CsA either before or following occlusion of the medial cerebral artery causes a reduction of infarct size [T. Yoshimoto and B. K. Siesjö, Brain Res., 839, pp. 283–91 (1999)]. CsA also protects against the decrease of acetyl choline receptors observed in the hippocampal formation after transient global forebrain ischemia [Y. Kondo et al., Neurochem Res., 24, pp. 9–13 (1999)], and has demonstrable neuroprotective effects in animal models of insulin-induced hypoglycemic coma [H. Friberg et al., J Neurosci., 18, pp. 5151–9 (1998)], traumatic brain injury [P. G. Sullivan et al., Exp Neurol., February 2000; 161, 631–7 (2000)], and experimental dopamine neuron degeneration [K. Matsuura et al., Exp. Neurol., 146, 526–351 (1997)]. In order for CsA to exert a protective effect after neural insult, it must be available at the site of injury. However, due to the blood-brain barrier, CsA shows only very limited penetration into the brain when administered systemically, and its best beneficial effects are seen if the blood-brain barrier is compromised [H. Uchino et al., Brain Res., 812, pp. 216–26 (1998); P. G. Sullivan et al., Exp. Neurol., 161, pp. 631–7 (2000)].

While the present invention is not bound by any particular theory, it appears that at least some of the effects of CsA on cells of the nervous system occur independently of calcineurin inhibition. Some of the inventors have previously shown that non-immunosuppressive peptidic analogues of CsA, which lack a calcineurin-binding domain, display neurotrophic activity in neural cell culture which is equal to that of CsA [J. P. Steiner et al., Nat. Med., 3, pp. 421–8 (1997)].

A number of types of mammalian cyclophilins have been identified and cloned, cyclophilins A, B, C, D, and cyclophilin-40 [Snyder and Sabatini, Nat. Med. 1:32–37 (1995); Friedman et al., Proc. Natl. Acad. Sci., 90:6815–6819 (1993)].

Cyclophilin B possesses an N-terminal signal sequence that directs translocation into the endoplasmic reticulum of the cell. The 23 kD cyclophilin C is found in the cytosol of the cell. Cyclophilin D, at 18 kD, appears to target its actions in the mitochondria, and cyclophilin-40 is a component of the inactivated form of a glucocorticoid receptor. Cyclophilin A is a 19 kD protein, which is abundantly expressed in a wide variety of cells. Like the other cyclophilins, cyclophilin A not only binds the immunosuppressive agent CsA, but it also possesses peptidyl-prolyl cis-trans isomerase (PPIase) and protein folding or "chaperone" activities. PPIase activity catalyzes the conversion of proline residues in a protein from the cis to the trans conformation [Fischer, et al., Biomed. Biochem. Acta 43:1101–1112 (1984)].

Since cyclophilin A was first identified as the receptor for CsA, the effects of the CsA:cyclophilin interaction have been well documented. Cyclosporin A binds to cyclophilin A with a dissociation constant in the range of $10^{-8}$ mol/L, a value representing a relatively high degree of affinity [Handschumacher et al., Science 226:544 (1984)]. Knowledge about the interaction between drug and protein spawned a number of drug discovery efforts. Initially, the focus was on identifying novel immunosuppressive drugs that would mimic the effects of CsA without displaying its dose-limiting side-effects.

The field, however, lacks appreciation of the usefulness of cyclophilin-binding compounds for treating disease states, injuries and other abnormal conditions involving the central nervous system and other parts of the body. For therapeutic application in disorders of the central nervous system, for example, cyclophilin-binding compounds would need to penetrate from the bloodstream into the brain to bind to cyclophilin and exert biological effects. Cyclosporin A, however, generally displays poor penetration into the central nervous system after systemic administration, and therefore possess only low therapeutic potential for CNS applications if the blood-brain barrier is intact. See Uchino et al.; Sullivan et al., supra. Therefore, there exists need for safe and effective compositions and methodologies for treating disease states, injuries and other abnormal conditions involving the central nervous system and other organs by use of cyclophilin-binding compounds. These needs have gone unresolved until the development of the present inventions.

Researchers have also noted a functional association of cyclophilin A with the Gag protein of the HIV virus [Thali et al., Nature 372:363–365 (1994)]. This has taken drug development approaches in a new direction (See, for example, U.S. Pat. No. 5,767,069). Many researchers now seek to develop drugs that target the interaction between cyclophilin A and Gag in order to disrupt the HIV life cycle [Sternberg, BioWorld Today 7:1 (1996)].

The focus of the present invention is on non-peptidic small molecule compounds which interact with, have an affinity for, or bind to cyclophilin proteins. By studying the binding interaction of cyclophilin A and CsA, the inventors have designed and characterized a number of novel small molecule organic compounds which interact with cyclophilins, on the basis of which the inventors were able to develop and utilize screening procedures for rapidly identifying a class of similarly active compounds. These compounds have been specifically tested to show that they effect the growth and regeneration of cells of the nervous system, and protect such cells from otherwise lethal chemical injury. The compounds can be used in a number of ways, including therapeutic and research and development applications for various medical conditions, including neurological disorders.

The invention thus provides compounds that bind to CyP proteins. The compounds of this invention preferably do not suppress the immune system and preferably do not possess a biological activity involving binding to a FKBP, i.e., the compounds inhibit the peptidyl prolyl isomerase activity of FKBP with an $IC_{50}$ of greater than 500 nM. A number of methods for determining the binding to CyPs and ways for exploiting the binding through in vitro and in vivo methods and uses are presented. Preferred compounds function to promote or affect neuronal cell growth or growth of nervous system cells, regenerate damaged or diseased neurons, or protect neurons or neuronal cells from death or degeneration following damage. Furthermore, aspects of this invention can be used in methods to identify and isolate additional CyP binding compounds or additional uses of the compounds.

The invention also provides a number of uses for these compounds, including uses that comprise the step of allowing the compound to contact an immunophilin protein. A variety of permutations of this method can be devised. In particular, the compounds can be used to affect the growth or resistance to noxious stimuli of neuronal cells, either in culture or in an animal. Thus, the compounds can be administered to cells or animals to affect a number of conditions associated with the decline, damage, or degeneration of nervous system cells or their physiological function.

In one aspect, the invention provides compounds of Formula I as shown and described below:

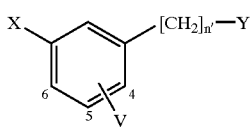

Formula I where V is attached at position 4, 5, or 6, and is selected from the group consisting of $C_1$–$C_4$ alkyloxy, $C_1$–$C_4$ alkyl, $C_2$–$C_4$ alkenyloxy which is optionally substituted with Q, $C_1$–$C_4$ alkoxycarbonyl, $C_1$–$C_6$ alkylcarbamoyl which is optionally substituted with amino or $C_1$–$C_4$ alkoxycarbonylamino; di-($C_1$–$C_4$ alkyl)carbamoyl, $C_1$–$C_4$ alkanoyl, Q-substituted $C_1$–$C_6$ alkyl, alkenyl, or alkynyl, CO—W, and —$(CH_2)_n$—W;

wherein W is Q, —Z'—$(CH_2)_m$—Q, —N=CH—$(CH_2)_m$—Q, $COOCH_3$, $COCH_3$, hydroxyl, mercaptyl, amino, nitro, halo, carboxy, trifluoromethyl, or C6 alkylamino substituted with amino or $C_1$–$C_4$ alkoxycarbonylamino;

n and m are independently 0–4;

n' is 0–3;

Z' is O, S, NH, or NR;

where X and Y are the same or different, and may independently be:

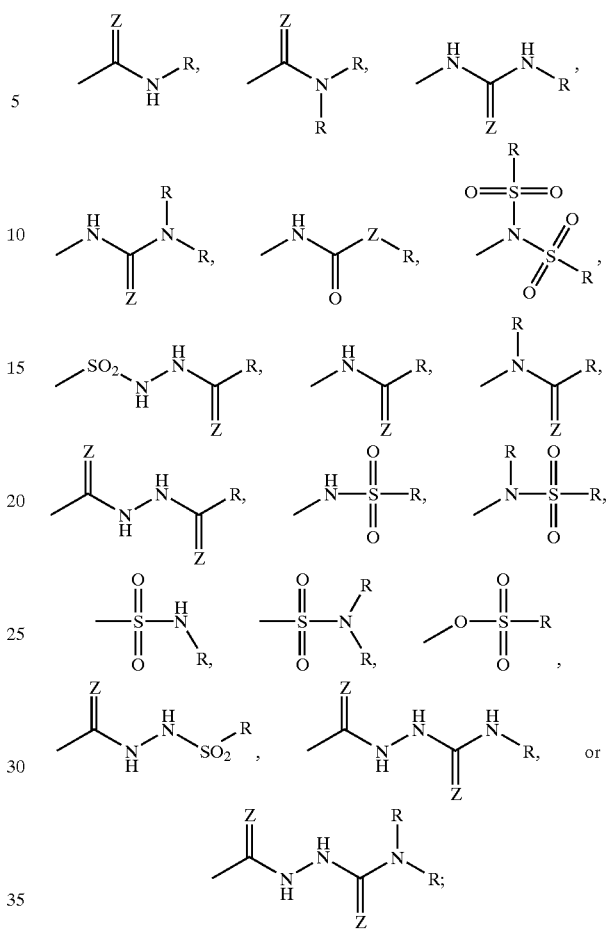

and where Y may further be: Q,

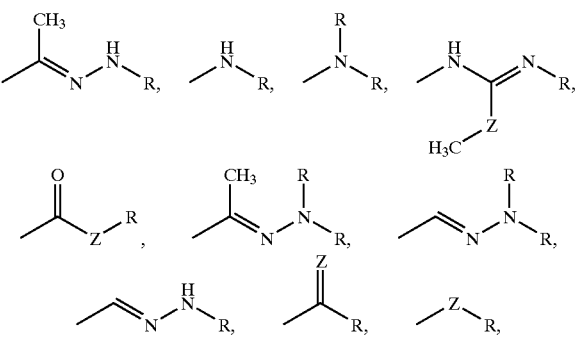

or $C_1$–$C_6$ straight or branched chain alkyl, alkenyl, or alkynyl which is substituted at one or several positions with Q, and which further is optionally substituted at one or several positions by hydroxyl, mercaptyl, or carbonyl oxygen;

wherein Z is O or S;

and wherein R may independently be:

Q, or $C_1$–$C_6$ straight or branched chain lower alkyl, alkenyl or alkynyl which is substituted at one or several positions with Q, and which further is optionally substituted in one or several positions by hydroxyl, mercaptyl, or carbonyl oxygen, and wherein one or more of the carbon atoms are optionally replaced with O, N, NH, S, SO, or $SO_2$;

and wherein Q is a mono-, bi-, or tricyclic, carbo- or heterocyclic ring which is saturated, partially saturated, or aromatic, and wherein the individual ring sizes are 5–6 members, and wherein each heterocyclic ring, if present, contains 1–4 heteroatoms independently selected from the group consisting of O, N, and S in any chemically stable order and oxidation state, and wherein Q is optionally substituted in one or several positions with:

halo; hydroxyl; mercaptyl; nitro; trifluoromethyl; aminocarbonyl; arylaminocarbonyl in which the aryl is optionally halogenated and optionally substituted with trifluoromethyl or cyano; $C_1$–$C_4$ alkylsulfonyl; $C_1$–$C_4$ alklylthio; oxo; cyano; carboxy; $C_1$–$C_6$ alkyl or alkenyl; $C_1$–$C_4$ alkoxy; $C_1$–$C_5$ alkoxycarbonyl; $C_1$–$C_4$ alkenyloxy; phenoxy; phenyl; cyanophenyl; benzyloxy; benzyl; amino; $C_1$–$C_4$ alkylamino; di-($C_1$–$C_4$) alkylamino; $C_1$–$C_4$ alkylcarbamoyl; di($C_1$–$C_4$) alkylcarbamoyl;

or a combination thereof;

provided that:

when X and Y are

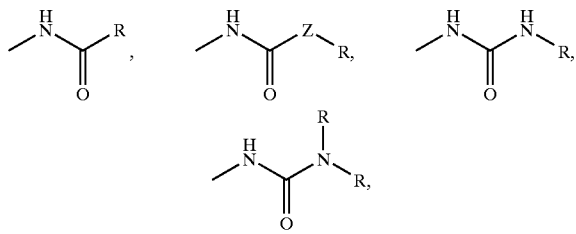

or a combination thereof, and n' is 0, and n is 0, and

V is halo, hydroxyl, nitro, trifluoromethyl, $C_1$–$C_4$ alkoxy or—alkenyloxy, phenoxy, benzyloxy, amino, or Q, then R is not Q, or $C_1$–$C_3$ branched or straight chain alkyl substituted with Q.

Preferred compounds under this aspect of the invention are substituted with V at position 5. Preferably, V is —$(CH_2)_n$—Z'—$(CH_2)_m$—Q, or Q-substituted $C_1$–$C_6$ straight or branched chain alkyl or alkenyl.

In a further group of preferred compounds n' is 0, and X and Y are independently

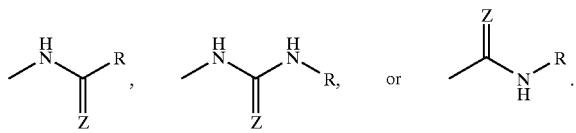

The compounds of this invention can be selected for use from Formula I. Starting with a particular compound, any of the individual variable groups R, X, Y, Z, Z', Q, V, and a value for n, n' and m can be selected while one or more of the other variable groups can be modified. For example, in Formula I, V can be attached at position 5 and specified to be —$(CH_2)_n$—NH—$(CH_2)_m$—Q to select subgroups of compounds which share a common 1,3,5,-substitution pattern wherein at least one of the Q groups is attached via an amine linkage.

Any of the subgroups thus obtained can be further divided into additional subgroups of compounds defined by the allowed combinations of X and Y, and by requiring that X and Y are either similar, or different from each other, and by requiring, for example, that R be Q, or that R be Q-substituted alkyl, alkenyl, or alkynyl, and that all Q-substituents be the same, or different from each other. This process can be repeated using any one, or a combination of, the variable groups. In this way, one skilled in the art can select and use groups of related compounds or even individual compounds, all within the invention. Many examples are shown below; however, they are merely representative of the scope of changes and modifications possible. One skilled in the art can devise many separate compounds from the description of Formula I alone.

In this specification, the generic terms "alkyl", "alkenyl" or "alkynyl" include both straight-chain and branched-chain saturated or unsaturated groups. "Aryl" in terms such as "arylaminocarbonyl" typically means groups such as phenyl, naphthyl, pyrrolyl, pyrrolidinyl, pyridinyl, pyrimidinyl, purinyl, furyl, imidazolyl, quinolinyl, oxazolyl, thiazolyl, pyrazolyl, and thienyl. "Alkyloxy" or "alkoxy" refer to groups such as, for example, methoxy or ethoxy; "alkoxycarbonyl" refers to groups such as, for example, methyl ester or butyl ester; "$C_1$–$C_6$ alkylcarbamoyl" and "di($C_1$–$C_4$)alkylcarbamoyl" refer to saturated or unsaturated carbon chains attached via an amide linkage, such as, for example, ethylcarbamoyl or diethylcarbamoyl; "$C_1$–$C_4$ alkoxycarbonylamino" refers to groups such as, for example, tert-butoxycarbonylamino ($C_4H_9$)—O—CO—NH—; "arylaminocarbonyl" refers to groups such as phenylaminocarbonyl ($C_6H_5$)—NH—CO—; "$C_1$–$C_4$ alkanoyl" refers to groups such as, for example, formyl or acetyl; "$C_6$ alkylamino" refers to groups such as, for example, hexylamino.

Compounds of Formula I may be prepared or formulated as a salt or derivative for some uses, including pharmaceutical and tissue or cell culture uses. As used herein, the CyP-binding compounds of this invention are defined to include pharmaceutically acceptable derivatives. A "pharmaceutically acceptable derivative" denotes any pharmaceutically acceptable salt, ester, thioester, or salt of such ester or thioester, of a compound of this invention or any other compound which, upon administration to an animal or human patient, is capable of providing (directly or indirectly) a compound of this invention, or a metabolite or residue thereof, characterized by the ability to bind to a CyP and/or its usefulness in treating or preventing a medical disorder. Examples of medical disorders within the scope of this aspect of the invention are given below. The compounds of the invention can also be part of a composition comprising one or more compounds of Formula I.

The compounds of the invention can be produced as a mixture of isomers or racemic mixtures or as optically pure compounds. Methods for separating stereoisomers known in the art can also be used to enrich mixtures for one or more compounds. The compositions of the invention may similarly contain mixtures of stereoisomers, mixtures of one or more stereoisomers, or be enriched for one or more stereoisomers. All of these forms are specifically included in this invention and are intended to be included in the claims.

Preferably, compounds of Formula I selectively bind to a CyP as detected, for example, by a measurable inhibition of the peptidyl-prolyl cis-trans isomerase enzyme activity (PPIase) of CyP. "Selectively bind to a CyP" means the compounds do not possess a significant binding affinity toward a FKBP and/or do not possess a biological activity associated with binding to a FKBP. For example, the $IC_{50}$ towards FKBP is at or above 500 nM. The skilled artisan is familiar with ways to detect rotamase inhibition in CyP and FKBP. In addition, a number of ways for detecting binding to a CyP are described below.

As is readily apparent from Formula I, a common substitution pattern exists, wherein at least two carbo- or heterocyclic groups are attached to a central trisubstituted phenyl ring by a combination of straight or branched linker chains. This common pattern differs from the approaches previously taken to identify other immunophilin binding compounds or drugs. For example, Holt et al. [*Bioorg. Med. Chem. Letters,* 4: 315–320 (1994)] discuss a pipecolate, or 1-(1,2-dioxo)2-carboxylate piperidine containing base structure for binding to FKBP. Similarly, earlier work by the inventors established the relevance of a 1-(1,2-dioxo)2-carboxylate pyrrolidine containing structure for binding to FKBP [Steiner et al., *Proc. Natl. Acad. Sci. U.S.A.* 94:2019–2024 (1997)]. Presumably, these structures mimic the natural substrate for the peptidyl-prolyl-isomerase (PPIase) activity, a proline-containing fragment of a protein. In a protein, the amino acid proline corresponds to a 1,2-substituted pyrrolidine structure. Prior work has generally incorporated that structure. However, Formula I does not correspond to a 1,2-substituted pyrrolidine structure. Yet, as demonstrated here, compounds of this formula possess important bioactive and biochemical functions.

The body of work related to analogues of cyclosporin A, FK-506, and rapamycin further distances the compounds of this invention from prior work. (See, for example, U.S. Pat. Nos. 5,767,069, 5,284,826, 4,703,033, and 5,122,511). These analogues typically possess a cyclic peptide structure.

In another aspect, the invention relates to methods for binding non-peptidic compounds to cyclophilin-type immunophilins. While the present invention is not bound by this theory, it is hypothesized that binding results in an "immunophilin:drug" complex, which is considered to be the active agent in the in vivo immunosuppressive and neurotrophic activities of PPIase inhibitors [Hamilton and Steiner, *J. Med. Chem.* 41:5119–5143 (1998); Gold, *Mol. Neurobiol.* 15:285–306 (1997)]. Whether or not the complex acts for any or all the therapeutic actions of these PPIase inhibitors, focusing on the immunophilin:drug interaction has led to the discovery a number of new drug compounds. Accordingly, methods of using compounds, such as those of Formula I, to create an immunophilin:compound complex, or a CyP:compound complex, provide an important aspect of this invention. This aspect can be exploited, for example, in methods where the compound, or a mixture comprising one or more of the compounds of the invention, or a pharmaceutical composition comprising one or more of the compounds of the invention, is administered to cells in culture or to an animal.

While the immunophilin:compound complex has beneficial effects in vivo and in vitro in cultured cells, numerous other uses for binding the compounds to an immunophilin exist. For example, further in vitro binding experiments can be used to identify and purify cellular components that interact with the immunophilin complex in a cell-free environment, as would be the case where an affinity chromatography column or matrix bearing the compound is reacted with a CyP, and cellular or tissue extracts containing a CyP are passed over the column or matrix.

Thus, the invention also provides methods for forming immunophilin:compound or CyP:compound complexes as well as the complexes themselves. To form these complexes, the compounds can contact an immunophilin or CyP protein in vivo, in cell or tissue culture, or in a cell-free preparation. In preferred embodiments, the compound contacts a human CyP protein, such as one or more of CyP A, B, C, D, or –40. The CyP protein can be native to the cell or organism, produced via recombinant DNA, produced by other manipulations involving introduced genetic material, or produced by synthetic means. Furthermore, chimeric proteins possessing immunophilin domains that function to bind immunophilin ligands can also be used to form a protein:compound complex. The formation of the CyP:compound, immunophilin:compound, or protein:compound complex need not be irreversible.

The binding of a compound to a CyP can be detected in a number of ways, including PPIase inhibition assay, affinity chromatography, in vivo neuroprotection or neuroregeneration activity assay, in vitro neurotrophic activity assay, or by any of the activities in neuronal cells or cells of the nervous system described below, in the examples, or in the cited references.

The invention also provides compositions comprising at least one compound of Formula I. The compositions may comprise one or more pharmaceutically acceptable carriers, excipients, or diluents. These compositions, or the compounds themselves, or mixtures of said compounds or compositions, can be administered to an animal. Administration can be one method to allow the compound to contact a CyP within the animal. As one skilled in the art would recognize, various routes of administration are possible. Exemplary routes are specifically described in the detailed description below.

The compounds of Formula I, or compositions comprising them, can function to regenerate nerve cells, promote neurite outgrowth, and protect nerves from otherwise damaging treatments or conditions. Thus, the compounds and compositions of this invention are useful in the diagnosis, cure, mitigation, treatment, or prevention of neurological conditions in animals, including humans, and in animals (including humans) exposed to neurodegenerative agents or having damaged nervous system cells. Such conditions and disorders, when present in an animal, including humans, can be neurodegenerative disorders, neuropathic disorders, neurovascular disorders, traumatic injury of the brain, spinal cord, or peripheral nervous system, demyelinating disease of the central or peripheral nervous system, metabolic or hereditary metabolic disorder of the central or peripheral nervous system, or toxin-induced- or nutritionally related disorder of the central or peripheral nervous system. When present in a human, a neurodegenerative disorder can be, for example, Parkinson's disease, Alzheimer's disease, amyotrophic lateral sclerosis (ALS), Huntington's disease, cerebellar ataxia, or multisystem atrophy including, for example, olivopontocerebellar degeneration, striatonigral degeneration, progressive supranuclear palsy, Shy-Drager syndrome, spinocerebellar degeneration and corticobasal degeneration. A demyelinating disease can be, for example, multiple sclerosis, Guillain-Barré syndrome, or chronic inflammatory demyelinating polyradiculoneuropathy. A neurovascular disorder can be global cerebral ischemia, spinal cord ischemia, ischemic stroke, cardiogenic cerebral embolism, hemorrhagic stroke, lacunar infarction, multiple infarct syndromes including multiple infarct dementia, or any disorder resulting in ischemia or ischemia/reperfusion injury of the central nervous system. Traumatic injury of the central or peripheral nervous system can be, for example, concussion, contusion, diffuse axonal injury, edema, and hematoma associated with craniocerebral or spinal trauma, or axonal or nerve sheath damage associated with laceration, compression, stretch, or avulsion of peripheral nerves or plexi, and further includes nerve damage caused during surgery, such as prostate surgery. A neuropathic disorder can be, for example, diabetic neuropathy, uremic neuropathy, neuropathy related to therapy with drugs such as phenytoin, suramin, taxol, thalidomide, vincristine or vinblastine; or neuropathy/encephalopathy associated with infectious disease, such as, for example, encephalopathy related to HIV, rubella virus, Epstein-Barr virus, herpes simplex virus, toxoplasmosis, prion infection. A metabolic disorder of the central nervous system can be, for example, status epilepticus, hypoglycemic coma, or Wilson's disease.

The following detailed description should not be taken as a limitation on the scope of the invention, and all embodiments and examples given are merely illustrative of the invention. Additional aspects of the invention can be devised by reference to this disclosure as a whole in combination with the references cited and listed throughout and at the end of the specification and the knowledge of one skilled in the art. All of the references cited and listed can be relied on, in their entirety, to allow one to make and use these additional aspects of the invention.

DETAILED DESCRIPTION OF EXEMPLARY EMBODIMENTS

One skilled in the art can refer to general reference texts for detailed descriptions of known techniques discussed herein or equivalent techniques. These texts include *Current Protocols in Molecular Biology* [Ausubel, et al., eds., John Wiley & Sons, N.Y., and supplements through June 1999), *Current Protocols in Immunology* (Coligan, et al., eds., John Wiley and Sons, N.Y., and supplements through June 1999)], and *Current Protocols in Pharmacology* (Enna et al., eds., John Wiley & Sons, N.Y., and supplements through June 1999) for example, each of which are specifically incorporated by reference in their entirety. These texts can also be referred to in making or using an aspect of the invention.

As noted above, cyclosporin A was the first compound identified to bind a CyP. Based on the cyclic structure of cyclosporin A, a number of large, usually cyclic peptides were developed as immunosuppressive compounds that bind CyP. Now, unexpectedly, the inventors have found a non-peptidic class of CyP binding compounds with activity in neuronal cells. The following compounds are representative of those tested.

Compound # 1

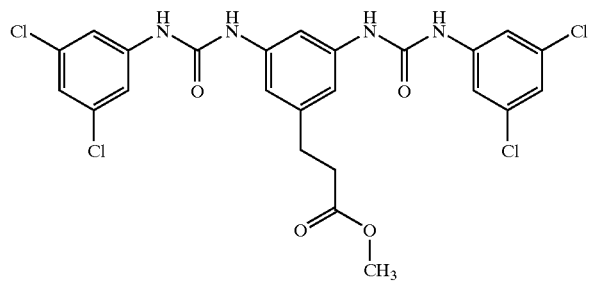

Compound # 2

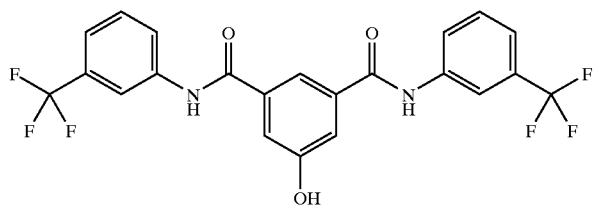

Compound # 3

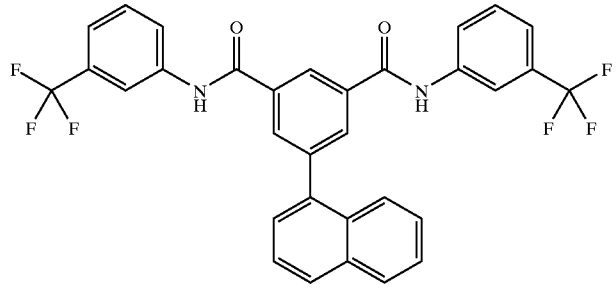

Compound # 4

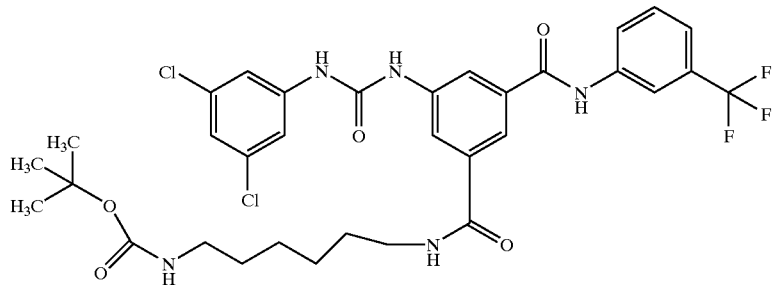

-continued
Compound # 5
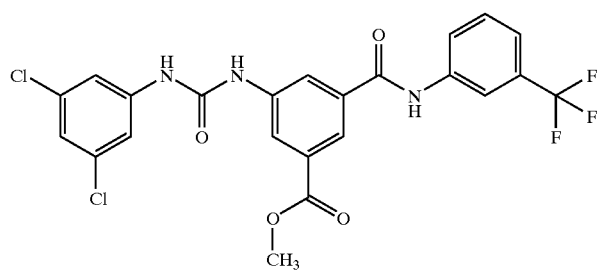
Compound # 6
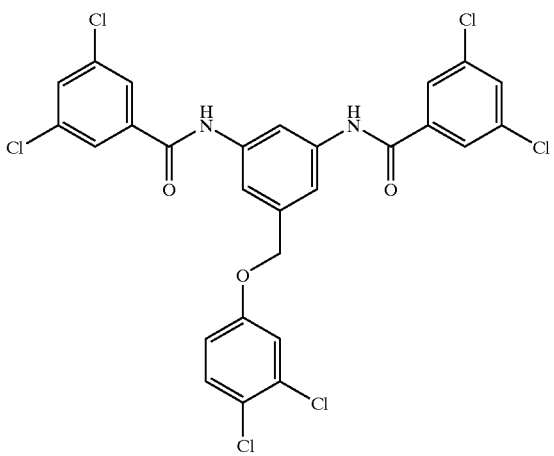
Compound # 7
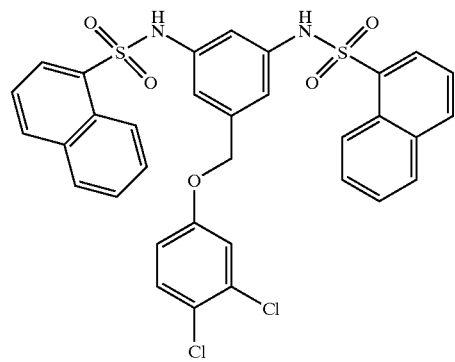
Compound # 8
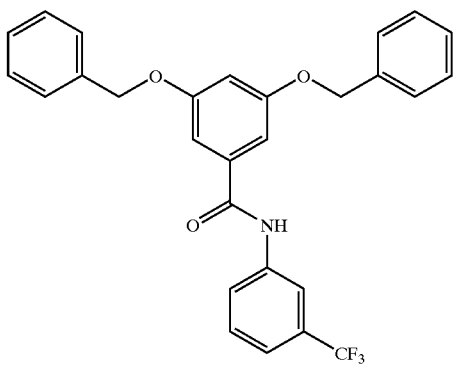
Compound # 9
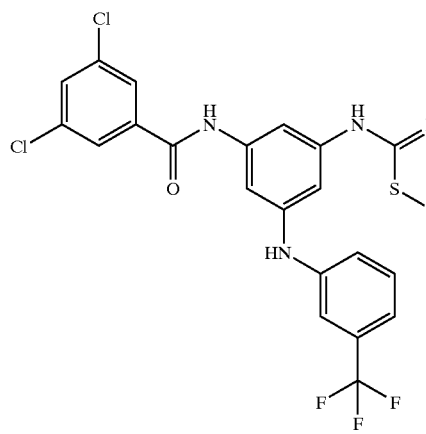
Compound # 10
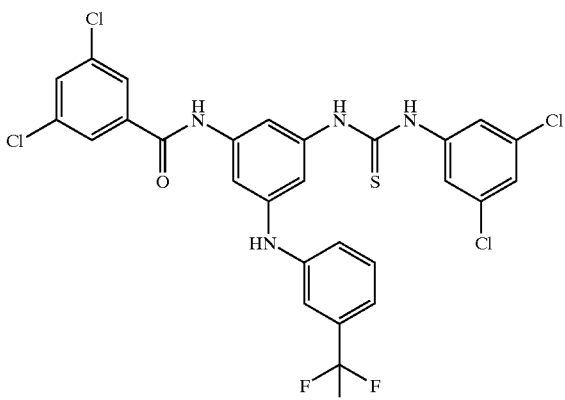
Compound # 11
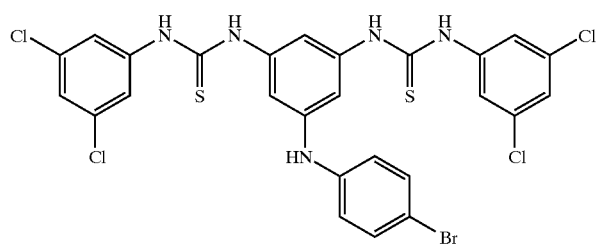
Compound # 12
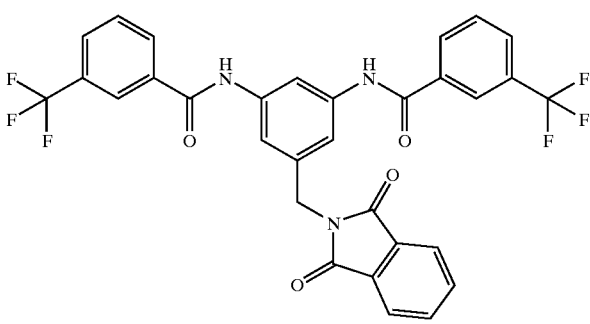

-continued
Compound # 13
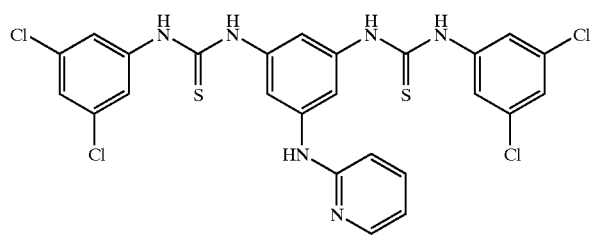
Compound # 14
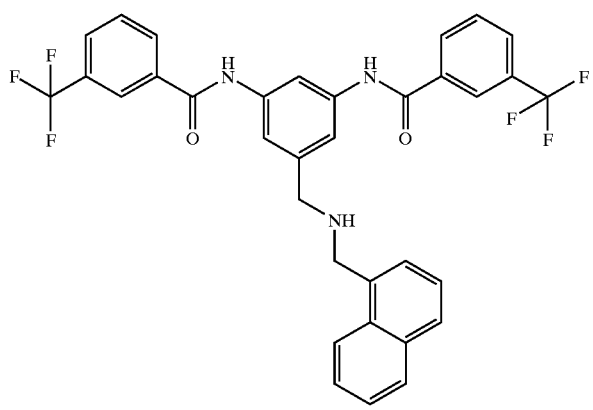
Compound # 15
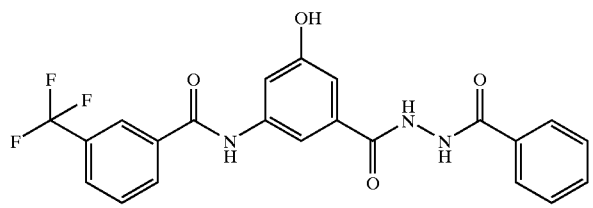
Compound # 16
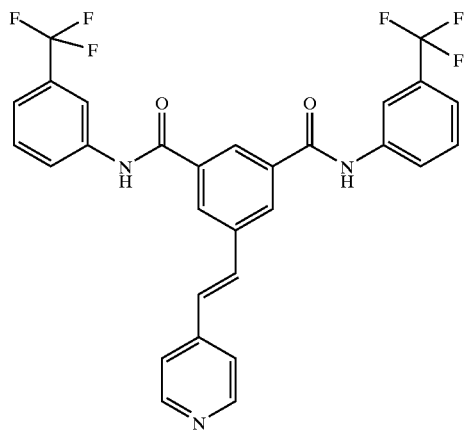
Compound # 17
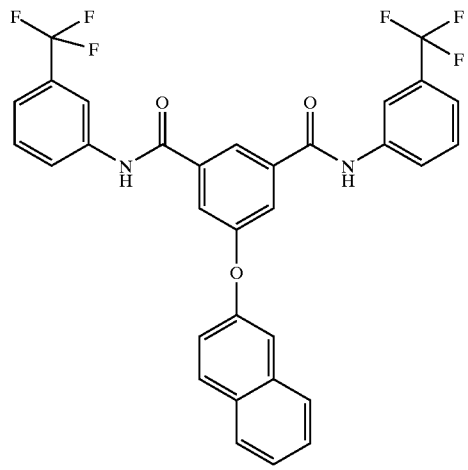
Compound # 18
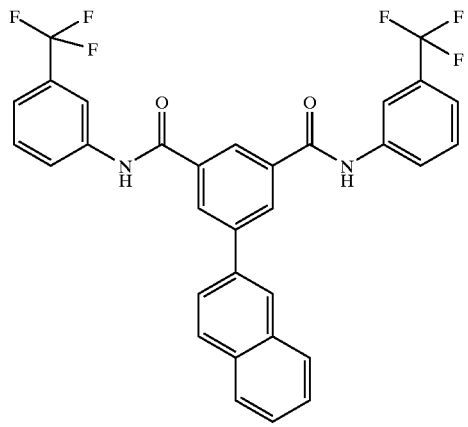

-continued
Compound # 19
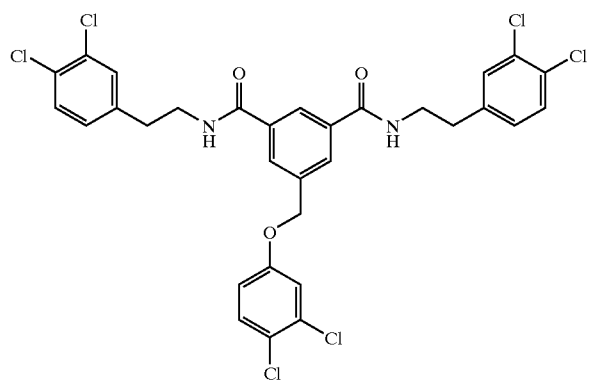
Compound # 20
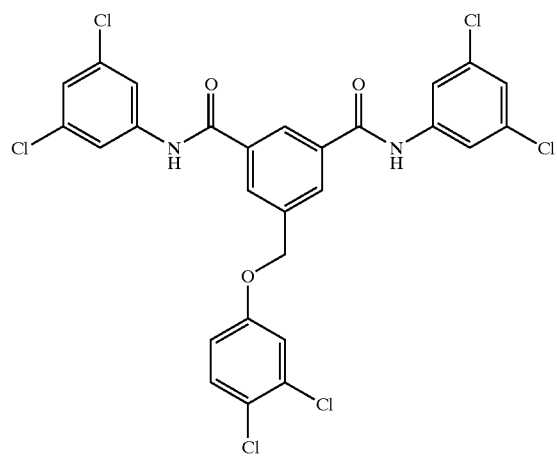
Compound # 21
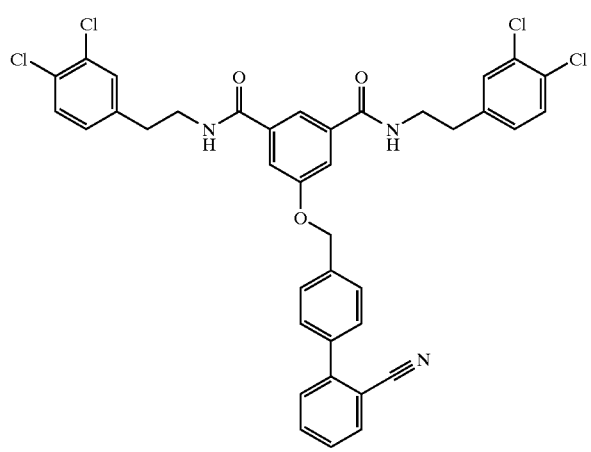
Compound # 22
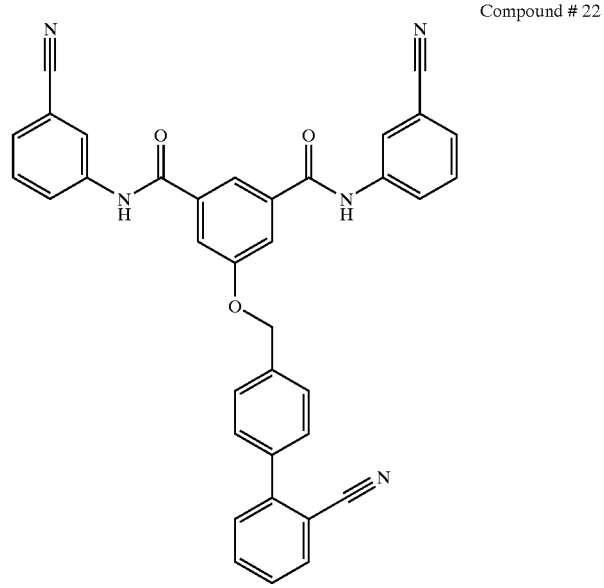
Compound # 23
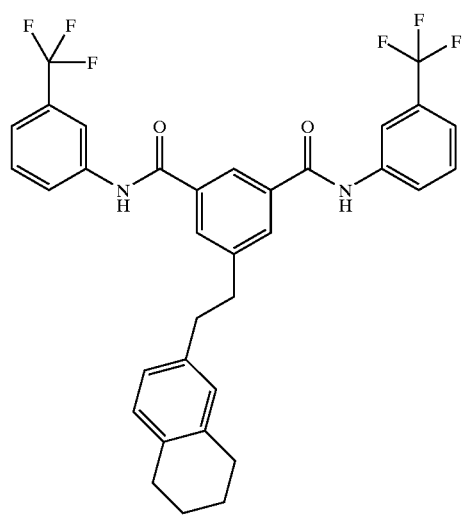
Compound # 24
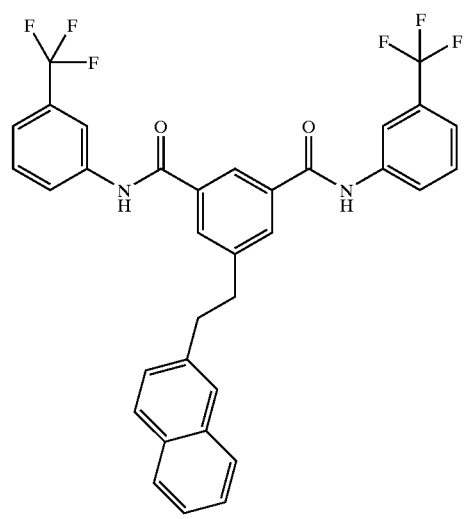

-continued
Compound # 25
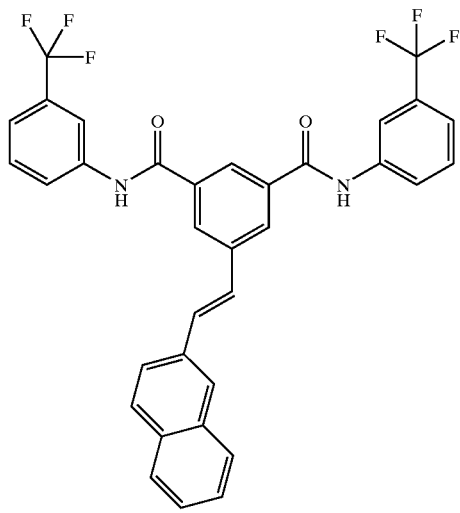
Compound # 26
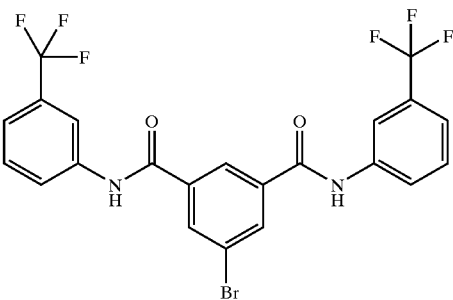
Compound # 27
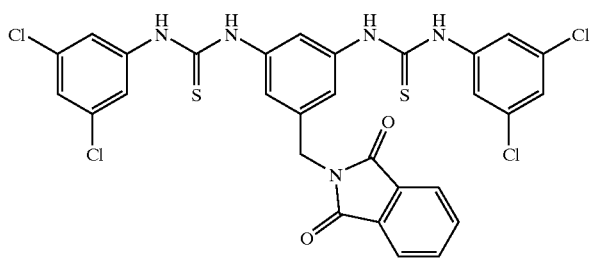
Compound # 28
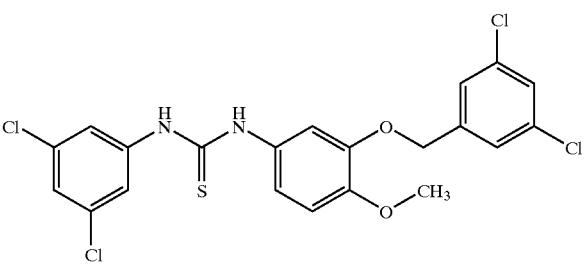
Compound # 29
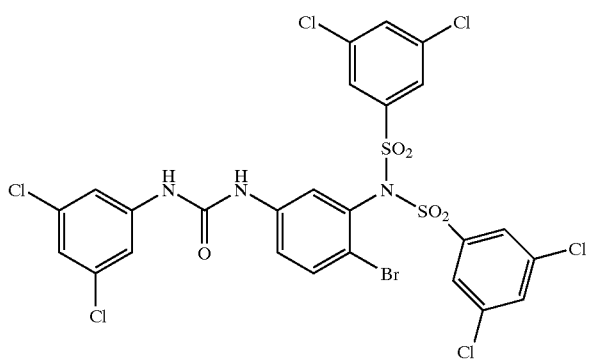
Compound # 30
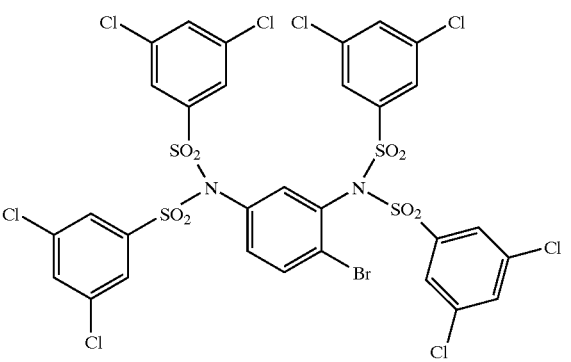
Compound # 31
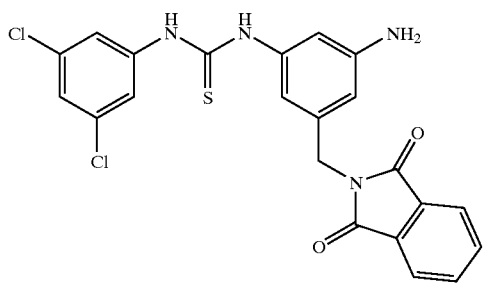
Compound # 32
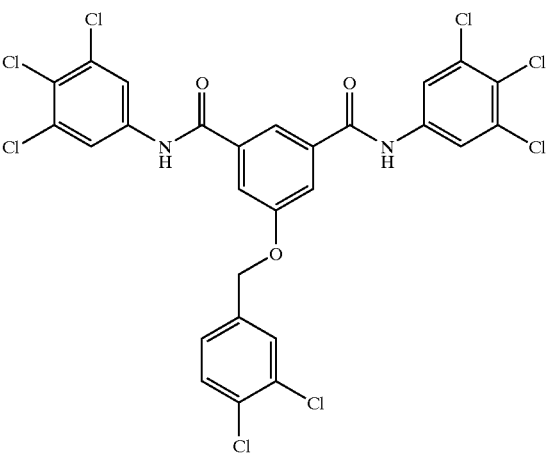

-continued
Compound # 33
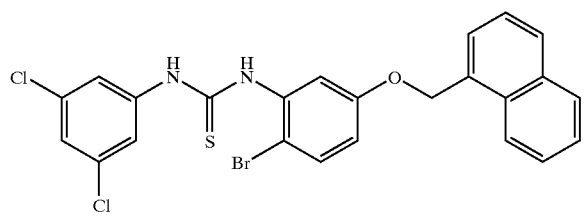
Compound # 34
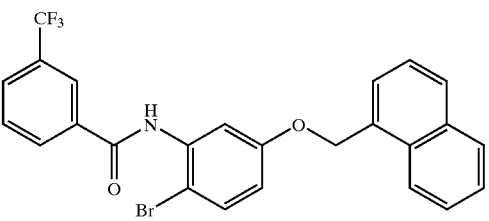
Compound # 35
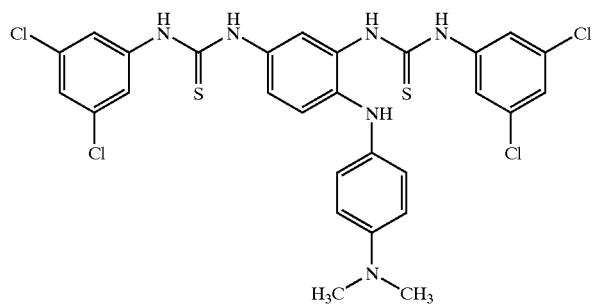
Compound # 36
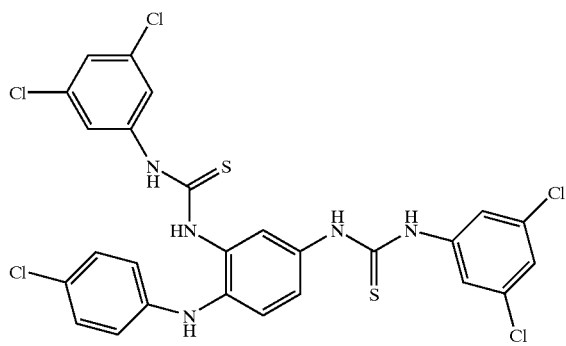
Compound # 37
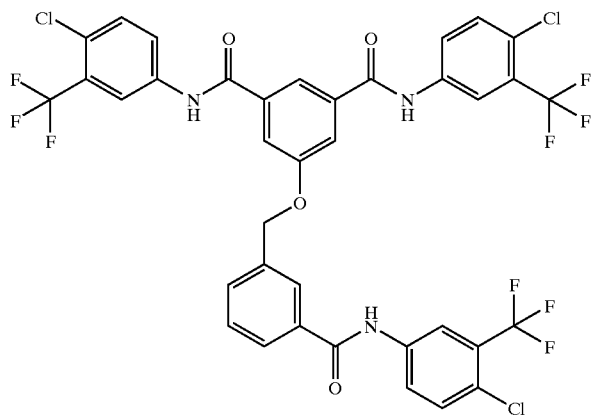
Compound # 38
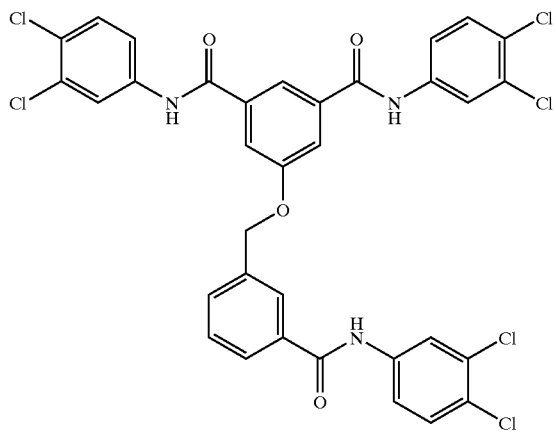
Compound # 39
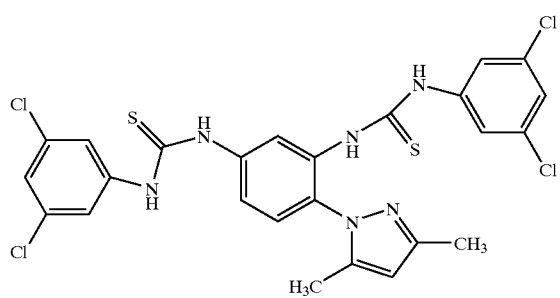
Compound # 40
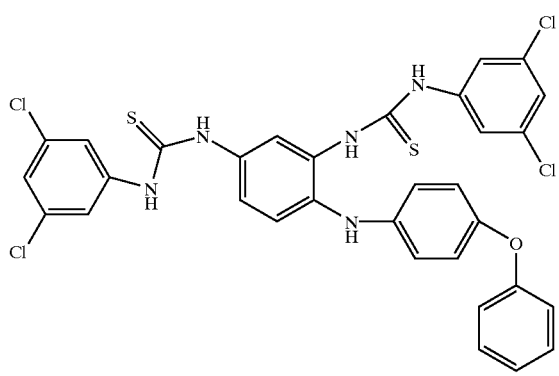

Compound # 41
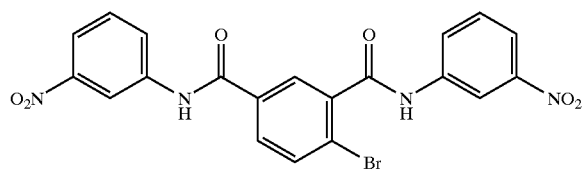
Compound # 42
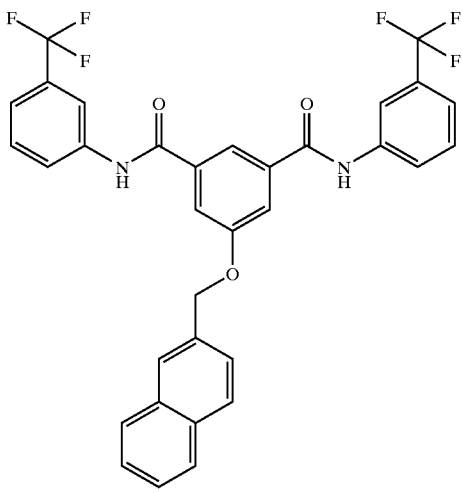
Compound # 43
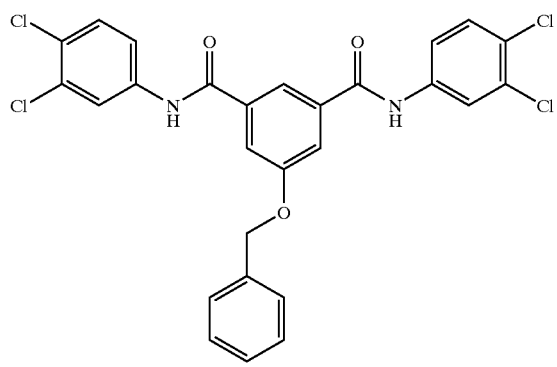
Compound # 44
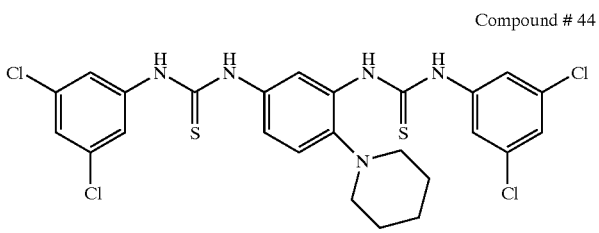
Compound # 45
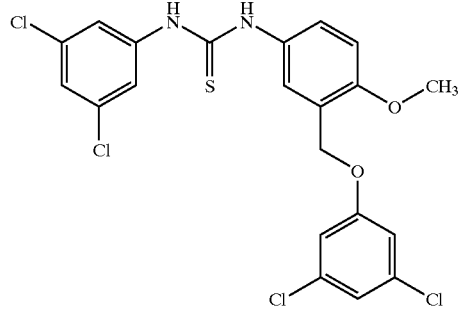
Compound # 46
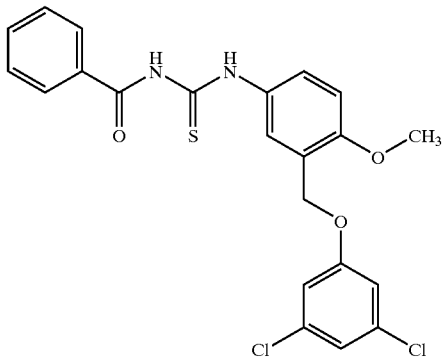
Compound # 47
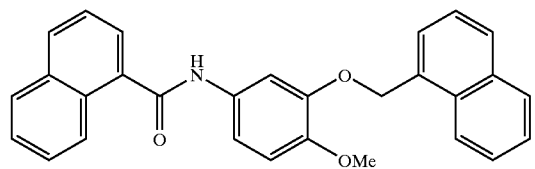
Compound # 48
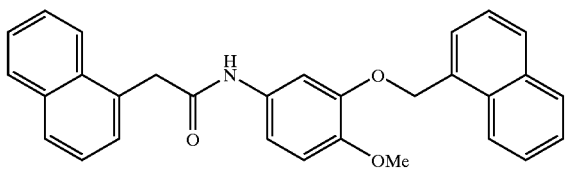

-continued

Compound # 49

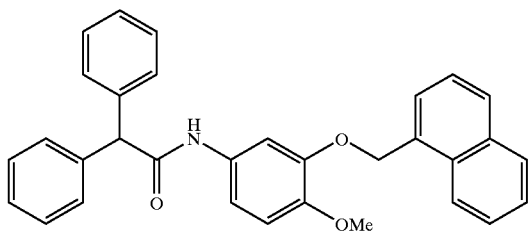

Compound # 50

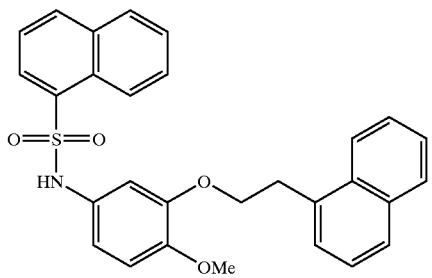

Compound # 51

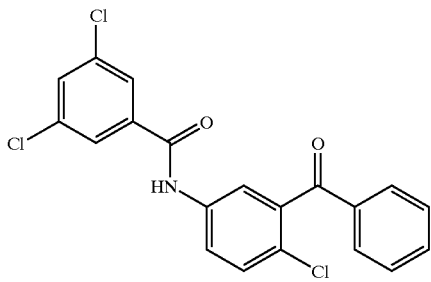

Compound # 52

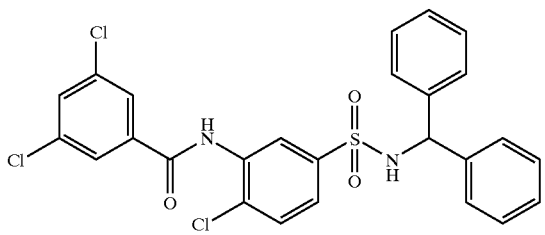

Compound # 53

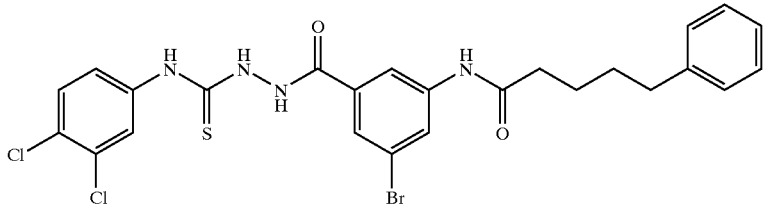

Preparation of Compounds of the Invention

The compounds of the invention can be prepared by a number of synthetic routes. The examples below detail schemes I to XIV and the preparation of specific compounds. However, one skilled in the art can modify the steps, reactants, and reaction conditions in the examples and schemes to arrive at numerous examples of compounds of the invention. In addition, if particular stereoisomers or mixtures are desired, the starting materials and/or reactants in the preparatory scheme can be selected and used accordingly. Alternatively or in addition, particular intermediates can be purified or enriched by chromatographic or enzymatic methods, or by manipulating reaction conditions or selective crystallization, to generate particular final products or mixtures. One skilled in the art is familiar with numerous methods to selectively produce or enrich for desired stereoisomers or mixtures. All of the compounds of the examples, including the intermediates, are specifically included in the compounds of the invention and can be used in the methods of the invention. Specific examples of synthetic intermediates which are useful as compounds of this invention include N-(3-amino-5-{[3-(trifluoromethyl)phenyl]amino}phenyl)(3,5-dichlorophenyl)formamide, used in the preparation of Exemplary Compound 10; N-(5-(2-aza-3-naphthylprop-2-enyl)-3)-{[3-(trifluoromethyl)phenyl]carbonylamino}phenyl)[3-(trifluoromethyl)phenyl]formamide, used in the preparation of Exemplary Compound 14; (3-bromo-5-{N-[3-(trifluoromethyl)phenyl]carbamoyl}phenyl)-N-[3-(trifluoromethyl)phenyl]formamide, used in the preparation of Exemplary Compounds 23–25; 1-{3-[(2-Naphthyl)methoxy]-5-nitrobenzoyl}-2-benzoylhydrazine, used in the preparation of Exemplary Compound 15; and 3,5-bis(benzyloxy) benzoate; 3,5-Bis(Benzyloxy)benzoic acid; and 3,5-Bis (Benzyloxy)benzoic acid chloride, used in the synthesis of Exemplary Compound 8.

The compounds of the invention may be prepared as salts or derivatives. Various salts and derivatives are known in the art and a non-limiting list of possible choices includes acid salts: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, mesylate, dimesylate, palmoate, pectinate, persulfate, 3-phenylpropionate, phosphates, picrate, pivalate, propionate, succinate, sulfates, tartrate, thiocyanate, tosylate, and undecanoate. Base salts may include: amine salts, ammonium salts, alkali metal salts such as sodium and potassium salts, alkaline earth metal salts such as calcium and magnesium salts, salts with organic bases such as dicyclohexylamine salts, N-methyl-D-glucosamine, and salts with amino acids, for example arginine or lysine. Nitrogen-containing groups of the compound can be quaternized with agents as: alkyl halides, for example methyl, ethyl, propyl, and butyl chlorides, bromides, or iodides; dialkyl sulfates, for example dimethyl, diethyl, dibutyl and diamyl sulfates, long chain halides, for example decyl, dodecly, lauryl, myristyl, or stearyl chlorides, bromides, or iodides; and aralkyl halides, for example benzyl and phenethyl bromides, chlorides, or iodides. The skilled artisan is familiar with methods for producing and testing any suitable salt or derivative. (See, for example, *Remington's Pharmaceutical Sciences*, Mack Publishing Co., Easton, Pa., 18$^{th}$ Edition, specifically incorporated herein by reference.)

Activity in Neuronal or Nervous System Cells

In general, activity in the nervous system for a particular compound can be identified by assaying for the ability to promote neurite outgrowth, protect neurons from damage by chemical treatments, promote the growth of neurons or neuronal cells, recover lost or damaged motor, functional or cognitive ability associated with nervous tissue or organs of the nervous system, or regenerate neurons. These activities can be useful in treating, diagnosing, or prognosing a number of human disease conditions, including, but not limited to, the neurological conditions described above, as well as disorders of the retina and optic nerve, vestibulocochlear disorders, and erectile dysfunction related to nerve damage caused during prostate surgery.

A number of animal model assays and cell culture assays have been developed and can be relied on for their clinical relevance to disease treatments, including the human diseases noted above. Each of the following references can be used as a source for these assays, and all of them are specifically incorporated herein by reference in their entirety for that purpose: Steiner, et al., *PNAS* 94: 2019–2024 (1997); Hamilton, et al., *Bioorgan. Med. Chem. Lett.* 7:1785–1790 (1997); McMahon, et al., *Curr. Opin. Neurobiol.* 5:616–624 (1995); Gash, et al., *Nature* 380:252–255 (1996); Gerlach, et al., *Eur. J. Pharmacol.-Mol. Pharmacol.* 208:273–286 (1991); Apfel, et al., *Brain Res.* 634:7–12 (1994); Wang, et al., *J. Pharmacol. Exp. Therap.* 282:1084–1093 (1997); Gold, et al., *Exp. Neurol.* 147:269–278 (1997); Hoffer et al., *J. Neural Transm.* [*Suppl.*] 49:1–10 (1997); Lyons, et al., *PNAS* 91:3191–3195 (1994); Yoshimoto and Siesjö, *Brain Res.*, 839, pp. 283–91 (1999); Kondo et al., *Neurochem Res.*, 24, pp. 9–13 (1999); Friberg et al., *J Neurosci.*, 18, pp. 5151–9 (1998); Sullivan et al., *Exp Neurol.*, February 2000; 161, 631–7 (2000).

Preferred methods for detecting neuronal activity include a neuroprotective assay, for example an organotypic slice culture of the spinal cord, in which a compound is tested for the ability to protect against treatment causing glutamate neurotoxicity. Sensory neuronal cultures of the dorsal root ganglia (DRG) can also be assayed for neurite outgrowth, an assay for neurotrophic activity. Cultured cells are treated with a compound of the invention and later assayed for the presence of new neurite fibers. The compounds can also be tested for their ability to inhibit the mitochondrial permeability transition by measuring large amplitude mitochondrial swelling of freshly isolated rat liver mitochondria in a spectrophotometric assay [Broekemeier, et al., *J. Biol. Chem.* 264: 7826–7830 (1989)].

The compounds of the present invention can further be assayed for their in vivo potency and efficacy using a common mouse model of a neurodegenerative disorder: Mice can be treated orally or subcutaneously, for example, with the compounds of the present invention, and subsequently be subjected to MPTP-treatment. MPTP (N-methyl-4-phenyl-1,2,3,6-tetrahydropyridine) is a systemically available neurotoxin that selectively destroys the dopaminergic neurons of the ventral midbrain as well as their forebrain projections. One skilled in the art is familiar with methods for assessing the integrity of the midbrain-forebrain projection in MPTP-lesioned mice that were treated with the compounds of this invention, and a relative preservation of the nerve fibres, nerve terminals, or of the dopaminergic cell bodies in the ventral midbrain, would be indicative of the relative neuroprotective efficacy of the compounds of this invention.

In the assays here exemplified, immunohistochemistry can aid in the visualization and quantitation of neurites, terminals and cell bodies.

The compounds of the invention can also be used to promote the establishment or maintenance of tissue or cell cultures. Similar to the use for promoting neuronal cell growth, the compounds can be added to primary, transformed, or established cell cultures. Particularly in the case of neuronal cells, the compounds can induce growth in culture and extend the culture lifetime of cells.

Binding to CyP and Other Uses

A recognized method for assessing the affinity of the compound to cyclophilin is the rotamase inhibition assay. For this purpose, the following references are specifically incorporated by reference and can be relied on to make assays of rotamase inhibition: Fischer, et al., *Biomed. Biochem. Acta* 43:1101–1112 (1984); Kofron, et al., *Biochem.* 30:6127–6134 (1991); Kofron et al., *J. Am. Chem. Soc.* 114:2670–2675 (1992); Harrison et al., *Biochem.* 29:3813–3816 (1990); Lang et al., *Nature* 329:268–270 (1987); Mucke et al., *Biochem.* 31:7848–7854 (1992); Schonbrunner et al., *J. Biol. Chem.* 266:3630–3635 (1991); Hsu et al., *J. Am. Chem. Soc.* 112:6745–6747 (1990); and Justice et al., *Biochem. Biophys. Res. Commun.* 171:445–450 (1990).

Additional uses for the compounds, which may or may not relate to CyP binding, are also included in the methods of the invention. For example, the compounds are useful to promote hair growth, and to prevent or retard hair loss. In murine models which mimic human premature hair follicle regression or human chemotherapy-induced hair loss, topical application of CsA was found to induce and maintain hair growth, and topical or systemic administration of CsA was found to protect from hair loss induced by cancer chemotherapeutic agents [see, e.g., Maurer, et al. *Am. J. Pathol.* 150 (4):1433–41 (1997); Paus, et al., *Am. J. Pathol.* 144, 719–34 (1994)]. It has been speculated that initiation of hair growth by CsA is unrelated to immunosuppression [Iwabuchi, et al., *J. Dermatol. Sci.* 9, 64–69 (1995)]. The compounds of the invention are useful in preventing or retarding hair loss in patients undergoing therapy with doxorubicin, carboplatin, cisplatin, cyclophosphamide, dactinomycin, etoposide, hexamethamelamine, ifosfamide, taxol, vincristine, bleomycin, 5-fluorouracil, and other agents useful in the therapy of cancer. The compounds of the invention are further useful in promoting hair growth in patients suffering from hair loss caused by one or a combination of the aforementioned chemotherapeutic agents. The compounds of the invention are further useful in the prevention of hair loss, and in the promotion of hair growth, in patients undergoing radiation therapy, and in patients suffering from alopecia areata, androgenetic alopecia/male pattern baldness, anagen effluvium, trichotillomania, traction alopecia, telogen effluvium, and hair loss induced by drugs such as, for example, methotrexate, nonsteroidal anti-inflammatory drugs, or beta blockers.

For these purposes, the compounds may be administered as part of pharmaceutical or cosmetic compositions, singly, in combination with other compounds of the invention, in combination with other hair growth-promoting or hair-loss preventing agents, or in combination with one or several other active agents such as, for example, antibiotic agents, antidandruff agents, and anti-inflammatory agents.

The compounds of the invention are also useful to treat or effect mitochondrial disorders, metabolic disorders, diabetes, or vision loss. The mitochondrion is increasingly being recognized as an important mediator of cell death in hypoxia, ischemia, and chemical toxicity. Disruption of the mitochondrial transmembrane potential is observed before other features of apoptosis (e.g. generation of reactive oxygen species or internucleosomal DNA fragmentation ("laddering")) become detectable. This applies to many different models of apoptosis induction, such as, for example, NGF-deprivation of cultured sympathetic neurons, dexamethasone-induced lymphocyte apoptosis, programmed lymphocyte death, activation-induced programmed cell death of T cell hybridomas, and tumor necrosis factor-induced death of lymphoma cells. [Marchetti, P., et al., *J. Exp. Med.* 184 (1996) 1155–1160]. Breakdown of mitochondrial transmembrane potential in proapoptotic cells has been attributed to the formation of an unspecific high conductance channel—the mitochondrial permeability transition pore—which leads to an increased permeability of the inner mitochondrial membrane to small molecular weight solutes. The ensuing release of intramitochondrial ions, influx of solutes, uncoupling of oxidative phosphorylation, and loss of metabolic intermediates accompanies large amplitude mitochondrial swelling and a depletion of cellular energy stores [see, e.g., Lemasters, J. J. et al., *Mol. Cell. Biochem.* 174 (1997) 159–165]. Importantly, CsA and non-immunosuppressive peptidic CsA analogues have been described to potently block pore conductance and inhibit the onset of the mitochondrial permeability transition [Broekemeier, K. M., et al., *J. Biol. Chem.* 264 (1989) 7826–7830; Zamzami, M., et al., *FEBS Lett.* 384 (1996) 53–7]. The mitochondrial permeability transition pore forms under calcium overload conditions such as occur in ischemia/reperfusion injury, and it has been found that administration of CsA and/or non-immunosuppressive peptidic CsA analogues, by blocking the permeability transition pore, leads to significant protection in experimental models of cerebral stroke [Matsumoto, S., et al., *J. Cereb. Blood Flow Metab.* 19 (1999) 736–41], cardiac ischemia [Griffiths, E. J. and Halestrap, A. P., *J. Mol. Cell Cardiol.* 25 (1993) 1461–1469], and hepatic ischemia/reperfusion injury [Leducq, N., et al., *Biochem. J.* 336 (1998) 501–6]. The compounds of the invention are useful in blocking the mitochondrial permeability transition pore; inhibiting breakdown of mitochondrial metabolism in cells which undergo oxidative stress, calcium overload, excitotoxic or hypoglycemic injury both in vitro and in vivo; inhibiting mitochondrial swelling; inhibiting, both in vivo and in vitro, breakdown of energy metabolism and cell death of mammalian cells following either physiological induction of programmed cell death through signal molecules such as, for example, tumor necrosis factor, or following physiological stress related to hypoxia, hypoglycemia, excitotoxic insult, or calcium overload. The inventive compounds are useful in preventing or delaying cell death in large scale/commercial scale cell culture. The compounds of the invention are further useful in the diagnosis, cure, mitigation, treatment, or prevention of ischemic injury or ischemia/reperfusion injury, such as mesenteric infarction, bowel ischemia, hepatic infarction or ischemia/reperfusion injury, renal infarction, splenic infarction, or cardiac ischemia or ischemia/reperfusion injury related, for example, to angina pectoris, congestive heart failure, or myocardial infarction.

Additional uses of the compounds of the invention include applications in the diagnosis, cure, mitigation, treatment, or prevention of Reye's syndrome; ophthalmic disorders such as glaucoma, ischemic or vascular retinopathies, or degeneration of the photoreceptor cell layer. The invention also provides a method of preventing or reducing tissue damage of organs used in organ transplantation surgery, comprising contacting said organs with a compound of Formula I.

CsA and its non-immunosuppressive peptidic analogues have also been found to potently inhibit the growth of pathogenic protozoan parasites, such as *Cryptosporidium parvum, Plasmodium falciparum, Plasmodium vivax*, Schistosoma spec., and *Toxoplasma gondii* [Perkins, et al., *Antimicrob. Agents Chemother.* 42: 843–848 (1998)]. Although antiprotozoan activity appears not to be correlated with immunosuppressive or PPIase inhibitory activity [Bell, et al., *Biochem. Pharmacol.* 48:495–503 (1994); Khattab, et al., *Exp. Parasitol.* 90:103–109 (1998)], the protozoan cyclophilin, complexed to CsA or its nonimmunosuppressive analogues, has been proposed to play an active role in mediating the antiparasitic effects of peptidic cyclophilin ligands [Berriman and Fairlamb, *Biochem. J.* 334:437–445 (1998)]. CyA and its non-immunosuppressive analogues also inhibit reproduction of filarial parasites in vivo with a potency unrelated to their immunosuppressive activity and their activity against Plasmodium [Zahner and Schultheiss, *J. Helminthol.* 61:282–90 (1987)], and have been shown to exert direct antihelmintic effects [McLauchlan, et al., *Parasitology* 121:661–70 (2000)].

The compounds of this invention are useful in the diagnosis, cure, mitigation, treatment, or prevention of infections with pathogenic protozoan or helmintic parasites in animals, including humans. In humans, the present compounds find application in the treatment of conditions such as, for example, malaria, river blindness, lymphatic filariasis, intestinal roundworm infection, tapeworm infection, pinworm infection, toxoplasmosis, leishmaniasis, trypanosomiasis, and bilharzia.

The compounds of this invention are also useful in affecting the viral replication process of the HIV-1 virus. The infectivity of the HIV-1 virus is believed to depend critically upon an interaction of the viral Gag polyprotein capsid complex with host Cyclophilin A. [Streblow et al. *Virology* 245 (1998) 197–202; Li et al. *J. Med. Chem.* 43, (2000) 1770–9]. The compounds of this invention can function to inhibit or disrupt the interaction of human host CyPA with HIV-1 Gag proteins, to decrease or eliminate the infectivity of the HIV-1 virus, to treat or prevent infection of humans with the HIV-1 virus, and to treat or prevent acquired immune deficiency syndrome (AIDS) associated with HIV-1 infection. The compounds of this invention are further useful in the diagnosis, treatment, cure, mitigation or prevention of infections with strains of the human immunodeficiency virus other than HIV-1, and of infections caused by other pathogenic viruses, such as influenza viruses.

Pharmaceutical Formulations and Routes of Administration

The compounds of the invention have utility in pharmacological compositions for the treatment and prevention of various neurological, ischemic, and inflammatory disorders or for various in vitro and cell culture treatments. The compounds also have utility in pharmacological compositions for the treatment and prevention of HIV-infection, promotion of hair growth, immunosuppression, mitochondrial disorders, traumatic injury to nervous tissue, or conditions associated with retinal and optic nerve damage. The compounds of the invention may be prepared as a salt or derivative, as described above.

A compound of the invention can be administered to an animal or human patient by itself or in pharmaceutical compositions where it is mixed with suitable carriers or excipients, at doses to treat or ameliorate various conditions. The compounds according to the present invention preferably have sufficient stability, potency, selectivity, solubility and availability to be safe and effective in treating diseases, injuries and other abnormal conditions or insults to the central nervous system, the peripheral nerves, and other organs. A therapeutically effective dose refers to that amount of the compound sufficient to effect an activity in a nerve or neuronal cell, to produce a detectable change in a cell or organism, or to treat a disorder in a human or other mammal. The word "treat" in its various grammatical forms as used in relation to the present invention refers to preventing, curing, reversing, attenuating, alleviating, minimizing, suppressing, ameliorating or halting the deleterious effects of a disease state, disease progression, injury, wound, ischemia, disease causative agent (e.g., bacteria, protozoans, parasites, fungi, viruses, viroids and/or prions), surgical procedure or other abnormal or detrimental condition (all of which are collectively referred to as "disorders," as will be appreciated by the person of skill in the art). A "therapeutically effective amount" of a compound according to the invention is an amount that can achieve effective treatment, and such amounts can be determined in accordance with the present teachings by one skilled in the art.

The methods of the present invention comprise (i.) administration of a compound of Formula I, where the compound is itself therapeutically active in the treatment of the targeted medical condition, or (ii.) administration of a prodrug of a compound of Formula I, wherein such prodrug is any compound which is capable of undergoing metabolic conversion to a compound of Formula I following administration, or (iii.) administration of a compound of Formula I where the compound is capable of undergoing metabolic conversion to a metabolite following administration, and where the metabolite is therapeutically active in the treatment of the targeted medical condition, or (iv.) administration of a metabolite of a compound of Formula I, where the metabolite is therapeutically active in the treatment of the targeted medical condition. Thus, the use of a compound of Formula I in the methods of the present invention explicitly includes not only the use of the compound itself, but also the modifications ii, iii, and iv discussed in this paragraph, and all such modifications are explicitly intended to be within the scope of the following claims.

Therapeutically effective doses may be administered alone or as adjunctive therapy in combination with other treatments. Techniques for the formulation and administration of the compounds of the instant application may be found in *Remington's Pharmaceutical Sciences,* Mack Publishing Co., Easton, Pa., 18$^{th}$ edition (1990).

Suitable routes of administration may, for example, include oral, rectal, transmucosal, buccal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the agent of the present invention in a targeted drug delivery system, for example in a liposome coated with an antibody. The liposomes will be targeted to and taken up selectively by cells expressing the appropriate antigen.

The pharmaceutical compositions of the present invention may be manufactured in a manner that is itself known, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and auxiliaries, which facilitate processing of the active compounds into preparations, which can thus be used pharmaceutically.

For injection, the agents of the invention may be formulated in aqueous solutions, preferably in physiologically compatible buffers, such as Hank's solution, Ringer's solution, or physiological saline buffer. For transmucosal or buccal administration, penetrants appropriate to the barrier to be permeated may be used in the formulation. Such penetrants are known in the art.

For oral administration, the compounds can be formulated readily by combining the active compounds with pharmaceutically acceptable carriers, well known to those in the art. Such carriers enable the compounds of the invention to be formulated as tablets, pills, capsules, liquids, quick-dissolving preparations, gels, syrups, slurries, suspensions and the like, for oral ingestion by a patient to be treated. Pharmaceutical preparations for oral use of the compounds of this invention can be obtained by employing a solid excipient, optionally grinding a resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In general, the pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. If desired, disintegrating agents may be added, such as the cross-linked polyvinyl pyrrolidone, agar, or alginic acid or a salt thereof such as sodium alginate or a number of others disintegrants [see, for example, *Remington's Pharmaceutical Sciences*, Mack Publishing Co., Easton, Pa., 18$^{th}$ edition (1990)].

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, pressurized air, or other suitable gas or mixture. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions. Alternatively, the active ingredient may be in powder form for reconstitution with a suitable vehicle, e.g., sterile pyrogen-free water, before use.

The compounds may also be formulated in rectal compositions such as suppositories, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds of the invention may further be formulated in pharmaceutical or cosmetic compositions for topical application to the skin in the form of an aqueous, alcoholic, aqueous/alcoholic or oily solution, or of a dispersion of the lotion or serum type, of an emulsion having a liquid or semi-liquid consistency of the milk type, obtained by dispersion of a fatty phase in an aqueous phase (O/W) or vice versa (W/O), or of a suspension or of an emulsion with a soft consistency of the aqueous or anhydrous gel, foam or cream type, or, alternatively, of microcapsules or microparticles, or of a vesicular dispersion of ionic and/or nonionic type, or may further be administered in the form of an aerosol composition comprising a pressurized propellent agent. The compounds of the invention can also be formulated into various compositions for hair care and, in particular, shampoos, hair-setting lotions, treating lotions, styling creams or gels, dye compositions (in particular oxidation dyes), optionally in the form of color-enhancing shampoos, hair-restructuring lotions, permanent-wave compositions, and the like. Pharmaceutical or cosmetic compositions comprising compounds of the invention can also contain additives and adjuvants which are conventional in the cosmetics field, such as gelling agents, preservatives, antioxidants, solvents, fragrances, fillers, screening agents, odor absorbers and colorants. The amounts of these different additives and adjuvants are those typically employed in the cosmetics field and range, for example, from 0.01% to 20% of the total weight of the composition, preferably 0.1% to 10%, and more preferably 0.5% to 5%. In addition to one or several compounds of the invention, compositions for topical application may further contain additional agents already known in the art to promote hair growth or to prevent or retard hair loss, such as, without limitation, tocopherol nicotinate, benzyl nicotinate or 2,4-diamino-6-piperidinopyrimidine 3-oxide, or may contain other active agents such as antibacterial agents, antiparasitic agents, antifungal agents, antiviral agents, anti-inflammatory agents, antipruriginous agents, anaesthetic agents, keratolytic agents, antiseborrhoeic agents, antidandruff agents, or antiacne agents. The cosmetic or pharmaceutical compositions according to the invention can be topically applied onto the alopecic areas of the scalp and skin of an individual and optionally maintained in contact for a number of hours and optionally rinsed. It is possible, for example, to apply the composition containing an effective amount of at least one compound of the invention in the evening, to retain the composition in contact overnight and optionally to shampoo in the morning. These applications can be repeated daily for one or a number of months, depending on the particular individuals involved.

Liposomes and emulsions are well known examples of delivery vehicles or carriers for hydrophobic drugs. Certain organic solvents such as dimethylsulfoxide also may be employed. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

Pharmaceutical compositions suitable for use in the present invention include compositions wherein the active ingredients are contained in an effective amount to achieve their intended purpose, to effect a therapeutic benefit, or to effect a detectable change in the function of a cell, tissue, or organ. More specifically, a therapeutically effective amount means an amount effective to prevent the development of or to alleviate the existing symptoms of the subject being treated. Determining the effective amount is well within the capability of those skilled in the art, especially in light of the detailed disclosure provided herein.

Toxicity and therapeutic efficacy of the compounds or compositions can be determined by standard pharmaceutical, pharmacological, and toxicological procedures in cell cultures or experimental animals. For example, numerous methods for determining the $LD_{50}$ (the dose lethal to 50% of the population) and the $ED_{50}$ (the dose therapeutically effective in 50% of the population) exist. The dose ratio between toxic and therapeutic effects is the therapeutic index, which can be expressed as the ratio between $LD_{50}$ and $ED_{50}$. Compounds and compositions exhibiting high therapeutic indices are preferred. The data obtained from cell culture assays or animal studies can be used in formulating a range of dosages for use in humans. [See, for example, Fingl et al., in *The Pharmacological Basis of Therapeutics*, Ch. 1 p. 1 (1975)].

The compounds of the present invention may be administered by a single dose, multiple discrete doses or continuous infusion. Because the compounds preferably are non-peptidic, easily diffusible and relatively stable, they can be well-suited to continuous infusion.

Dose levels on the order of about 0.1 mg to about 10,000 mg of the active ingredient are useful in the treatment of the above conditions, with preferred levels being about 0.1 mg to about 1,000 mg. The specific dose level, and thus the therapeutically-effective amount, for any particular patient will vary depending upon a variety of factors, including the activity of the specific compound employed and its bioavailability at the site of drug action; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models also are helpful. The considerations for determining the proper dose levels are available to the skilled person.

Certain compounds can administered in lyophilized form. In this case, 1 to 1000 mg of a compound of the present invention may be lyophilized in individual vials, together with a carrier and a buffer, such as mannitol and sodium phospshate. The compound may be reconstituted in the vials with bacteriostatic water before administration.

In treating neurological disorders resulting from global or focal ischemia, for example, the compounds of the present invention are preferably administered orally, rectally, parenterally or topically at least 1 to 6 times daily, and may follow an initial bolus dose of higher concentration.

For the compounds, methods, and uses of the present invention, any administration regimen regulating the timing and sequence of drug delivery can be used and repeated as necessary to effect treatment. Such regimen may include pretreatment and/or co-administration with additional therapeutic agents.

Synthetic Routes to Production of Exemplary Compounds of the Invention

EXAMPLE 1

Synthesis of Exemplary Compounds 2, 3, 16, 17, 18, 19, 20, 21, 22, 23, 24, 25, 26, 32, 37, 38, 41, 42, and 43

Symmetrical bis-amides, such as Exemplary Compounds 2, 3, 16, 17, 18, 19, 20, 21, 22, 23, 24, 25, 26, 32, 37, 38, 41, 42, and 43, may be prepared by reacting aryl bis-carboxylic acids or chlorides, obtained from the corresponding esters, with appropriate amines, as in Scheme 1:

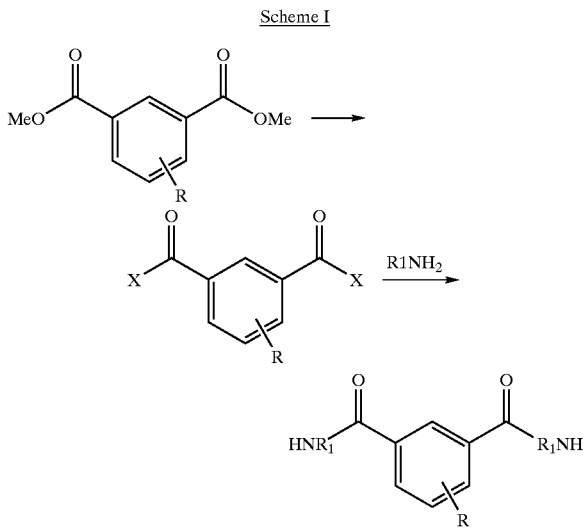

Scheme I

Synthesis of 1,3-Bis-[3,4-dichlorophenyl)aminocarbonyl]-5-(benzyloxy)benzene (Exemplary Compound 43)

5-Phenoxymethyl-isophthalic acid dimethyl ester. A mixture of 5-hydroxyisophthalic acid dimethyl ester (700 mg; 3.33 mmol), benzyl bromide (635 mg; 3.70 mmol), and potassium carbonate (510 mg; 3.7 mmol) in acetone was refluxed overnight. After cooling, the mixture was partitioned between water and ethyl acetate. The layers were separated, the aqueous layer was extracted twice more with ethyl acetate, and the combined organic portions were washed with brine, dried, and concentrated to provide a crude solid. Recrystallization from ethyl acetate/hexanes furnished the product as a white crystalline material, mp 95–97° C., $^1$H NMR (400 MHz): d 3.94 (s, 6H); 5.15 (s, 2H): 7.42 (m, 5H); 7.84 (s, 2H); 8.29 (s, 1H).

5-Phenoxymethylisophthalic acid. A mixture of 5-phenoxymethyl-isophthalic acid dimethyl ester (5.5 g; 12.3 mmol) and 20% ethanolic potassium hydroxide (250 mL) was refluxed overnight. After cooling and concentrating, the residue was dissolved in water, acidified with 2N HCl, and the product was extracted into ethyl acetate. The organic extracts were washed with brine, dried, and concentrated to obtain the diacid as a white powder, 4.8 g.

1,3-Bis-[3,4-dichlorophenyl)aminocarbonyl]-5-(benzyloxy)benzene (Exemplary Compound 43). A solution of the diacid in thionyl chloride (50 mL) was refluxed overnight. The volatiles were removed in vacuo to obtain the bis-acid chloride (500 mg), which was immediately dissolved in dimethylacetamide (10 ml) and treated with 3,5-dichloroaniline (520 mg; 3.23 mmol) and triethylamine (2 ml). After stirring this mixture overnight, it was poured on ice, and the resulting solid was collected by filtration, washed with water, and dried. Recrystallization from acetone provided the product, $^1$H NMR (DMSO-d6, 400 MHz) 10.64 (s, 2H); 8.17–8.13 (m, 3H); 7.83–7.76 (m, 4H); 7.65 (d, J=9.0 Hz, 2H); 7.52 (d, J=7.0 Hz, 2H); 7.44 (t, J=7.0 Hz, 2H); 7.40–7.35 (m, 1H); 5.29 (s, 2H). Anal: Calcd for: C, 57.88; H, 3.24; N, 5. Found: C, 57.66; H, 3.37; N, 4.93.

5-Hydroxy-N,N'-bis-(3-trifluoromethyl-phenyl)-isophthalamide (Exemplary Compound 2). $^1$H NMR (CDCl$_3$, 400 MHz) δ10.01 (s, 2H), 8.34 (s, 2H), 8.18 (d, 2H), 8.12 (s, 1H), 7.66 (s, 2H), 7.57 (t, 2H), 7.42 (d, 2H). Anal: Calcd for: C, 56.42; H, 3.01; N, 5.98. Found: C, 56.31; H, 3.29; N, 6.11.

5-Naphthalen-1-yl-N,N'-bis-(3-trifluoromethyl-phenyl) isophthalamide (Exemplary Compound 3). $^1$H NMR (DMSO-d6, 400 MHz) δ10.77 (s, 2H), 8.739s, 1H), 8.36 (s, 2H), 8.269s, 2H), 8.06 (m, 4H), 7.86 (t, 1H), 7.46–7.61 (m, 8H).

(3-(2-(4-pyridyl)vinyl)-5-{N-[3-(trifluoromethyl)phenyl] carbamoyl}phenyl)-N-[3-(trifluoromethyl)phenyl] formamide (Exemplary Compound 16). $^1$H NMR (CDCl3, 400 MHz) 9.98 (s, 2H), 8.46 (s, 1H), 8.34 (s, 2H0, 8.229s, 1H), 7.78 (d, 2H), 7.70 (d, 2H), 7.49 (s, 1H), 7.32–7.41 (m, 9H). Anal: Calcd for: C, 61.88; H, 3.52; N, 7.73. Found: C, 61.78; H, 3.76; N, 7.68.

(5-(2-naphthyloxy)-3-{N-[3-(trifluoromethyl)phenyl] carbamoyl}phenyl)-N-[3-(trifluoromethyl)phenyl] formamide (Exemplary Compound 17). $^1$H NMR (Acetone-d6, 400 MHz) 9.87 (s, 2H, NH), 8.28 (s, 1H), 8.149 s, 2H), 7.93 (d, 2H), 7.84 (d, 1H), 7.80(s, 2H), 7.76 (s, 1H), 7.70 (d, 1H), 7.48 (t, 2H), 7.40 (t, 1H), 7.36 (t, 1H0, 7.309d, 2H), 7.229 d, 1H). Anal: Calcd for: C, 64.65; H, 3.39; N, 4.71. Found: C, 64.88; H, 3.57; N, 4.68.

(5-(2-naphthyl)-3-{N-[3-(trifluoromethyl)phenyl] carbamoyl}phenyl)-N-[3-(trifluoromethyl)phenyl] formamide (Exemplary Compound 18). $^1$H NMR (Acetone-d6, 400 MHz) 10.35 (s, NH, 2H), 8.63 (s, 2H), 8.57 (s, 1H), 8.45 (m, 3H), 8.15 (d, 1H), 8.10 (d, 1H), 8.03 (d, 1H), 7.65 (d, 1H), 7.61 (t, 1H), 7.56 (t, 1H), 7.52 (d, 2). Anal: Calcd for: C, 66.44; H, 3.48; N, 4.84. Found: C, 66.86; H, 3.64; N, 4.97.

1-[(3,4-dichlorophenyl)oxymethy]-3,5-bis-{[2-(3,4-dichlorophenyl)ethyl]aminocarbonyl}benzene (Exemplary Compound 19). $^1$H NMR (DMSO-d6, 400 MHz) 8.70 (s, 2H); 8.19 (s, 1H); 7.98 (s, 2H); 7.52–7.49 (m, 5H); 7.36 (s, 1H); 7.23 (d, J=8.0, 2H); 7.07 (d, J=9.0, 1H); 5.22 (s, 2H); 3.52–3.49 (m, 4H); 2.89–2.84 (m, 4H). Anal: Calcd for: C, 54.34; H, 3.53; N, 4.09; Cl, 31.04. Found: C, 54.23; H, 3.62; N, 4.02; Cl, 30.98.

1-[(3,4-dichlorophenyl)oxymethyl]-3,5-bis-[(3,5-dichlorophenyl)aminocarbonyl]benzene (Exemplary Compound 20). ¹H NMR (DMSO-d6, 400 MHz) 10.82 (s, 2H); 8.55 (s, 1H); 8.24 (s, 2H); 7.93 (s, 4H); 7.58 (d, J=9.0, 1H); 7.42 (s, 1H); 7.38 (s, 2H); 7.12 (d, J=9.0, 1H); 5.34 (s, 2H). Anal: Calcd for: C, 51.54; H, 2.56; N, 4.45. Found: C, 51.74; H, 3.03; N, 4.64.

1-[4-(2-cyanophenyl)benzyl]oxy-3,5-bis{2-[(3,4-dichlorophenyl)ethyl]aminocarbonyl}benzene (Exemplary Compound 21). ¹H NMR (DMSO-d6, 400 MHz) 8.65 (t, J=5.5, 2H); 7.97 (d, J=7.5, 1H); 7.87 (s, 1H); 7.81 (t, J=7.5, 1H); 7.69–7.50 (m, 12H); 7.23 (d, J=8.0, 2H); 5.28 (s, 2H); 3.51 (q, J=6.5, 4H); 2.87 (t, J=7.0, 4H). Anal: Calcd for: C, 63.61; H, 4.07; N, 5.86; Cl, 19.77. Found: C, 63.51; H, 4.18; N, 5.80; Cl, 19.66.

1-[4-(2-cyanophenyl)benzyl]oxy-3,5-bis-[(3-cyanophenyl)aminocarbonyl]benzene (Exemplary Compound 22). ¹H NMR (DMSO-d6, 400 MHz) 10.76 (s, 2H); 8.29 (s, 2H); 8.22 (s, 1H); 8.14–8.07 (m, 2H); 7.98 (d, J=7.5, 1H); 7.89 (s, 2H); 7.81 (t, J=8.0, 1H); 7.72–7.56 (m, 10H); 5.40 (s, 2H). Anal: Calcd for: C, 73.09; H, 4.26; N, 11.84. Found: C, 73.17; H, 4.27; N, 11.82.

(5-(2-(2-5,6,7,8-tetrahydronaphthyl)ethyl)-3-{N-[3-(trifluoromethyl)phenyl]carbamoyl}phenyl)-N-[3-(trifluoromethyl)phenyl]formamide (Exemplary Compound 23). ¹H NMR (DMSO-d6, 400 MHz) 10.049s, 2H, NH), 8.499s, 1H), 8.38 (s, 2H), 8.13 (m, 4H), 7.65 (t, 2H), 7.55 (d, 2H), 7.11 (s, 1H), 7.01 (d, 2H0, 3.18 (t, 2H), 3.03 (t, 2H), 2.75 (m, 4H), 1.84 (m, 4H). Anal: Calcd for: C, 66.88; H, 4.62; N, 4.59. Found: C, 66.50; H, 4.81; N, 4.49.

(5-(2-(2-naphthyl)ethyl)-3-{N-[3-(trifluoromethyl)phenyl]carbamoyl}phenyl)-N-[3-(trifluoromethyl)phenyl]formamide (Exemplary Compound 24). ¹H NMR (DMSO-d6, 400 MHz) 9.88 (s, 2H, NH), 8.30 (s, 1H), 8.19 (s, 2H), 8.06 (s, 2H), 7.94 (d, 2H), 7.71 (d, 2H), 7.69 (d, 1H), 7.61 (s, 1H), 7.53 (t, 2H), 7.35 (m, 4H), 3.11 (s, 4H). Anal: Calcd for: C, 67.32; H, 3.99; N, 4.62. Found: C, 67.04; H, 4.06; N, 4.60.

(5-(2-(2-naphthyl)vinyl)-3-{N-[3-(trifluoromethyl)phenyl]carbamoyl}phenyl)-N-[3-(trifluoromethyl)phenyl]formamide (Exemplary Compound 25). ¹H NMR (DMSO-d6, 400 MHz) 10.81 (s, 2H, NH), 8.5 (s, 3H), 8.28 (s, 2H), 8.15 (d, 2H), 8.12 (s, 1H), 7.979 s, 2H), 7.93 (t, 2H), 7.64 (m, 4H), 7.529 m, 4H). Anal: Calcd for: C, 65.22; H, 3.93; N, 4.47. Found: C, 65.20; H, 3.67; N, 4.73.

(3-bromo-5-{N-[3-(trifluoromethyl)phenyl]carbamoyl}phenyl)-N-[3-(trifluoromethyl)phenyl]formamide (Exemplary Compound 26). ¹H NMR (DMSO-d6+D2O, 400 MHz) 10.6 (s,2H, NH), 8.64 (s, 1H), 8.819 s, 2H), 8.53(s, 2H), 8.22 (d, 2H), 7.76 (t, 2H); 7.62 (d, 2H). Anal: Calcd for: C, 49.74; H, 2.47; N, 5.27. Found: C, 49.56; H, 2.40; N, 5.29.

1-(3,4-dichlorobenzyloxy)-3,5-bis-[(3,4,5-trichlorophenyl)aminocarbonyl]benzene (Exemplary Compound 32). ¹H NMR (DMSO-d6, 400 MHz) 10.69 (s, 1H); 8.16 (s, 1H); 8.11 (s, 4H); 7.82–7.77 (m, 3H); 7.70 (d, J=8.5 Hz, 1H); 7.50 (d, J=8.5 Hz, 1H); 5.28 (s, 2H). Anal: Calcd for: C, 46.46; H, 2.02; N, 4.01. Found: C, 46.38; H, 2.17; N, 3.94.

3-{[(3-Trifluoromethyl-4-chlorophenyl)aminocarbonyl]benzyloxy}-1,5-bis-[(3-trifluoromethyl-4-chlorophenyl)aminocarbonyl]benzene (Exemplary Compound 37. ¹H NMR (DMSO-d6, 400 MHz) 10.80 (s, 2H); 10.71 (s, 1H); 8.37 (s, 3H); 8.23 (s, 1H); 8.30–8.07 (m, 4H); 7.99 (d, J=8.0 Hz, 1H); 7.89 (s, 2H); 7.82–7.71 (m, 4H); 7.63 (t, J=7.5 Hz, 1H); 5.41 (s, 2H). Anal: Calcd for: C, 52.35; H, 2.49; N, 4.95. Found: C, 52.36; H, 2.54; N, 5.09.

3-{[(3,4-dichlorophenyl)aminocarbonyl]benzyloxy}-1,5-bis-[(3,4-dichloro-phenyl)aminocarbonyl]benzene (Exemplary Compound 38). ¹H NMR (DMSO-d6, 400 MHz) 10.65 (s, 2H); 10.57 (s, 1H); 8.16 (s, 4H); 8.10 (s, 1H); 7.97 (d, J=8.0 Hz, 1H); 7.85 (s, 2H); 7.83–7.77 (m, 4H); 7.69–7.51 (m, 4H); 5.39 (s, 2H). Anal: Calcd for: C, 53.29; H, 3.03; N, 5.48. Found: C, 53.20; H, 2.87; N, 5.52.

{2-bromo-5-[N-(3-nitrophenyl)carbamoyl]phenyl}-N-(3-nitrophenyl) formamide (Exemplary Compound 41). ¹H NMR (DMSO-d6, 400 MHz) 7.68 (q, 2H); 7.95–8.07 (m, 5H); 8.21 (t, 2H); 8.78 (s, 2H); Anal: Calcd for: C, 49.59; H, 2.82; N, 11.34. Found: C, 49.75; H, 2.86; N, 11.38.

1,3-Bis[(3-trifluoromethylphenyl)aminocarbonyl]-5-[(2-naphthyl) methyloxy]benzene (Exemplary Compound 42). ¹H NMR (DMSO-d6, 400 MHz) 10.73 (s, 2H); 8.26 (s, 2H); 8.23 (s, 1H); 8.12–8.05 (m, 3H); 8.02–7.92 (m, 3H); 7.91 (s, 2H); 7.66–7.61 (m, 3H); 7.57–7.52 (m, 2H); 7.49 (d, J=7.5 Hz, 2H); 5.48 (s, 2H). Anal; Calcd for: C, 65.13; H, 3.64; N, 4.60. Found: C, 64.88; H, 3.80; N, 4.69.

The intermediate diacid for Exemplary Compounds 42, 32, 22, and 21, and for Exemplary Compounds 19 and 20, was synthesized as shown in Scheme I-A and I-B, respectively:

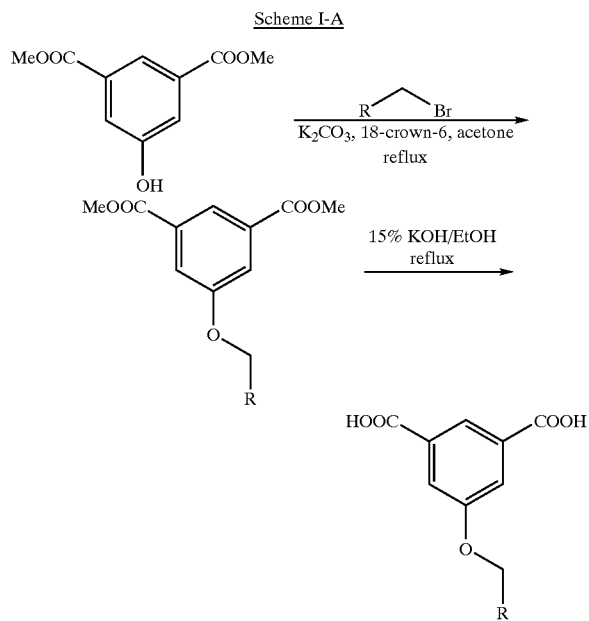

Scheme I-A

Dimethyl 3-(3,4-dichlorobenzyloxy)isophthalate. A mixture of 5-hydroxyisophthalic acid dimethyl ester (4.62 g, 20 mmol), (3,4-dichloro)benzyl bromide (2.77 mL, 20 mmol), potassium carbonate (4.15 g, 30 mmol), and dicyclohexano-18-crown-6 (80 mg) in acetone (100 mL) was stirred and refluxed overnight, cooled to room temperature, and poured on ice-water (200 g). Precipitate formed was filtered, washed with water (5×50 mL), and air-dried to give 6.94 g (94%) of the substituted diester:

¹H NMR (CDCl₃, 400 MHz), δ:8.31 (s, 1H); 7.81 (s, 2H); 7.55 (s, 1H); 7.47 (d, J=8.0 Hz, 1H); 7.27 (d, J=8.5 Hz, 1H); 5.10 (s, 2H); 3.95 (s, 6H);

Scheme I-B

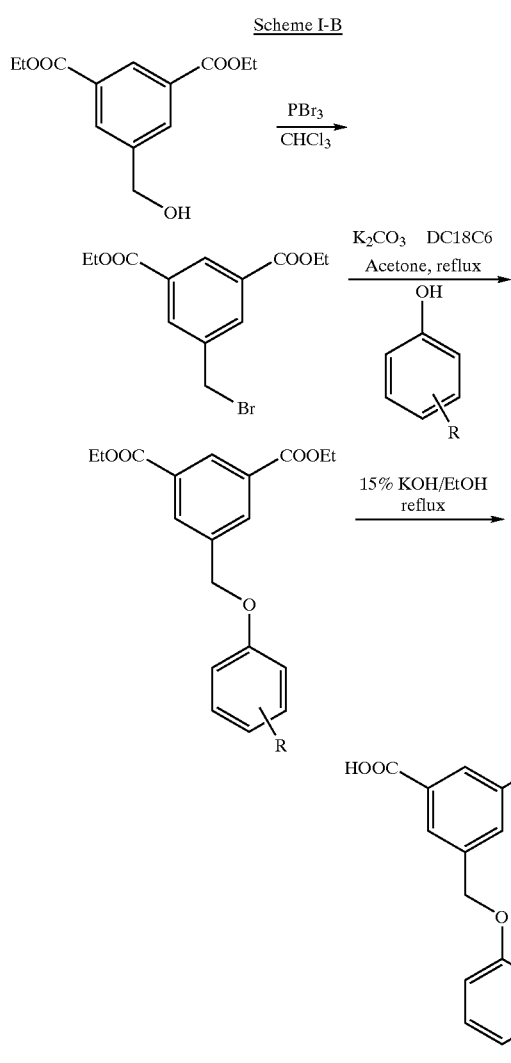

3-(3,4-Dichlorobenzyloxy)isophthalic acid. A suspension of dimethyl 3-(3,4-dichlorobenzyloxy)isophthalate (6.94 g, 18.8 mmol) in the mixture of KOH (15% aq., 50 mL) and EtOH (100 mL) was refluxed for 0.5 h, then cooled to room temperature and stirred overnight. The formed solution was acidified with HCl conc. (to pH 2), and bulky precipitate formed was filtered and air-dried. White solid; yield 5.66 g (88%).

The above diacid was carried on to the final product (Exemplary Compound 42) by the method of Scheme I.

Following the procedure in Scheme I-A, the requisite intermediates for Exemplary Compounds 21, 22, and 32 were prepared and converted to final products by the methods of Scheme I.

3,5-Bis(ethoxycarbonyl)benzyl bromide. A solution of 3,5-bis(ethoxycarbonyl) benzyl alcohol (2.53 g, 10 mmol) and $PBr_3$ (0.95 mL, 10 mmol) in chloroform (50 mL) was stirred at room temperature overnight. Yellowish solution was washed with water (50 mL). The organic layer was separated, dried with $Na_2SO_4$ anhyd. and evaporated in vacuo to provide the benzylic bromide as a white solid, yield 3.10 g (98%). $^1$H NMR (CDCl$_3$, 400 MHz), δ8.61 (s, 1H); 8.25 (s, 2H); 4.55 (s, 2H); 4.42 (q, J=7.0 Hz, 4H); 1.43 (t, J=7.0 Hz, 6H).

Dimethyl 5-[(3,4-dichlorophenyl)oxymethyl]isophthalate. The title compound was prepared in a manner similar to that described for dimethyl 3-(3,4-dichlorobenzyloxy) isophthalate (Scheme I-A), from 3,4-dichlorophenol and 3,5-bis(ethoxycarbonyl)benzyl bromide. Yield 90%. $^1$H NMR (CDCl$_3$, 400 MHz), δ8.53 (s, 1H); 8.27 (s, 2H); 7.53 (d, J=8.0 Hz, 2H); 7.38 (s, 1H); 7.08 (d, J=8.0 Hz, 1H); 5.32 (s, 2H); 4.46 (q, J=7.0 Hz, 4H); 1.45 (t, J=7.0 Hz, 6H).

5-[(3,4-Dichlorophenyl)oxymethyl]isophthalic acid. The title compound was prepared by hydrolyzing the diester to the diacid as described in Scheme I-A. White microcrystals, yield 96%.

The above diacid was converted to Exemplary Compounds 19 and 20 by the methods of Scheme I.

The method of Scheme I-C was used to prepare Exemplary Compound 16, below.

Synthesis of (3-(2-(4-pyridyl)vinyl)-5-{N-[3-(trifluoromethyl)phenyl]carbamoyl}phenyl)-N-[3-(trifluoromethyl)phenyl]formamide (Exemplary Compound 16)

5-(2-pyridin-4-yl-vinyl)-isophthalic acid dimethylester. A solution of 5-bromoisophthalic acid dimethylester (542 mg, 2 mmol) and 4-vinylpyridine (206 mg, 2 mmol), Pd(OAc)$_2$ (8 mg), tri-o-tolylphosphine (30 mg) in 5 ml Et$_3$N (5 ml) was stirred at 80° C. for overnight. The reaction mixture was purified by silica gel column eluted by 50% EtOAc in hexane to afford the product (65% yield). MS+=297. $^1$H NMR (CDCl3, 400 MHz) 8.64 (s, 1H), 8.61 (d, 2H), 8.38 (d, 2H), 7.40 (m, 2H), 7.35 (m, 1H), 7.21 (m, 1H), 4.02 (s, 6H);

Scheme I-C

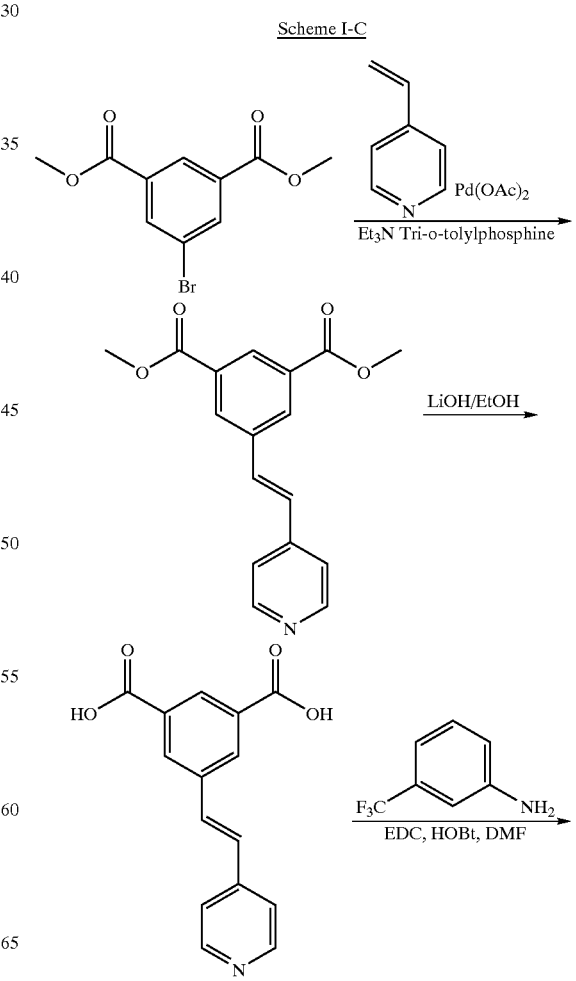

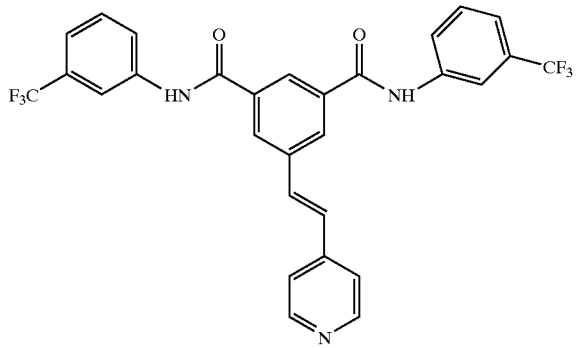

5-(2-pyridin-4-yl-vinyl)-isophthalic acid. A solution of LiOH (2.5 mmol) in water (1 ml) was added to 5-(2-pyridin-4-yl-vinyl)-isophthalic acid dimethylester (297 mg, 1 mmol) suspended in 5 ml EtOH. The mixture was stirred at room temperature. The reaction was monitored by TLC until completion. 2.5 ml 1 M HCl solution was then added and the mixture was evaporated to dryness. The product was used in next step without further purification.

(3-(2-(4-pyridyl)vinyl)-5-{N-[3-(trifluoromethyl)phenyl] carbamoyl}phenyl)-N-[3-(trifluoromethyl)phenyl] formamide (Exemplary Compound 16). A solution of EDC (287 mg, 1.5 mmol) in 5 ml DMF was slowly added to a mixture solution containing the product from previous step, HOBt (270 mg, 2 mmol), and 3-trifluromethylaniline (322 mg, 2 mmol) in 10 ml DMF at room temperature. After stirring overnight, the reaction mixture was partitioned water and hexane. The resulting mixture was extracted with 2×100 mL of EtOAc. The organic phase was dried, concentrated and purified on a silica gel column (50% EtOAc/hexane) to provide g (55%) of desired product. Rf=0.30 (1:1 Hexane:EtOAc), $^1$H NMR (CDCl3, 400 MHz) 9.98 (s, 2H), 8.46 (s, 1H), 8.34 (s, 2H0, 8.229 s, 1H), 7.78 (d, 2H), 7.70 (d, 2H), 7.49 (s, 1H), 7.32–7.41 (m, 9H) Found: C, 61.78; H, 3.76; N, 7.68.

Exemplary Compound 17 was prepared as shown in Scheme I-D, below.

Scheme I-D

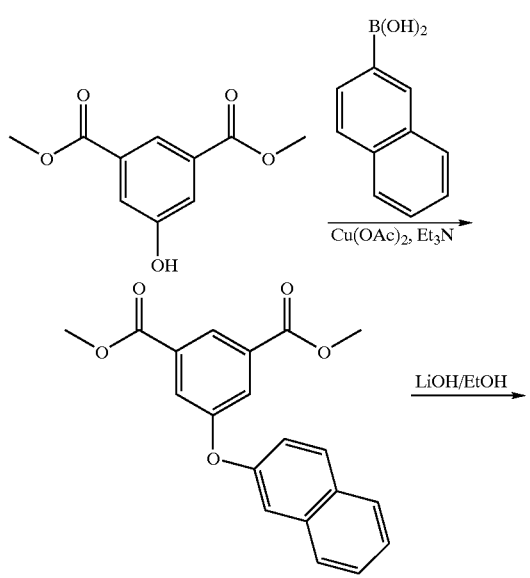

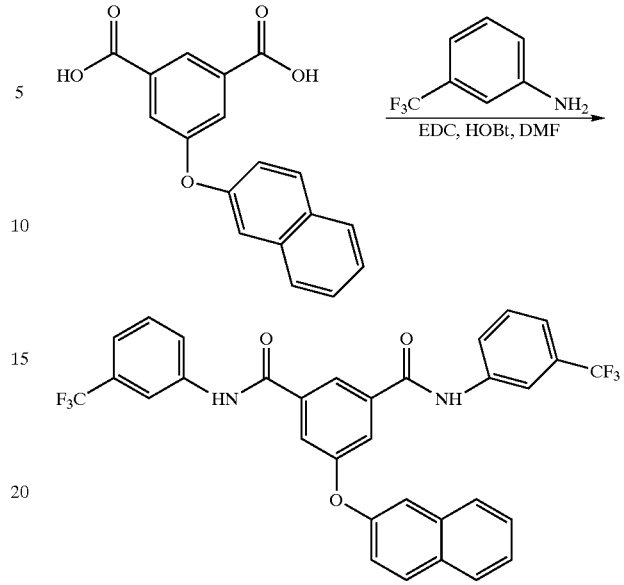

Synthesis of (5-(2-naphthyloxy)-3-{N-[3-(trifluoromethyl) phenyl]carbamoyl}phenyl)-N-[3-(trifluoromethyl)phenyl] formamide (Exemplary Compound 17)

5-(naphthalene-2-yloxy)-isophthalic acid dimethylester. A solution of 5-hydroxyisophthalic acid dimethylester (208 mg, 1 mmol) and 2 naphthaleneboronic acid (172 mg, 1 mmol), Cu (OAc)$_2$ (61 mg, 0.5 mmol), Et$_3$N (0.16 ml, 1.2 mmol) in 10 ml methylenechloride was refluxed for overnight. The reaction mixture was purified by silica gel column eluted by 15% Teac in hexane to afford the product (76% yield).

$^1$H NMR (Acetone-d6, 400 MHz) 8.25 (s, 1H), 8.05 (d, 1H), 7.97 (d, 1H), 7.89 (d, 1H), 7.73 (s, 2H), 7.54 (t, 1H), 7.51 (t, 1H), 7.37 (d, 1H), 4.01 (s, 6H).

5-(naphthalene-2-yloxy)-isophthalic acid. A solution of LiOH (1.5 mmol) in water (1 ml) was added to 5-(naphthalene-2-yloxy)-isophthalic acid dimethylester (0.5 mmol) suspended in 5 ml EtOH. The mixture was stirred at room temperature. The reaction was monitored by TLC until completion. 2.5 ml 1 M HCl solution was added and the precipitation was collected. The product was used in next step without further purification.

(5-(2-naphthyloxy)-3-{N-[3-(trifluoromethyl)phenyl] carbamoyl}phenyl)-N-[3-(trifluoromethyl)phenyl] formamide (Exemplary Compound 17). A solution of EDC (287 mg, 1.5 mmol) in 5 ml DMF was slowly added to a mixture solution containing 5-(naphthalene-2-yloxy)-isophthalic acid, HOBt (135 mg, 1 mmol), and 3-trifluromethylaniline (161 mg, 1 mmol) in 10 ml DMF at room temperature. After stirring overnight, the reaction mixture was partitioned water and hexane. The resulting mixture was extracted with 2×100 mL of EtOAc. The organic phase was dried, concentrated and purified on a silica gel column (20% EtOAc/hexane) to provide g (55%) of desired product. Rf=0.70 (4:1 Hex:EtAc). $^1$H NMR (Acetone-d6, 400 MHz) 9.87 (s, 2H, NH), 8.28 (s, 1H), 8.149 s, 2H), 7.93 (d, 2H), 7.84 (d, 1H), 7.80 (s, 2H), 7.76 (s, 1H), 7.70 (d, 1H), 7.48 (t, 2H), 7.40 (t, 1H), 7.36 (t, 1H0, 7.309 d, 2H), 7.229 d, 1H). Found: C, 64.88; H, 3.57; N, 4.68.

Exemplary Compound 18 was prepared according to Scheme I-E, below.

Synthesis of (5-(2-naphthyl)-3-{N-[3-(trifluoromethyl)phenyl]carbamoyl}phenyl)-N-[3-(trifluoromethyl)phenyl]formamide (Exemplary Compound 18)

5-(naphthalene-2-yl)-isophthalic acid dimethylester. A solution of 5-bromoisophthalic acid dimethylester (544 mg, 2 mmol), 2-naphthaleneboronic acid (342 mg, 2 mmol), Pd(OAc)$_2$ (8 mg), tri-o-tolylphosphine (30 mg) and 5 ml Et$_3$N (5 ml) in 10 ml DMF was stirred at 100° C. for overnight The reaction mixture was purified by silica gel column eluted by 20% EtAc in hexane to afford the product (75% yield). $^1$H NMR (Acetone-d6, 400 MHz), 8.55 (s, 1H), 8.45 (s, 2H), 8.17 (d, 1H), 7.91 (d, 1H), 7.88 (d, 1H), 7.77 (t, 1H), 7.67 (t, 1H), 7.38 (m, 2H), 4.03 (s, 6H).

Scheme I-E

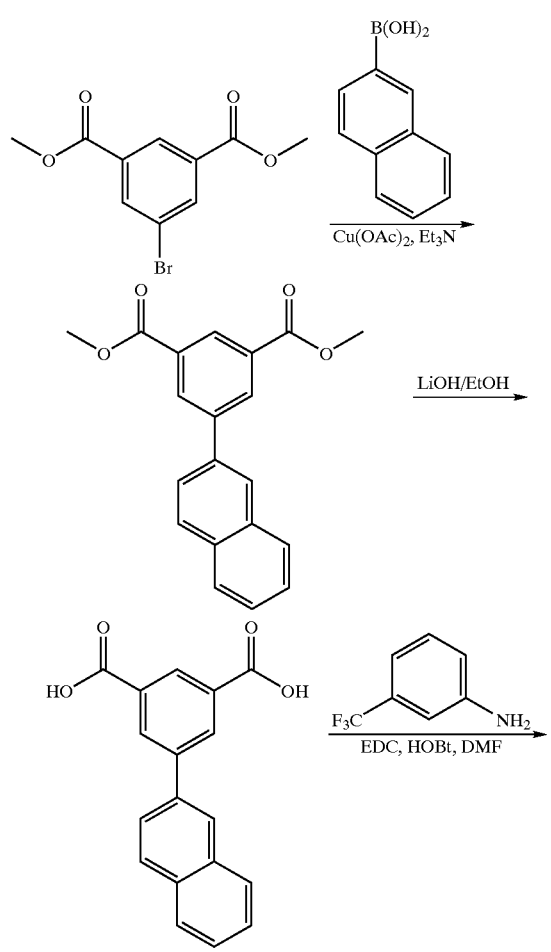

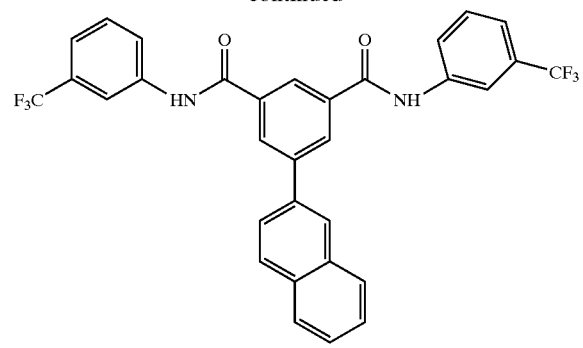

5-(naphthalene-2-yl)-isophthalic acid. A solution of LiOH (1.5 mmol) in water (1 ml) was added to 5-(naphthalene-2-yl)-isophthalic acid dimethylester (160 mg, 0.5 mmol) suspended in 5 ml EtOH. The mixture was stirred at room temperature. The reaction was monitored by TLC until completion. 1.5 ml 1 M HCl solution was added and the precipitation was collected. The product was used in next step without further purification (5-(2-naphthyl)-3-{N-[3-(trifluoromethyl)phenyl]carbamoyl}phenyl)-N-[3-(trifluoromethyl)phenyl]formamide (Exemplary Compound 18). A solution of EDC (287 mg, 1.5 mmol) in 5 ml DMF was slowly added to a mixture solution containing the product from previous step (0.5 mmol), HOBt (135 mg, 1 mmol), and 3-trifluromethylaniline (161 mg, 1 mmol) in 10 ml DMF at room temperature. After stirring overnight, the reaction mixture was partitioned water and ethylacetate. The resulting mixture was extracted with 2×100 mL of EtOAc. The organic phase was dried, concentrated and purified on a silica gel column (50% EtOAc/hexane) to provide g (55%) of desired product as white solid. Rf=0.40 (3:1 Hex. EtOAc), $^1$H NMR (Acetone-d6, 400 MHz) 10.35 (s, NH, 2H), 8.63 (s, 2H), 8.57 (s, 1H), 8.45 (m, 3H), 8.15 (d, 1H), 8.10 (d, 1H), 8.03 (d, 1H), 7.65 (d, 1H), 7.61 (t, 1H), 7.56 (t, 1H), 7.52 (d, 2). Found: C, 66.86; H, 3.64; N, 4.97.

Compounds 23–25 were prepared according to Scheme I-F, below.

Synthesis of (5-(2-(2-naphthyl)vinyl)-3-{N-[3-(trifluoromethyl)phenyl]carbamoyl}phenyl)-N-[3-(trifluoromethyl)phenyl]formamide (Exemplary Compound 25)

Scheme I-F

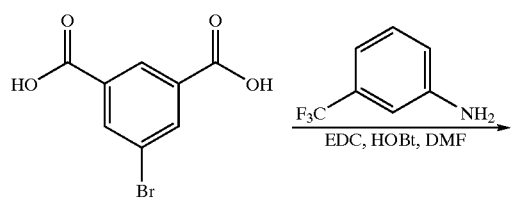

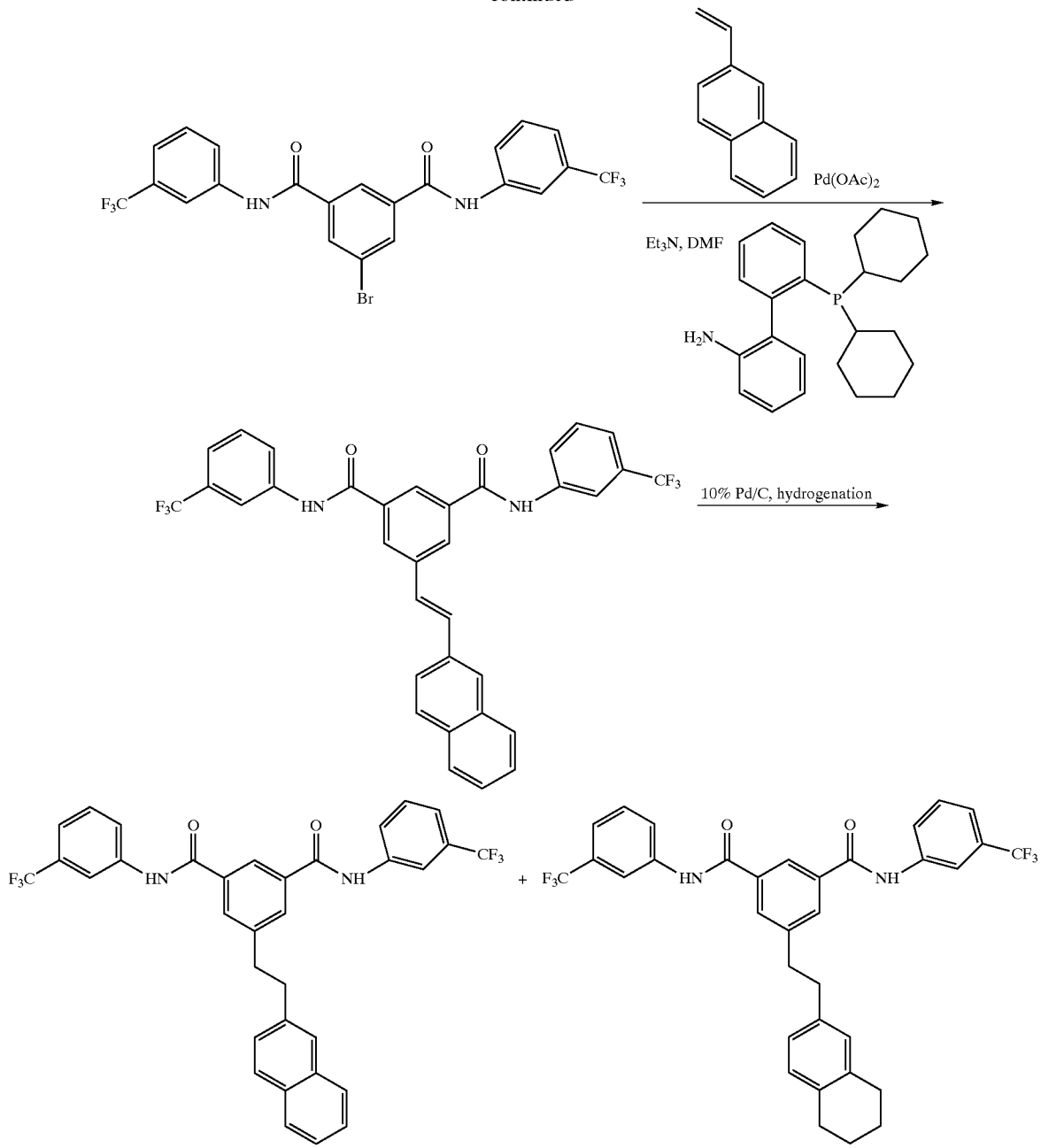

(3-bromo-5-{N-[3-(trifluoromethyl)phenyl]carbamoy}phenyl)-N-[3-(trifluoromethyl) phenyl]formamide A solution of EDC (573 mg, 3 mmol) in 5 ml DMF was slowly added to a mixture of 5-bromoisophthalic acid (245 mg, 1 mmol), HOBt (270 mg, 2 mmol), and 3-trifluromethylaniline (322 mg, 2 mmol) in 15 ml DMF at room temperature. After stirring overnight, the reaction mixture was partitioned water and ethyl acetate. The resulting mixture was extracted with 2×100 mL of ethyl acetate and organic phase was dried, concentrated and purified on a silica gel column (20% hexane/hexane) to provide 975 mg (92%) of desired product as white solid. $R_f$=0.50 (5:1 Hex:EtAc). $^1$H NMR (DMSO-d6+D20, 400 MHz) 10.6 (s, 2H, NH), 8.64 (s, 1H), 8.819 s, 2H), 8.53 (s, 2H), 8.22 (d, 2H), 7.76 (t, 2H), 7.62 (d, 2H). Found: C, 49.56; H, 2.40; N, 5.29.

(5-(2-(2-naphthyl)vinyl)-3-{N-[3-(trifluoromethyl)phenyl]carbamoyl}phenyl)-N-[3-(trifluoromethyl)phenyl]formamide (Exemplary Compound 25). A solution of (3-bromo-5-{N-[3-(trifluoromethyl)phenyl]carbamoyl}phenyl)-N-[3-(trifluoromethyl)phenyl]formamide (265 mg, 0.5 mmol) and 2-vinylnaphthalene (0.5 mmol), Pd(OAc)$_2$ (7 mg), 2-dicyclohexylphophino-2'-(N,N-dimethylaminobiphenyl (30 mg), and Et$_3$N (5 ml) in 10 ml DMF was heated at 100° C. for overnight. The mixture then was poured to water and the precipitation was collected and recystalized from methylenchloride to afford white solid product (76% yield). Rf=0.60 (6:1 Hex:EtOAc). $^1$H NMR (DMSO-d6, 400 MHz) 10.81 (s, 2H, NH), 8.5 (s, 3H), 8.28 (s, 2H), 8.15 (d, 2H), 8.12 (s, 1H), 7.979 s, 2H), 7.93 (t, 2H), 7.64 (m, 4H), 7.529 m, 4H)C, 65.22; H, 3.93; N, 4.47. Found: C, 65.20; H, 3.67; N, 4.73.

Synthesis of (5-(2-(2-naphthyl)ethyl)-3-{N-[3-(trifluoromethyl)phenyl]carbamoyl}phenyl)-N-[3-(trifluoromethyl)-phenyl]formamide (Exemplary Compound 24) and (5-(2-(2-5,6,7,8-tetrahydronaphthyl)ethyl)-3-{N-[3-(trifluoromethyl)phenyl]carbamoyl}phenyl)-N-[3-(trifluoromethyl)phenyl]formamide (Exemplary Compound 23)

A solution of 5-(2-(2-naphthyl)vinyl)-3-{N-[3-(trifluoromethyl) phenyl]carbamoyl}phenyl)-N-[3-(trifluoromethyl)phenyl]formamide (Exemplary Compound 25) (200 mg) and catalytic amount of 10% Pd/C in 20 ml EtOH was subjected to hydrogenation with 50 psi overnight. After filtering the catalyst and concentrating the solvent, the residue was purified by silica gel to afford both the titled compounds as white solids (total yield 97%).

Exemplary Compound 24: $^1$H NMR (DMSO-d6, 400 MHz) 9.88 (s, 2H, NH), 8.30 (s, 1H), 8.19 (s, 2H), 8.06 (s, 2H), 7.94 (d, 2H), 7.71 (d, 2H), 7.69 (d, 1H), 7.61 (s, 1H), 7.53 (t, 2H), 7.35 (m, 4H), 3.11 (s, 4H). Found: C, 67.04; H, 4.06; N, 4.60. Exemplary Compound 23: $^1$H NMR (DMSO-d6, 400 MHz) 10.04 (s, 2H, NH), 8.499 s, 1H), 8.38 (s, 2H), 8.13 (m, 4H), 7.65 (t, 2H), 7.55 (d, 2H), 7.11 (s, 1H), 7.01 (d, 2H), 3.18 (t, 2H), 3.03 (t, 2H), 2.75 (m, 4H), 1.84 (m, 4H). Found: C, 66.50, H, 4.81; N, 4.49.

Exemplary Compounds 37 and 38 were prepared according to Scheme I-G, below.

Scheme I-G

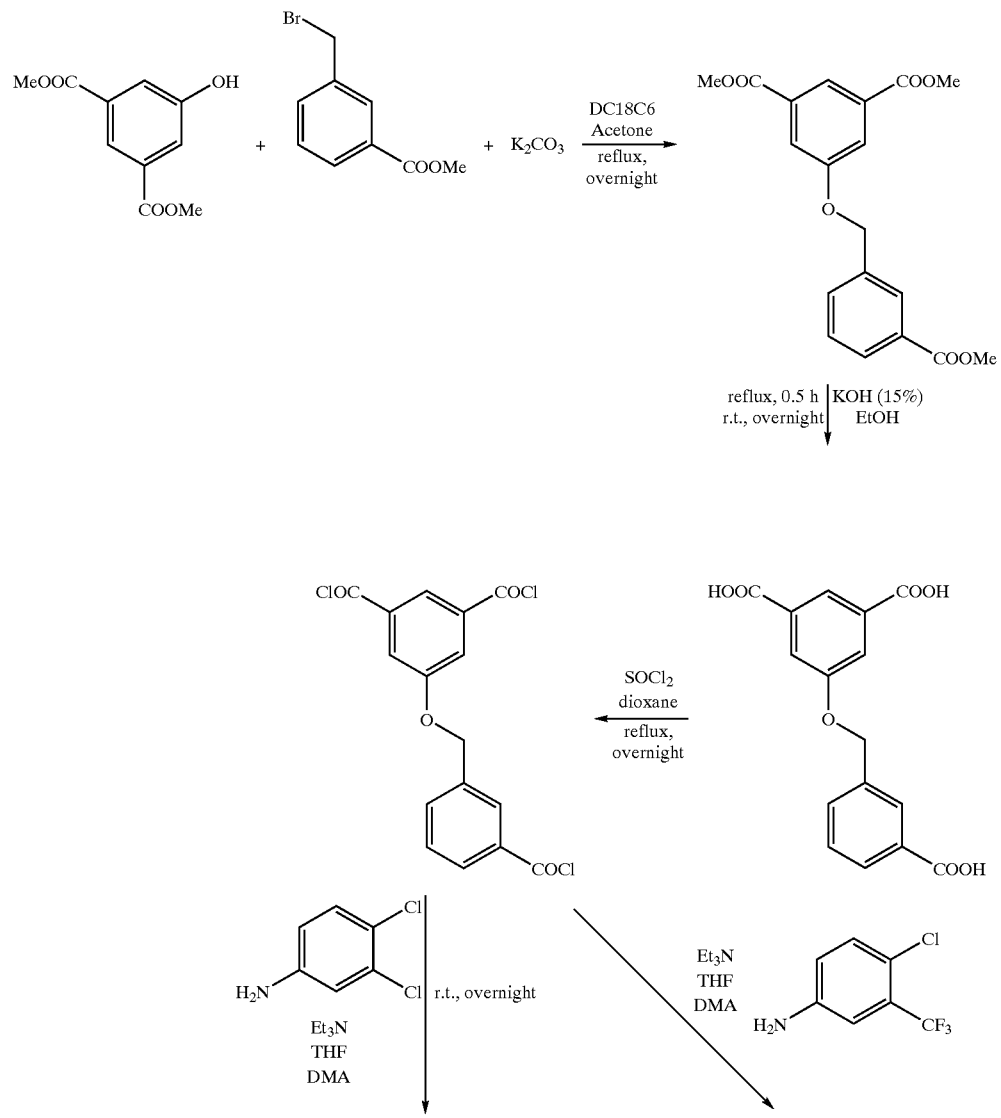

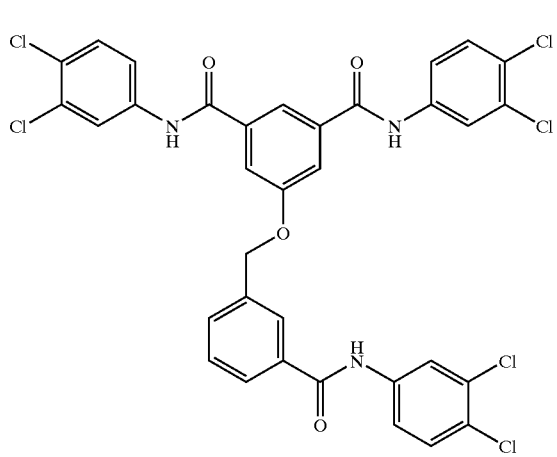
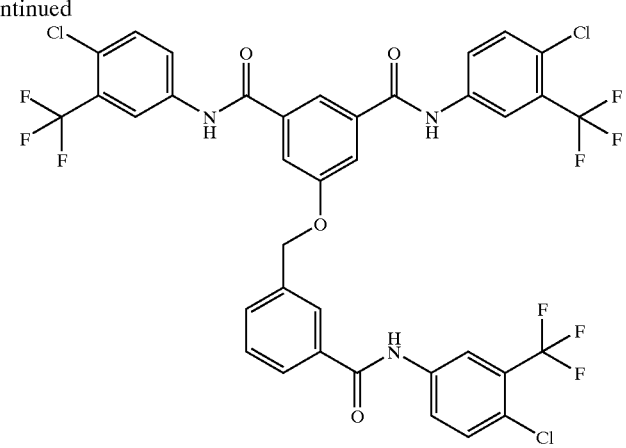

Dimethyl 5-[3-(methoxycarbonyl)benzyloxy]isophthalate. A mixture of 5-hydroxyisophthalic acid dimethyl ester (3.47 g, 16.5 mmol), 3-bromomethylbenzoic acid methyl ester (3.44 g, 15 mmol), potassium carbonate (3.11 g, 22.5 mmol), and dicyclohexano-18-crown-6 (50 mg) in acetone (150 mL) was stirred and refluxed overnight, cooled to room temperature, and poured on ice-water (200 g). Precipitate formed was filtered, washed with water (5×50 mL), and air-dried to give 6.36 g (100%) of the triester: $^1$H NMR (DMSO-d$_6$, 400 MHz), δ: 8.09 (d, J=7.0 Hz, 2H); 7.94 (d, J=8.0 Hz, 1H); 7.83–7.76 (m, 3H); 7.58 (t, J=7.5 Hz, 1H); 5.35 (s, 2H); 3.89 (s, 6H); 3.87 (s, 3H).

5-[3-(Carboxy)benzyloxy]isophthalic acid. A suspension of dimethyl 5-[3-(methoxycarbonyl)benzyloxy]isophthalate (6.36 g, 16.5 mmol) in the mixture of KOH (15% aq., 45 mL) and EtOH (100 mL) was refluxed for 0.5 h, then cooled to room temperature and stirred overnight. The formed solution was extracted with dichloromethane (50 mL). The aqueous layer was separated, acidified with HCl conc. (to pH 2), and bulky precipitate formed was filtered and air-dried. White microcrystals; yield 4.71 g (97%).

5-[3-(Carboxy)benzyloxy]isophthalic acid trichloride. To a stirred suspension of 5-[3-(carboxy)benzyloxy]isophthalic acid (4.71 g, 14.9 mmol) in dioxane (50 mL) SOCl$_2$ (4.34 mL, 59.4 mmol) was added in one portion. The whole was stirred and refluxed overnight. Resulting clear solution was cooled to room temperature, little solid formed was filtered off, and filtrate concentrated in vacuo to give 5.25 g (95%) of cream-white solid, which was used immediately for the syntheses of Compounds 37 and 38 by the method of Scheme I.

EXAMPLE 2

Synthesis of Exemplary Compounds 6, 9, 10, 11, 12, 13, 14, 27, 31, 35, 36, 39, 40 and 44

Exemplary Compounds 6, 9, 10, 11, 12, 13, 14, 27, 31, 35, 36, 39, 40 and 44 were prepared from the appropriately substituted 1,3-dinitro aromatic precursors, as shown in Scheme II, below.

Synthesis of N-(5-[(1,3-dioxoisoindolin-2-yl)methyl]-3-{[3-(trifluoromethyl) phenyl]carbonyl-amino}phenyl)[3-(trifluoromethyl)phenyl]formamide (Exemplary Compound 12)

Scheme II

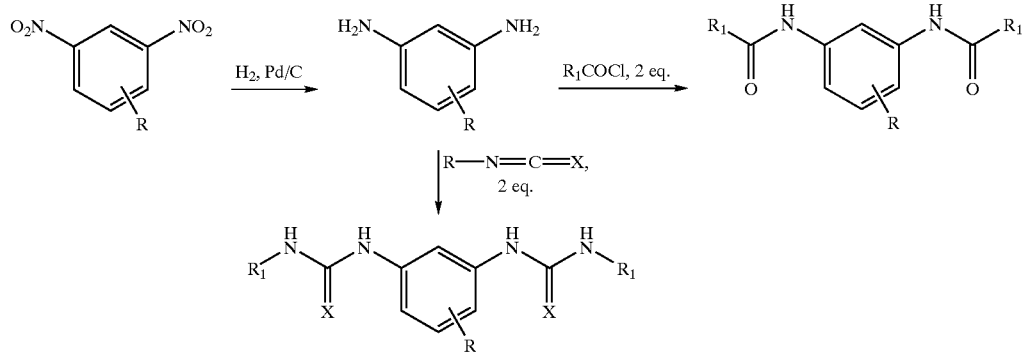

2-[(3,5-dinitrophenyl)methyl]isoindoline-1,3-dione. A solution of 3,5-dinitrobenzyl chloride (2.2 g, 10 mmol) in DMA (40 mL) was treated with potassium phthalimide (1.9 g, 10 mmol) and the mixture stirred 12 h. The mixture was then concentrated and the solid residue washed with ethyl acetate, dried, washed with water and dried to give 2.5 g (76%) of essentially pure adduct as a white solid: $^1$H NMR 400 MHz (DMSO) δ5.06 (s, 2H); 7.82–7.97 (m, 4H); 8.62 (s, 2H); 8.74 (s, 1H).

N-(5-[(1,3-dioxoisoindolin-2-yl)methyl]-3-{[3-(trifluoromethyl)phenyl]carbonylamino}phenyl)[3-(trifluoromethyl)phenyl]formamide (Exemplary Compound 12). A solution of 2-[(3,5-dinitrophenyl)methyl]isoindoline-1,3-dione (1.5 g, 4.6 mmol) in CH$_2$Cl$_2$ (25 mL) was treated with 10% palladium/carbon (300 mg) and the mixture shaken 1 h. under 50 psi H$_2$. The mixture was filtered and the filtrate treated with triethylamine (1.0 g, 10 mmol) followed by 3-trifluoromethylbenzoyl chloride (2.0 g, 9.6 mmol) and stirred 12 h. The reaction mixture was then concentrated and the product purified on silica using 1:1 hexane:ethyl acetate as eluent to give 2.1 g (75%) of the compound of Example 12 as a white solid: $^1$H NMR 400 MHz (DMSO) δ4.80 (s, 2H); 7.49 (s, 2H); 7.78 (t, J=8.0Hz, 2H); 7.86–7.91 (m, 2H); 7.92–8.00 (m, 4H); 8.26 (d, J=8.0Hz, 2H); 8.29 (s, 2H); 8.38 (s, 1H); 10.56 (s, 2H). Anal. Calcd for C$_{31}$H$_{19}$N$_3$O$_4$F$_6$: C, 60.89; H, 3.13; N, 6.87. Found: C, 60.84; H, 3.00; N, 6.91.

In a similar manner were prepared the following compounds:

[(3,5-dichlorophenyl)amino]{[5-({[(3,5-dichlorophenyl)amino]thioxomethyl}amino)-2-{[4-(dimethylamino)phenyl]amino}phenyl]amino}methane-1-thione (Exemplary Compound 35). $^1$H NMR 400 MHz (DMSO) δ2.85 (s, 6H); 6.73 (d, 2H, J=8); 6.94–6.98 (m, 3H); 7.06–7.08 (m, 2H); 7.28 (dt, 2H, J=2,4); 7.43 (s, 1H); 7.53 (s, 2H); 7.58 (s, 2H); 9.50 (s, 1H); 9.57 (s, 1H); 9.83 (s, 1H); 10.01 (s, 1H). Anal. Calcd for C$_{28}$H$_{24}$N$_6$S$_2$Cl$_4$ (0.25EtOAc): C, 51.79; H, 3.90; N, 12.50; S, 9.54. Found: C, 51.70; H, 4.02; N, 12.16; S, 9.37.

2-{[3,5-bis({[(3,5-dichlorophenyl)amino]thioxomethyl}amino)phenyl]methyl}iso-indoline-1,3-dione (Exemplary Compound 27). $^1$H NMR 400 MHz (DMSO) δ4.76 (s, 2H); 7.16 (s, 2H); 7.30 (s, 2H); 7.54 (s, 4H); 7.65 (s, 1H); 7.85–7.95 (m, 4H); 9.91 (s, 2H); 10.20 (s, 2H). Anal. Calcd for C$_{29}$H$_{19}$N$_5$S$_2$Cl$_4$O$_2$ (1.0H$_2$O): C, 50.23; H, 3.05; N, 10.10; S, 9.25. Found: C, 49.90; H, 3.08; N, 10.04; S, 9.31.

2-{[3-amino-5-({[(3,5-dichlorophenyl)amino]thioxomethyl}amino)phenyl]methyl}isoindoline-1,3-dione (Exemplary Compound 31). $^1$H NMR 400 MHz (DMSO) δ4.60 (s, 2H); 5.25 (s, 2H); 6.31 (s, 1H); 6.44 (s, 1H); 6.57 (s, 1H); 7.28 (s, 2H); 7.58 (s, 2H); 7.83–7.91 (m, 4H); 9.75 (s, 1H); 9.94 (s, 1H). Anal. Calcd for C$_{22}$H$_{16}$N$_4$S$_1$Cl$_2$O$_2$: C, 56.06; H, 3.42; N, 11.89; S, 6.80; Cl, 15.04. Found: C, 55.78; H, 3.55; N, 11.74; S, 6.76; Cl, 15.30.

1,3-(3,5-Dichlorophenyl)-N-[5-(3,4-dichlorophenoxymethyl)-phenyl]amide (Exemplary Compound 6). $^1$H NMR (DMSO-d6, 400 MHz) 5.19 (s, 2H); 7.06 (q, 1H); 7.35 (d, 1H); 7.55 (d, 1H); 7.61 (d, 2H); 7.89 (t, 2H); 8.00 (d, 4H); 8.32 (t, 1H); 10.56 (s, 2H). Anal: Calcd for: C, 51.54; H, 2.56; N, 4.45. Found: C, 51.28; H, 2.74; N, 4.35.

Amino-substituted dinitro aryl compounds were prepared from the corresponding dinitro aryl anilines by copper catalyzed coupling with aryl boronoc acids (Scheme II-A), or from the corresponding dinitro aryl halides via palladium-catalyzed coupling with aryl halides (Scheme II-B). In either case, the obtained substituted aryl dinitro intermediates were reduced to the corresponding diamines which were converted to the final products as described for Scheme I.

Scheme II-A

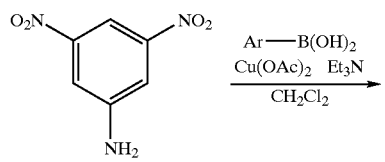

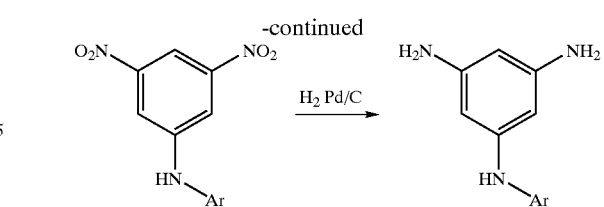

Synthesis of [(3,5-dichlorophenyl)amino]{[3-({[(3,5-dichlorophenyl)amino]thioxomethyl}amino)-5-[(4-bromophenyl)amino]phenyl]amino}methane-1-thione (Exemplary Compound 11)

(3,5-dinitrophenyl)(4-bromophenyl)amine. To a stirred mixture of dinitroaniline (1.3 g, 7.1 mmol), copper acetate (1.29 g, 7.1 mmol) and triethylamine (2.2 g, 21 mmol) in CH$_2$Cl$_2$ (50 mL) was added 4-bromophenylboronic acid (5.8 g, 21 mmol) in 1 g portions over 4 h. and the mixture then stirred overnight. The reaction mixture was then concentrated and the product purified on silica gel using 3:1 hexane:ethyl acetate as eluent to give 0.80 g (33%) of the amino-substituted aromatic compound as an orange solid: Low resolution MS Calcd for C$_{12}$H$_8$N$_3$O$_4$Br: 338. Found: 338.

(3,5-diaminophenyl)(4-bromophenyl)amine. To a solution of (3,5-dinitrophenyl)(4-bromophenyl)amine (0.34 g, 1.0 mmol) in ethanol (10 mL) was added indium (2.0 g, 17 mmol) followed by saturated ammonium chloride solution (3 mL) and the mixture stirred 12 h. At this time, TLC showed the reaction complete. The reaction mixture was then filtered through celite, concentrated and the residue dissolved in 50 mL CH$_2$Cl$_2$. The organic solution was washed with 50 mL water followed by 50 mL brine, dried over magnesium sulfate, filtered and concentrated to give 0.26 g (93%) of a brown oil, R$_f$ 0.1 (1:1 hexane:ethyl acetate), which was carried directly to the next step.

[(3,5-dichlorophenyl)amino]{[3-({[(3,5-dichlorophenyl)amino]thioxomethyl}amino)-5-[(4-bromophenyl)amino]phenyl]amino}methane-1-thione. (Exemplary Compound 11). To a solution of (3,5-diaminophenyl)(4-bromophenyl)amine (0.25 g, 0.90 mmol) in CH$_2$Cl$_2$ (5 mL) was added 3,5-dichlorophenylisothiocyanate (0.39 g, 1.9 mmol) and the mixture stirred overnight. The solid precipitate was filtered, washed with cold CH$_2$Cl$_2$ and dried to give 0.28 g (45%) of the compound of example 11 as a white solid: $^1$H NMR 400 MHz (DMSO) δ6.97 (s, 1H); 7.02 (s, 2H); 7.09 (d, J=8.5 Hz, 2H); 7.31 (s, 2H); 7.35 (d, J=8.5Hz, 2H); 7.57 (s, 4H); 8.54 (s, 1H); 9.92 (s, 2H); 10.20 (s, 2H). Anal. Calcd for C$_{26}$H$_{16}$N$_5$S$_2$Cl$_4$Br$_1$(0.1H$_2$O): C, 45.38; H, 2.67; N, 10.18; S, 9.32. Found: C, 44.99; H, 2.68; N, 9.97; S, 9.31.

The Exemplary Compounds 36, 39, 40, and 44 were prepared by this method:

Exemplary Compound 36: [(3,5-dichlorophenyl)amino]{[3-({[(3,5-dichlorophenyl)amino]thioxo-methyl}amino)-4-[(4-chlorophenyl)amino]phenyl]amino}methane-1-thione: $^1$H NMR (CDCl3, 400 MHz) 8.28 (br, NH, 1H), 8.21 (br, NH, 2H), 7.89 (br, NH, 1H), 7.72 (s, 1H), 7.36 (s, 2H), 7.12–7.21 (m, 7H), 7.01 (d, 1H), 6.84 (d, 2H), 6.0 (s, 1H). Anal: Calcd for: C, 48.65; H, 2.83; N, 10.91; S, 9.99; Cl, 27.62. Found: C, 48.91; H, 3.11; N, 10.43; S, 9.24; Cl, 27.01.

Exemplary Compound 39: [(3,5-dichlorophenyl)amino]{[3-({[(3,5-dichlorophenyl) amino]thioxo-methyl}amino)-4-(3,5-dimethylpyrazolyl)phenyl]amino}methane-1-thione 1H NMR (CDCl3, 400 MHz) 9.65 (s, NH, 1H), 8.72 (s, NH, 1H), 8.42 (s, NH, 1H), 8.26 (s, NH, 1H), 7.53 (s, 2H), 7.27 (d, 1H), 7.25 (s, 1H), 7.21 (s, $H), 7.09 (d, 1H), 6.97 (s, 1H), 2.25 (s, 3H), 2.12 (s, 3H). Anal: Calcd for: C, 48.34; H, 3.44; N, 13.53; S, 10.32. Found: C, 48.40; H, 3.44; N, 13.77; S, 10.41.

Exemplary Compound 40: [(3,5-dichlorophenyl)amino]{[3-({[(3,5-dichlorophenyl) amino]thioxomethyl}amino)-4-[(4-phenoxyphenyl)amino]phenyl]amino}methane-1-thione $^1$H NMR (CDCl3, 400 MHz) 8.24 (s, NH, 1H), 8.15 (s, NH, 1H), 8.10 (s, NH, 1H), 7.93 (s, NH, 1H), 7.56 (d, 1H), 7.38 (d, 2H), 7.26–7.36 (m, 5H), 7.21 (d, 2H), 7.11 (s, 1H, 7.05 (d, 1H), 7.02 (s, 1H), 6.97 (s, 1H), 6.94 (s, 4H), 5.95 (s, NH, 1H). Anal: Calcd for: C, 54.11; H, 3.43; N, 9.86; S, 9.03. Found: C, 54.47; H, 3.67; N, 9.58; S, 8.63.

Exemplary Compound 44: [(3,5-dichlorophenyl)amino]{[5-({[(3,5-dichlorophenyl) amino]thioxomethylamino)-2-piperidylphenyl]amino}methane-1-thione: $^1$H NMR (Acetone-d6, 400 MHz) 9.35 (br, NH, 1H), 9.02 (br, NH, 3H), 7.67 (s, 2H), 7.65 (s, 2H), 7.53 (s, 1H), 7.23 (d, 1H), 7.22 (s, 1H), 7.21 (s, 1H0, 6.93 (d, 1H), 2.06 (m, 4H), 1.97 (m, 6H). Anal: Calcd for: C, 49.50; H, 3.95; N, 11.54; S, 10.57; Cl, 23.38. Found: C, 49.15; H, 3.80; N, 11.75; S, 10.67; Cl, 23.56.

Scheme II-B

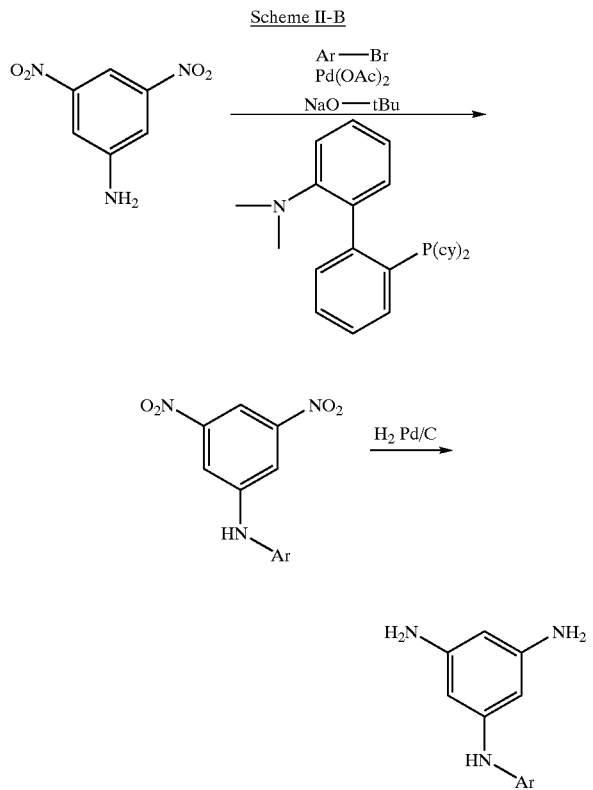

(3,5-dinitrophenyl)-2-pyridylamine. To a mixture of 3,5-dinitroaniline (1.3 g, 7.1 mmol), 2-bromopyridine (1.1 g, 7.1 mmol), palladium acetate (0.13 g, 0.57 mmol) and 2-dicyclohexylphosphino-2'-(N,N-dimethylamino)biphenyl (0.28 g, 0.71 mmol) in toluene (20 mL) was added solid sodium tert-butoxide (0.75 g, 7.8 mmol) and the mixture heated at reflux temperature for 3 d. The reaction mixture was then concentrated and the product purified on silica gel using 2:1 hexane:ethyl acetate as eluent to give 0.30 g (16%) of pyridyl substituted compound as a red solid: Low resolution MS Calcd for $C_{11}H_8N_4O_4$: 260. Found: 260.

[(3,5-dichlorophenyl)amino]{[3-({[3,5-dichlorophenyl)amino]thioxomethyl}amino)-5-(2-pyridylamino)phenyl]amino}methane-1-thione (Exemplary Compound 13) (3,5-dinitrophenyl)-2-pyridylamine was reduced to the diamino compound and reacted with two equivalents of 3,5-dichloroisothiocyanate, as described previously, to yield the Exemplary Compound 13: $^1$H NMR 400 MHz (DMSO) δ6.73–6.79 (m, 1H); 6.89 (d, J=8.4 Hz, 1H); 7.11 (s, 1H); 7.30 (s, 2H); 7.53–7.69 (m, 7H); 8.11 (d, J=3.9 Hz, 1H); 9.24 (s, 1H); 9.83 (s, 2H); 10.24 (s, 2H). Anal. Calcd for $C_{25}H_{18}N_6S_2Cl_4$; C, 49.35; H, 2.98; N, 13.81; S, 10.54; Cl, 23.31. Found: C, 49.34; H, 3.19; N, 13.88; S, 10.30; Cl, 23.30.

Sequential reaction of the diamino aryl Intermediate with 3,5-dichlorobenzoyl Chloride followed by 3,5-dichloroisothiocyanate Provided Exemplary Compound 10

Synthesis of (3,5-dichlorophenyl)-N-[5-({[(3,5-dichlorophenyl)amino]thioxomethyl}amino)-3-{[3-(trifluoromethyl)phenyl]amino }phenyl]formamide (Exemplary Compound 10)

N-(3-amino-5-{[3-(trifluoromethyl)phenyl]amino}phenyl)(3,5-dichlorophenyl) formamide. A solution of (3,5-dinitrophenyl)[3-(trifluoromethyl) phenyl]amine, prepared as previously described via boronic acid coupling (0.50 g, 1.5 mmol) in CH$_2$Cl$_2$ (7 mL) was treated with 10% palladium/carbon (100 mg) and the mixture shaken 1 h. under 50 psi H$_2$. The solution was filtered and the filtrate treated with triethylamine (0.15 g, 1.5 mmol) followed by 3,5-dichlorobenzoyl chloride (0.29 g, 1.4 mmol) and stirred overnight. The reaction mixture was then concentrated and the product purified on silica gel using 2:1 hexane:ethyl acetate as eluent to give 0.54 g (80%) of the desired product as a white solid: $^1$H NMR 400 MHz (DMSO) δ5.17 (s, 2H); 6.16 (s, 1H); 6.69 (s, 1H); 6.82 (s, 1H); 7.05 (t, J=8 Hz, 1H); 7.26–7.44 (m, 4H); 7.94 (s, 2H); 8.30 (s, 1H); 10.08 (s, 1H);

(3,5-dichlorophenyl)-N-[5-({[(3,5-dichlorophenyl)amino]thioxomethy}amino)-3-{[3-(trifluoromethyl)phenyl]amino}phenyl]formamide (Exemplary Compound 10). To a solution of N-(3-amino-5-{[3-(trifluoromethyl)phenyl]amino}phenyl)(3,5-dichloro-phenyl)formamide (0.54 g, 1.2 mmol), in DMA (10 mL) was added 3,5-dichlorophenylisothiocyanate (0.30 g, 1.5 mmol) and the mixture stirred overnight.

The reaction mixture was then concentrated and the product purified on silica gel using 2:1 hexane:ethyl acetate as eluent to give 0.70 g (89%) of Exemplary Compound. 10 as an off white solid: $^1$H NMR 400 MHz (DMSO) δ7.10–7.16(m, 2H); 7.31–7.34 (m, 1H); 7.35–7.39 (m, 2H); 7.39–7.45 (m, 2H); 7.47 (s, 1H); 7.65 (d, J=2.0 Hz, 2H); 7.87–7.89 (m, 1H); 7.97 (d, J=2.0 Hz, 2H); 8.74 (s, 1H); 10.02(s, 1H); 10.22 (s, 1H); 10.44 (s, 1H). Anal. Calcd for $C_{27}H_{17}N_4S_1Cl_4O_1F_3$: C, 50.33; H, 2.66; N, 8.70; S, 4.98; Cl, 22.01. Found: C, 50.10; H, 2.75; N, 8.60; S, 5.00; Cl, 22.21.

Exemplary Compound 9 was prepared from Exemplary Compound 10 as shown in Scheme II-C:

Scheme II-C

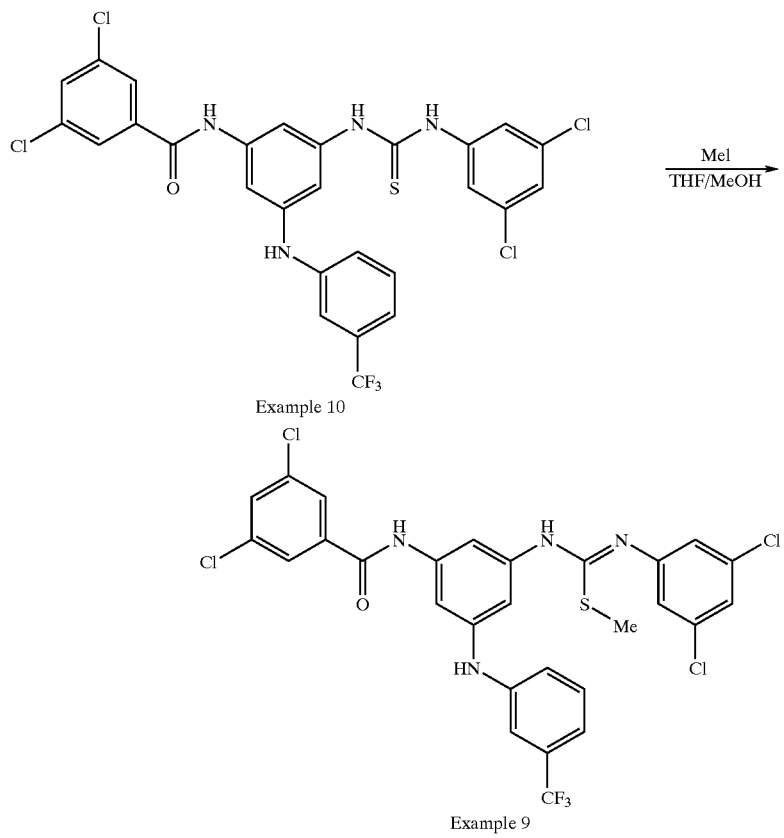

Example 10

Example 9

N-(5-{[2-aza-2-(3,5-dichlorophenyl)-1-methylthiovinyl]amino}-3-{[3-(trifluoromethyl)phenyl]amino}phenyl)(3,5-dichlorophenyl)formamide (Exemplary Compound 9). A solution of Example 10 (0.50 g, 0.78 mmol) in THF (3 mL) was diluted with 7 mL ethanol, treated with iodomethane (0.55 g, 3.9 mmol) and stirred overnight. The reaction mixture was then concentrated and the product purified on silica gel using 3:1 hexane:ethyl acetate as eluent to give 0.43 g (85%) of the Exemplary Compound 9 as a white solid: $^1$H NMR 400 MHz (DMSO) δ2.41–2.47 (m, 3H); 6.88 (s, 2H); 7.06–7.20 (m, 2H); 7.27–7.57 (m, 5H); 7.79 (s, 1H); 7.87 (s, 1H); 7.93–7.99 (m, 2H); 8.62 (s, 1H); 9.03 (s, 1H); 10.34 (s, 1H). Anal. Calcd for $C_{28}H_{19}N_4S_1Cl_4O_1F_3$: C, 51.08; H, 2.91; N, 8.51; S, 4.87; Cl, 21.54. Found: C, 51.21; H, 3.09; N, 8.49; S, 4.73; Cl, 21.60.

Exemplary Compound 14 was prepared from Exemplary Compound 12 as shown in Scheme II-D, below.

Scheme II-D

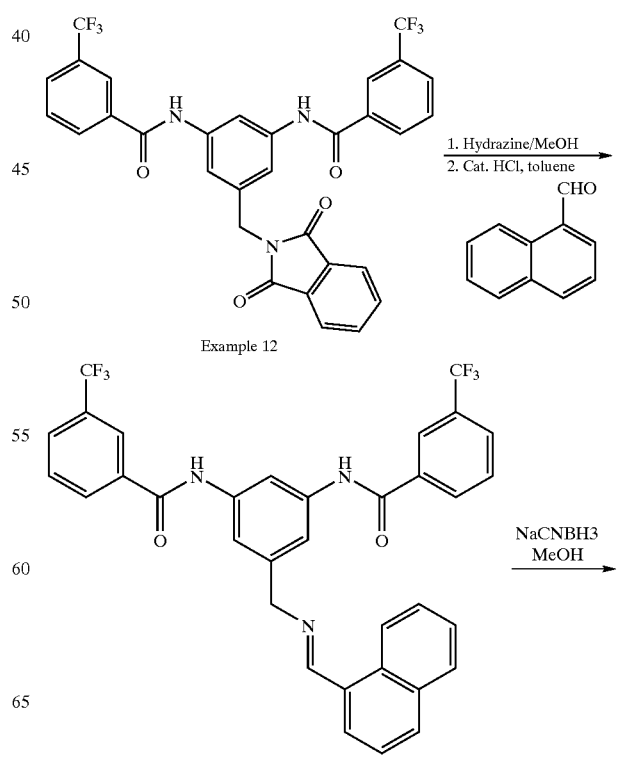

Example 12

-continued

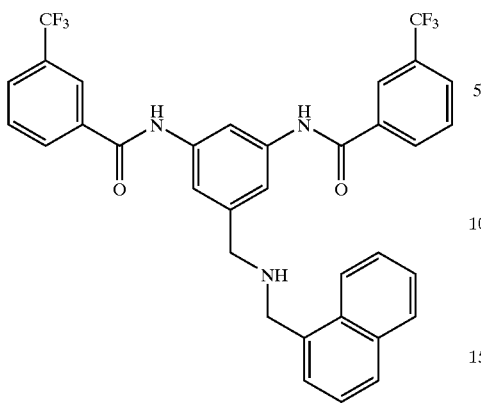

Example 14

N-(5-(2-aza-3-naphthylprop-2-enyl)-3-{[3-(trifluoromethyl)phenyl]carbonylamino}phenyl)[3-(trifluoromethyl)phenyl]formamide. To a solution of Exemplary Compound 12 (2.0 g, 3.3 mmol) in methanol (25 mL) was added hydrazine (1.0 g, 33 mmol) and the mixture heated at reflux temperature overnight. The mixture was then cooled and filtered and the filtrate concentrated to a brown solid residue. The residue was placed in a solution of 1-naphthaldehyde (0.56 g, 3.6 mmol) in 60 mL toluene, heated to 80° C., treated with 3 drops concentrated HCl and then heated at reflux temperature for 12 h using a Dean-Stark trap to collect water evolved from the reaction. The reaction mixture was then concentrated and the product purified by recrystallization in hexane/ethyl acetate to give 0.35 g (18%) of the imine as a light yellow solid: $^1$H NMR 400 MHz (DMSO) δ4.96 (s, 2H); 7.57–7.68 (m, 6H); 7.79 (dd, J=7.5, 8.0 Hz, 1H); 7.97 (d, J=7.5 Hz, 1H); 8.00–8.10 (m, 4H); 8.28 (d, J=8.0 Hz, 1H); 8.30–8.35 (m, 4H); 9.15 (d, J=8.5 Hz, 1H); 9.23 (s, 1H); 10.58(s, 2H). Anal. Calcd for $C_{34}H_{23}N_3O_2F_6$: C, 65.91; H, 3.74; N, 6.78;. Found: C, 65.82; H, 3.91; N, 6.80.

N-(5-{[(naphthylmethyl)amino]methyl}-3-{[3-(trifluoromethyl)phenyl]carbonyl-amino}phenyl)[3-(trifluoromethyl)phenyl]formamide (Exemplary Compound 14) To a solution of the imine from the previous step (40 mg, 0.06 mmol) in ethanol (3 mL) was added sodium cyanoborohydride (10 mg, 0.1 mmol) and the mixture stirred overnight. The reaction mixture was then concentrated and the product purified on silica gel using 2:1 hexane:ethyl acetate as eluent to give 30 mg (75%) of Exemplary Compound 14 as a white solid: $^1$H NMR 400 MHz (DMSO) δ3.78 (s, 2H); 4.19 (s, 2H); 7.26 (s, 1H); 7.34–7.50 (m, 8H); 7.66 (d, J=8.0 Hz, 2H); 7.74 (d, J=8.0 Hz, 1H); 7.83 (d, J=8.0 Hz, 1H); 7.89 (d, J=8.0 Hz, 2H); 8.02 (s, 2H); 8.05 (d, J=8.0 Hz, 1H); 8.53 (s, 2H). Anal. Calcd for $C_{34}H_{25}N_3O_2F_6$: C, 65.70; H, 4.05; N, 6.76; Found: C, 65.79; H, 3.78; N, 6.70.

The intermediate diamine for Exemplary Compound 6 was prepared according to Scheme II-E, below:

Scheme II-E

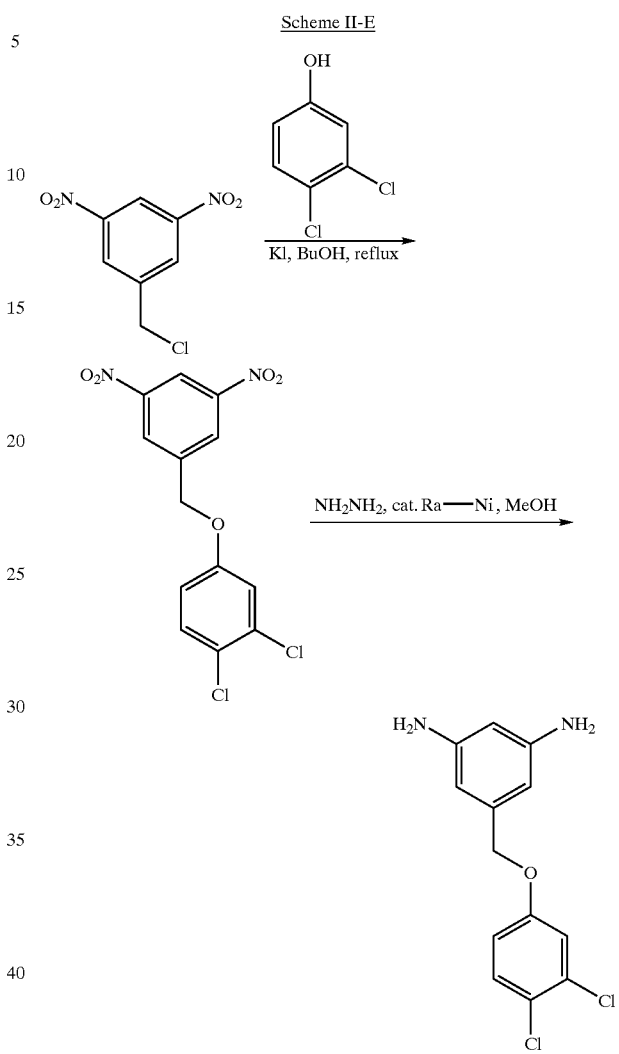

5-(3,4-dichlorophenoxymethyl)-1,3-dinitrobenzene. 0.5 mmole 3,4-Dichloro-phenol and 1 mmole KI were added to a solution of 0.5 mmole 1-Chloromethyl-3,5-dinitrobenzene in 2.5 ml 1-Butanol. The mixture was stirred under reflux overnight. After evaporation the 1-Butanol, the residue was washed with 2×10 ml 1 N HCl and 2×10 ml EtOAc, and dried. $^1$H NMR (DMSO-d6, 400 MHz) 5.44 (s, 2H); 7.14 (d, 1H); 7.43 (s, 1H); 7.58 (d, 1H); 8.73 (s, 2H); 8.81 (s, 1H);

5-(3,4-dichlorophenoxymethyl)benzene-1,3-diamine. 5-(3,4-dichlorophenoxymethyl)-1,3-dinitrobenzene in 5 ml MeOH was added to a solution of 10 ml 2.5 mmole hydrazine monohydrate and catalytic amount of Ra—Ni. The mixture was stirred under reflux for 30 min and then cooled to room temperature. GC-MS gave the peak of reduced product. The solution was filtered through Celite and MeOH was evaporated with rotaevaporation. The residue was used directly for next step without further purification.

EXAMPLE 3

Synthesis of Exemplary Compounds 1, 5, and 4.

Exemplary Compound 1 was synthesized by the method of Scheme III-A, below.
Synthesis of 3-{3,5-Bis-[3-(3,5-dichloro-phenyl)-ureido]-phenyl}-propionic acid methyl ester (Exemplary Compound 1)

filtered. Then, dichlorophenyliso-cyanate (4 mmol) was added to the filtrate and the mixture was stirred overnight at room temperature. The precipitation was collected by filtration and washed twice by methelenchloride. The crude product was recrystalized from acetone to afford pure product (91% yield) as white solid. Rf=0.60 (2:1 Hexane:EtAc); $^1$H NMR (DMSO-d6, 400 MHz) 8.96 (s, 2H), 8.88 (s, 2H), 7.53 (s, 5H), 7.16 (s, 2H), 6.98 (s, 2H), 3.60 (s, 3H), 2.79(t, 2H), 2.62 (t, 2H). Found: C, 50.45; H, 3.67; N, 9.98.

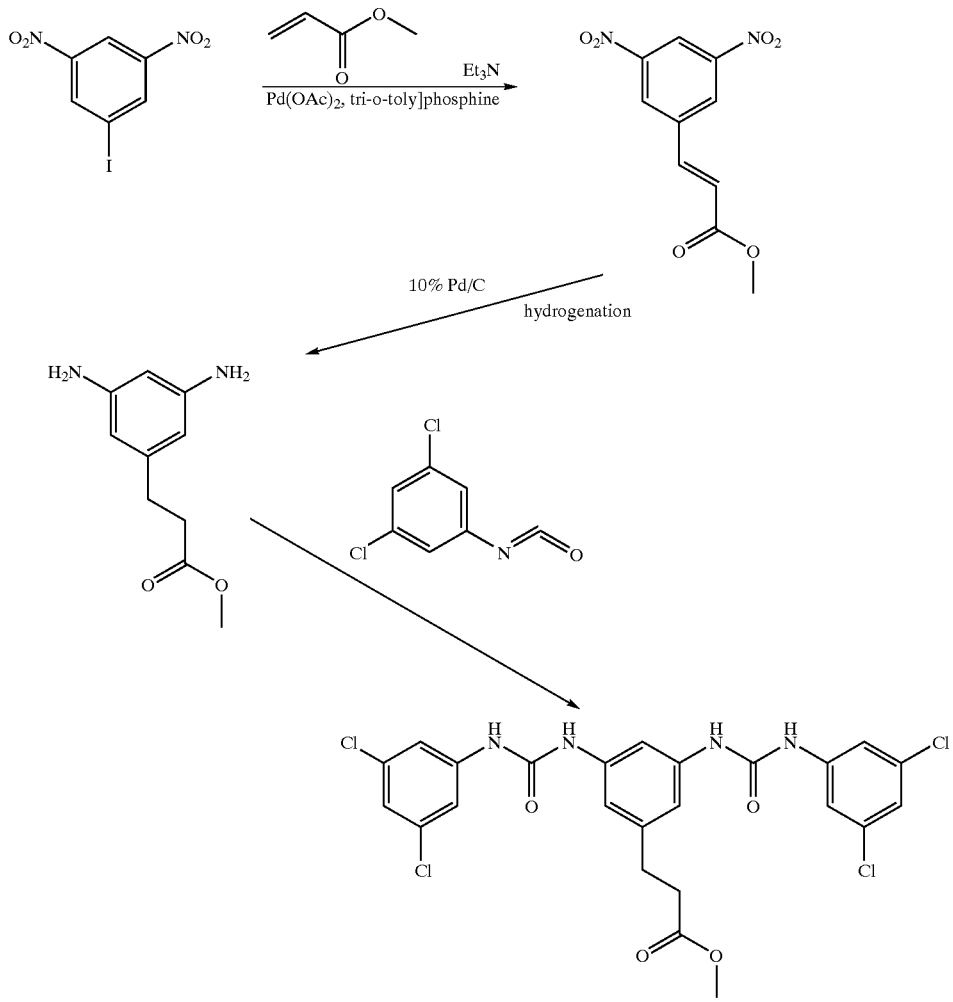

Scheme III-A 3-(3,5-dinitrophenyl)acrylic acid methyl ester. A solution of 5-iododinitrobenzene (10 mmol) and acrylate methylester (50 mmol), Pd(OAc)$_2$ (80 mg), tri-o-tolylphosphine (300 mg) and 30 ml Et$_3$N was stirred at 80° C. for overnight. The reaction mixture was purified by silica gel column eluted by 30% EtAc in hexane to afford the product (56% yield) as white solid. $^1$H NMR (CDCl3, 400 MHz) 9.04 (s, 1H), 8.67 (s, 2H), 7.71 (d, 1H), 6.77 (d, 1H), 3.89 (s, 3H);

3-{3,5-Bis-[3-(3,5-dichlorophenyl)-ureido]-phenyl}propionic acid methyl ester (Exemplary Compound 1). A solution containing 3-(3,5-dinitrophenyl)acrylic acid methyl ester (2 mmol) and catalytic amount of 10% Pd/C in 20 ml methylene chloride was subjected to hydrogenation under 50 psi for 20 minutes. The palladium catalyst was Exemplary Compound 5 was prepared according to Scheme III-B, below: Synthesis of 3-{3,5-Bis-[3-(3,5-dichlorophenyl)ureido]-phenyl}propionic acid methyl ester (Exemplary Compound 5).

3-(3,5-dinitrophenyl) acrylic acid methyl ester. A solution of 5-iododinitrobenzene (10 mmol) and acrylate methylester (50 mmol), Pd(OAc)$_2$ (80 mg), tri-o-tolylphosphine (300 mg) and 30 ml Et$_3$N was stirred at 80° C. for overnight. The reaction mixture was purified by silica gel column eluted by 30% EtAc in hexane to afford the product (56% yield) as white solid. $^1$H NMR (CDCl3, 400 MHz) 9.0 s, 1H), 8.67 (s, 2H), 7.71 (d, 1H), 6.77 (d, 1H), 3.89 (s, 3H);

Scheme III-B

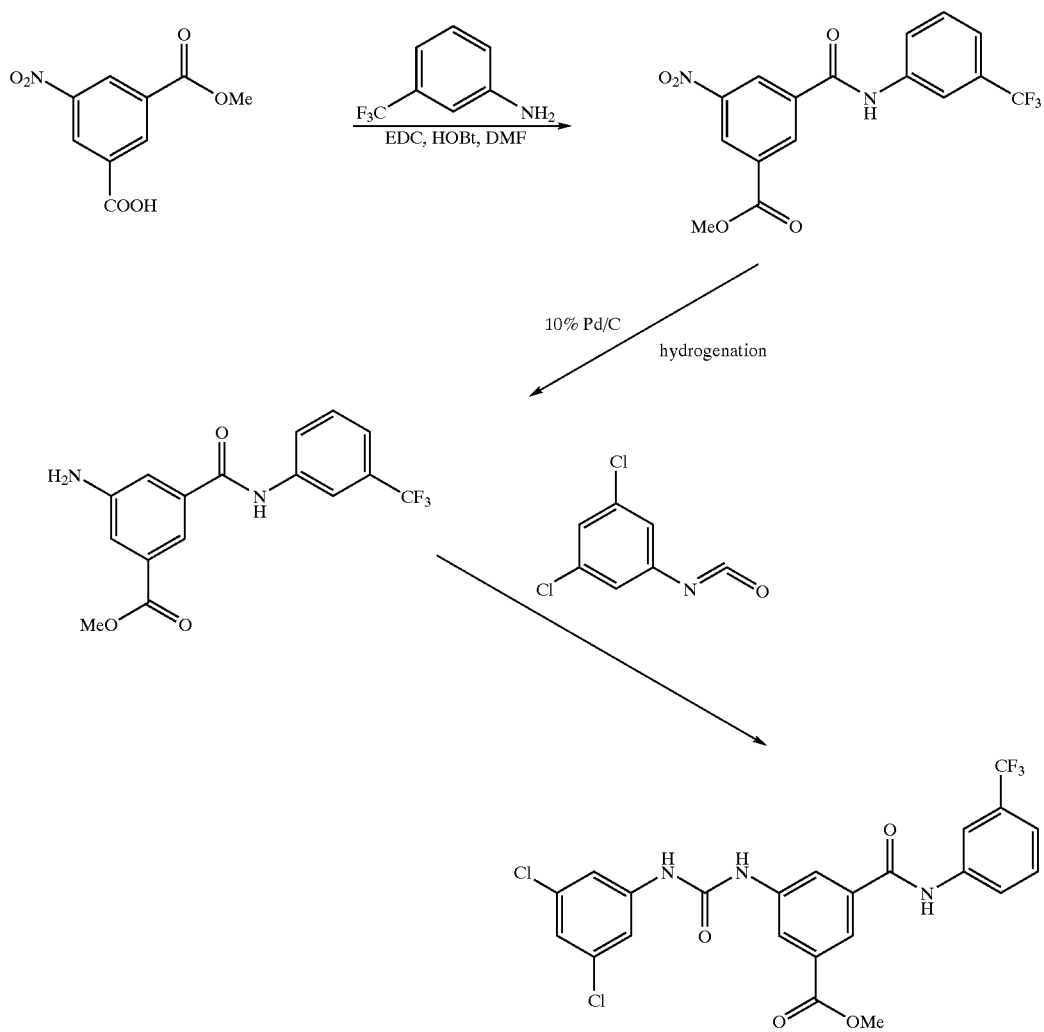

3-{3,5-Bis-[3-(3,5-dichlorophenyl)ureido]-phenyl)propionic acid methyl ester (Exemplary Compound 5). A solution containing 3-(3,5-dinitrophenyl)acrylic acid methyl ester (2 mmol) and catalytic amount of 10% Pd/C in 20 ml methylenechloride was subjected to hydrogenation under 50 psi for 20 minutes. The palladium catalyst was filtered. Then dichlorophenylisocyanate (4 mmol) was added to the filtrate and the mixture was stirred overnight at room temperature. The precipitation was collected by filtration and washed twice by methelenchloride. The crude product was recrystalized from acetone to afford pure product (91% yield) as white solid. Rf=0.60 (2:1 Hexane:EtAc); $^1$H NMR (DMSO-d6, 400 MHz) 8.96 (s, 2H), 8.88 (s, 2H), 7.53 (s, SH), 7.16 (s, 2H), 6.98 (s, 2H), 3.60 (s, 3H), 2.79 (t, 2H), 2.62 (t, 2H). Found: C, 50.45; H, 3.67; N, 9.98.

Exemplary Compound 4 was prepared from Examplary Compound 5: {6-[3-[3-(3,5-Dichloro-phenyl)-ureido]-5-(3-trifluoromethyl-phenylcarbamoyl)-benzoylamino]hexyl}carbamic acid tert-butyl ester $^1$H NMR (DMSO-d6, 400 MHz) 10.71 (s, 1H, NH), 9.28 (s, 1H, NH), 9.16 (s, 1H, NH), 8.54 (s, 1H, NH); 8.26 (s, 1H), 8.14 (s, 1H), 8.10 (m, 3H), 7.68 (t, 1H), 7.55 (s, 2H), 7.47(d, 1H), 7.18 (s, 1H), 6.75 (s, 1H), 3.26 (t, 2H), 2.91 (t, 2H), 1.32–1.57 (m, 17H). Anal: Calcd for: C, 54.55; H, 4.99; N, 9.64. Found: C, 54.34; H, 4.89; N, 9.88.

EXAMPLE 4

Synthesis of Exemplary Compounds 7, 29, and 30

Exemplary Compound 7 was prepared according to Scheme IV-A, below.

Scheme IV-A

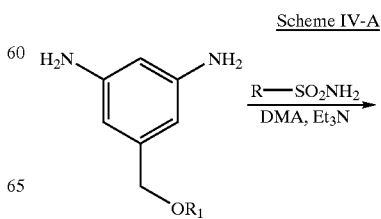

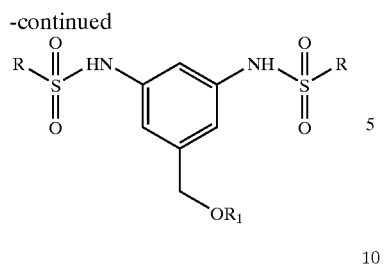

Synthesis of 1,3-(1-Naphthalene)-N-[5-(3,4-dichlorophenoxymethyl)-phenyl]-sulfonamide. (Exemplary Compound 7). 5-(3,4-dichlorophenoxymethyl) benzene-1,3-diamine (prepared according to the method of Scheme II-E) was dissolved in 5 ml DMA. 2 mmole TEA and 1 mmole naphthalene-1-sulfonyl chloride were added to the solution. The mixture was stirred at room temperature overnight and poured into ice water after GC-MS gave the disappearance of start material. The precipitate was filtered and re-crystalized from hexane/ethyl acetate. $^1$H NMR (DMSO-d6, 400 MHz) 4.82 (s, 2H); 6.60 (s, 2H); 6.79 (q, 1H); 6.90 (s, 1H); 7.10(d, 1H); 7.47 (q, 3H); 7.66 (m, 4H); 8.05 (t, 4H); 8.17 (d, 2H); 8.62 (d, 2H); 10.76 (s, 2H); Calcd for: C, 58.15; H, 3.84; N, 4.11; S, 9.41. Found: C, 57.98; H, 3.76; N, 4.23; S, 9.23.

Synthesis of Exemplary Compounds 29 and 30 was conducted according to Scheme IV-B, below.

Synthesis of bis[(3,5-dichlorophenyl)sulfonyl](3-{bis[(3,5-dichlorophenyl)sulfonyl]amino)-4-bromophenyl)amine (Exemplary Compound 30)

Scheme IV-B

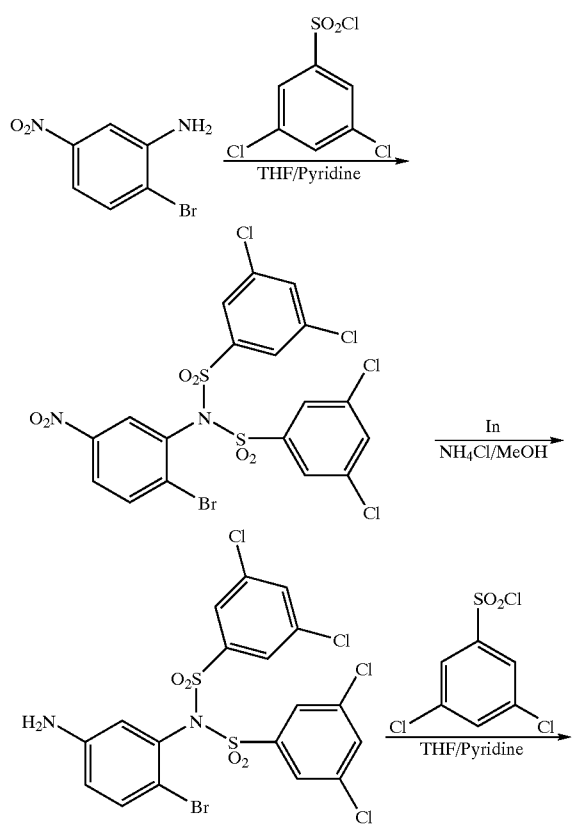

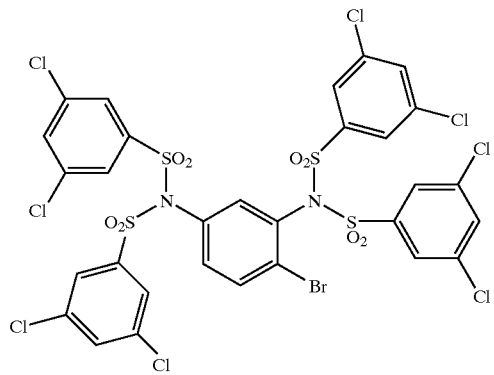

3-{Bis[(3,5-dichlorophenyl)sulfonyl]}amino-4-bromonitrobenzene. In a solution of 0.5 mmole 2-bromo-5-nitro-phenylamine in 4 ml mixture of THF:Pyridine (1:1), 1.2 mmole 3,5-dichloro-benzenesulfonyl chloride in 1 ml THF was added. The mixture was stirred under reflux overnight. The precipitate formed after cooling to room temperature was filtered and washed with ethyl acetate. GC-MS identified the material as the desired product.

3-{Bis[(3,5-dichlorophenyl)sulfonyl]}amino-4-bromoaniline. The precipitate from step 1 was dissolved in 2 ml MeOH and 0.6 ml saturated NH$_4$Cl and 0.4 g indium powder were added in. The mixture was stirred under reflux overnight. The reaction completion was judged by GC-MS and the cooled reaction mixture was diluted with H$_2$O and filtered through Celite. The aqueous filtrate was extracted with ethyl acetate (3×10 ml). The combined organic layers were dried (MgSO$_4$) and concentrated in vacuo. The crude product was used directly for next step.

Bis[(3,5-dichlorophenyl)sulfonyl](3-{bis[(3,5-dichlorophenyl)sulfonyl]amino)-4-bromophenyl)amine. (Exemplary Compound 30). The compound from step 2 was dissolved in 5 ml dimethylacetamide (DMA). 2 mmole triethylamine and 1 mmole 3,5-dichloro-benzenesulfonyl chloride were added to the solution. The mixture was stirred at room temperature overnight and poured into ice water after GC-MS indicated the disappearance of start material. The precipitate was filtered and re-crystalized from hexane/ethyl acetate to provide the compound of example 30: $^1$H NMR (DMSO-d6, 400 MHz) 7.19 (d, 1H); 7.55 (q, 1H); 7.89 (d, 4H); 7.94 (d, 4H); 8.03 (d, 1H); 8.16 (m, 4H).

Anal: Calcd for: C, 36.01; H, 1.79; N, 2.62; S, 12.02. Found: C, 36.24; H, 1.91; N, 2.81; S, 12.17.

Exemplary Compound 29 was produced according to Scheme IV-C, below:

Scheme IV-C

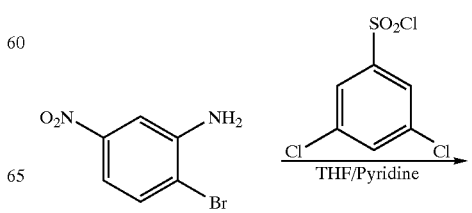

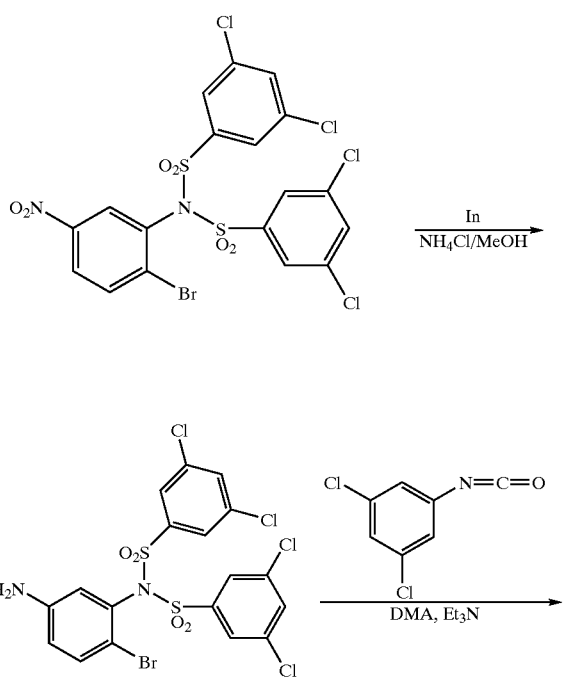

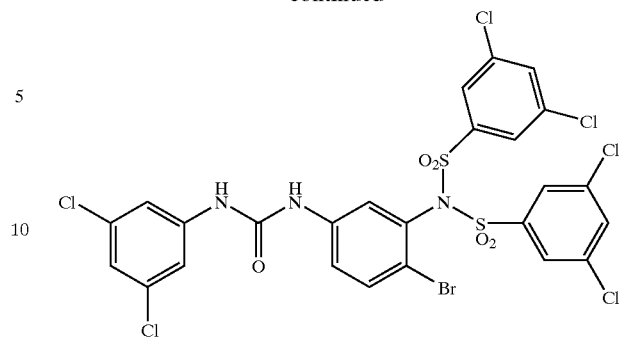

N-(3-{bis[(3,5-dichlorophenyl)sulfonyl]amino}-4-bromophenyl)[(3,5-dichlorophenyl)amino]formamide (Exemplary Compound 29). The same procedure as described for Exemplary Compound 30 was used for producing Exemplary Compound 29 except that 1,3-dichloro-5-isocyanato-benzene was used on the third step according to Scheme IV-C. Exemplary Compound 29: $^1$H NMR (DMSO-d6, 400 MHz) 7.11 (t, 1H); 7.40 (q, 1H); 7.67 (m, 3H); 7.82 (d, 1H); 7.93 (d, 4H); 8.15 (t, 2H); 9.19 (s, 1H); 9.32 (s, 1H). Anal: Calcd for: C, 38.31; H, 1.98; N, 5.15; S, 7.87. Found: C, 38.45; H, 2.02; N, 5.37; S, 8.10.

EXAMPLE 5

Synthesis of Exemplary Compound 8

Exemplary Compound 8 was prepared according to Scheme V, below.

Scheme V

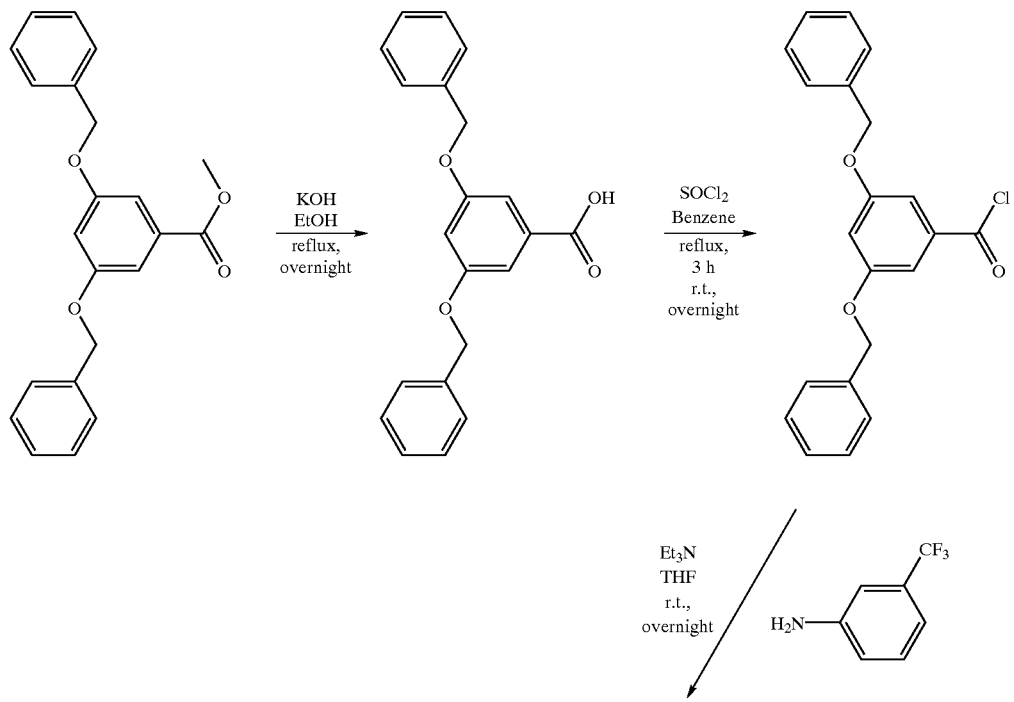

-continued

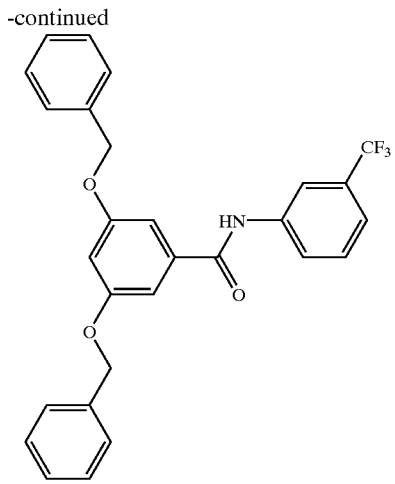

3,5-Bis(Benzyloxy)benzoic acid. The title compound was prepared according to the procedure of Scheme I-A, starting from methyl 3,5-bis(benzyloxy)benzoate (1.74 g, 5 mmol). White solid, yield 1.44 g (86%). $^1$H NMR (DMSO-$d_6$, 400 MHz), δ: 7.47–7.30 (m, 10H); 7.15 (s, 2H); 6.92 (s, 1H); 5.15 (s, 2H).

3,5-Bis(Benzyloxy)benzoic acid chloride. The title compound was prepared according to the procedure of Scheme I-A, starting from acid 3,5-bis(Benzyloxy)benzoic acid (1.32 g, 4.0 mmol). Off-white solid, yield 1.38 g (99%). Used immediately for preparation of Exemplary Compound 8.

3,5-Di(benzyloxy)-3'-(trifluoromethyl)benzanilid. (Examplary Compound 8). The title compound was prepared according to the procedure of Scheme I-A, starting from 3,5-bis(benzyloxy)benzoic acid chloride and 3-(trifluoromethyl)aniline in THF solution. White solid, yield 0.250 g (69%). 1H NMR (DMSO-$d_6$, 400 MHz), δ: 10.47 (s, 1H); 8.24 (s, 1H); 8.06 (d, J=8.3 Hz, 1H); 7.60 (t, J=8.0 Hz, 1H); 7.51–7.32 (m, 11H); 7.25 (s, 2H); 6.95 (s, 1H); 5.18 (s, 4H). Anal: Calcd. for $C_{28}H_{22}F_3NO_3$: 70.43; H, 4.64; N, 2.93. Found: C, 70.58; H, 4.67; N, 2.91.

EXAMPLE 6

Synthesis of Exemplary Compound 15

Exemplary Compound 15 was prepared according to Scheme VI, below.

Methyl 3-hydroxy-5-nitrobenzoate. A solution of 3-hydroxy-5-nitrobenzoic acid (2.00 g, 11 mmol) and concentrated sulfuric acid (0.5 mL) in MeOH (15 mL) was refluxed overnight, cooled to room temperature, and poured into mixture of $Na_2CO_3$ (saturated solution, 25 mL), water (150 mL), and ice (50 g). Resulting precipitate was filtered, washed with water (3×30 mL), and air-dried. Yellow microcrystals, yield 1.37 g (63%). $^1$H NMR (DMSO-$d_6$, 400 MHz), δ: 10.94 (s, 1H); 8.09 (s, 1H); 7.78 (s, 1H); 7.71 (s, 1H); 3.90 (s, 3H).

Scheme VI

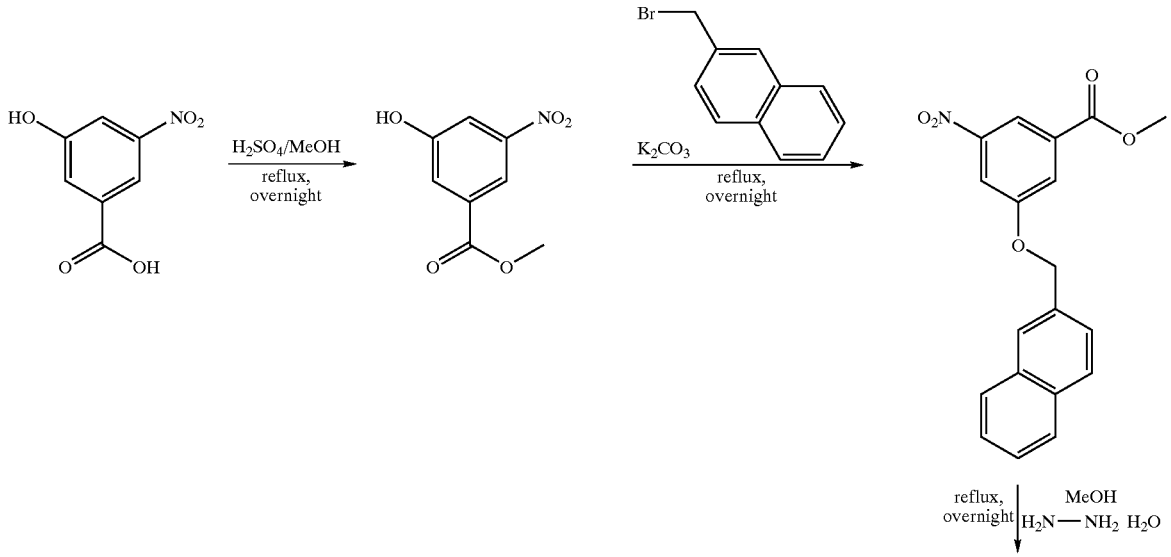

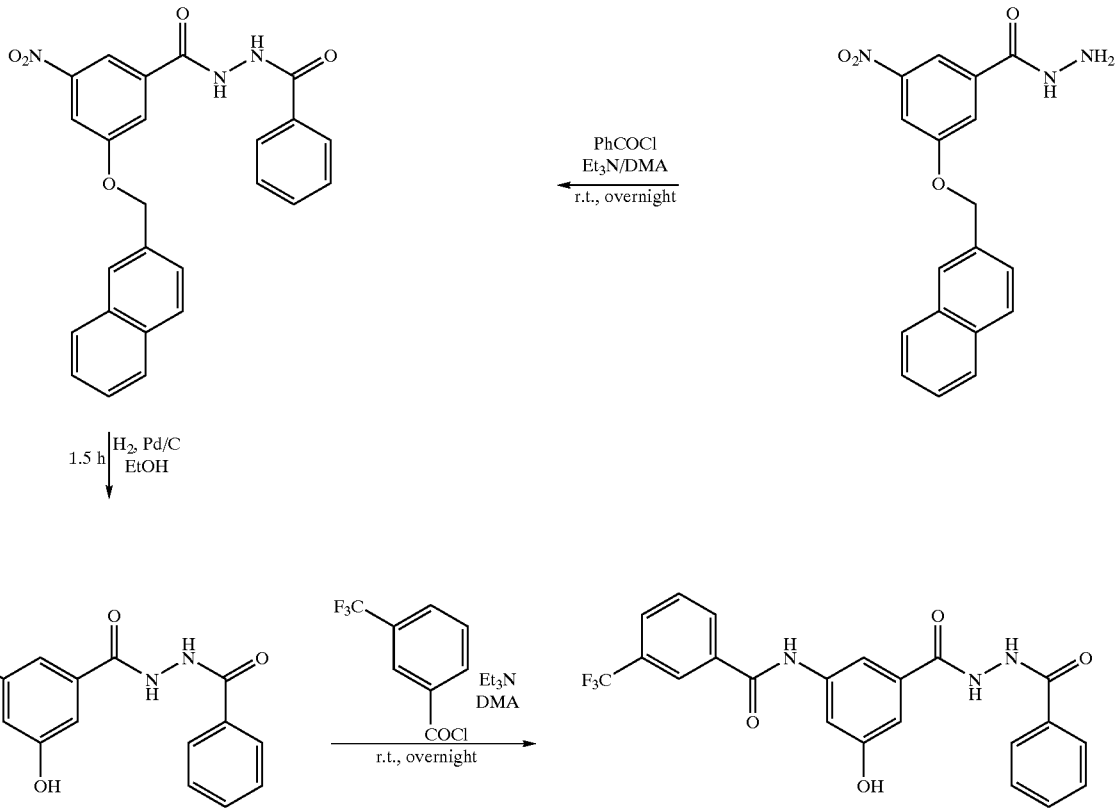

Methyl 3-[(2-naphthyl)methoxy]-5-nitrobenzoate. Methyl 3-hydroxy-5-nitrobenzoate (0.685 g, 3.5 mmol) was dissolved in acetone (75 mL). Potassium carbonate (1.43 g, 10.4 mmol) and 2-bromomethylnaphthalene (0.77 g, 3.5 mmol) were added, and the whole was stirred under reflux for 5 h. Mixture was cooled to room temperature and poured into basic (NaOH, pH 10–11) water. After 1 h, precipitated solid was filtered, washed with water (3×25 mL), and air-dried. Off-white crystals, yield 0.970 g (82%). $^1$H NMR (DMSO-$d_6$, 400 MHz), δ: 8.24 (s, 1H); 8.14 (s, 1H); 8.05 (s, 1H); 7.99–7.90 (m, 4H); 7.63 (d, J=7.5 Hz, 1H); 7.57–7.50 (m, 2H); 5.51 (s, 2H); 3.92 (s, 3H).

3-[(2-Naphthyl)methoxy]-5-nitrobenzhydrazide. A solution of methyl 3-[(2-naphthyl)methoxy]-5-nitrobenzoate (0.97 g, 2.87 mmol) and hydrazine hydrate (0.56 mL, 11.5 mmol) in MeOH (50 mL) was stirred under reflux overnight. Formation of solid hydrazide from a boiling mixture was observed in the morning. Mixture was cooled, solid filtered and air-dried. Greenish-white plates, yield 0.60 g (62%). $^1$H NMR (DMSO-$d_6$, 400 MHz), δ: 10.15 (br.s, 1H); 8.27 (s, 1H); 8.05–7.91 (m, 6H); 7.63 (d, J=7.5 Hz, 1H); 7.59–7.52 (m, 2H); 5.48 (s, 2H); 4.66 (br.s, 2H).

1-{3-[(2-Naphthyl)methoxy]-5-nitrobenzoyl}-2-benzoylhydrazine. To a stirred solution of 3-[(2-naphthyl)methoxy]-5-nitrobenzhydrazide (0.30 g, 0.89 mmol) and triethylamine (0.14 mL, 0.98 mmol) in DMA (25 mL) at room temperature was added benzoyl bromide (0.11 mL, 0.89 mmol), and stirring was continued overnight. Yellowish solution was poured onto ice-water (50 g) and set aside for 24 h. Precipitate formed was filtered, washed with water, and air-dried. Off-white solid, yield 0.34 g (87%). 1H NMR (DMSO-$d_6$, 400 MHz), δ: 10.92 (s, 1H); 10.66 (s, 1H); 8.12–7.89 (m, 8H); 7.67–7.50 (m, 6H); 5.53 (s, 2H).

1-(3-hydroxy-5-aminobenzoyl)-2-benzoylhydrazine. A mixture of 1-{3-[(2-naphthyl)methoxy]-5-nitrobenzoyl}-2-benzoylhydrazine (0.34 g, 0.77 mmol), Pd/C (10%, 0.35 g), EtOH (10 mL), and DMF (10 mL) was hydrogenated in Parr apparatus (H$_2$ pressure—30 psi) at room temperature for 1.5 h. Catalyst was filtered off, and filtrate concentrated in vacuo to give a slurry of white needles, which were filtered and washed with EtOH (3×25 mL). Yield 0.20 g (96%). 1H NMR (DMSO-$d_6$, 400 MHz), δ: 10.37 (s, 1H); 10.12 (s, 1H); 9.20 (s, 1H); 7.91 (d, J=7.0 Hz, 2H); 7.62–7.48 (m, 3H); 6.54 (s, 1H); 5.46 (s, 1H); 6.19 (s, 1H); 5.18 (br.s, 2H).

1-Benzoyl-2-{3-[(3-trifluoromethyl)phenyl]carbonylamino-5-hydroxy}benzoylhydrazine (Exemplary Compound 15). The title compound was prepared according to the method of Scheme I, from 3-(trifluoromethyl)benzoyl chloride and the above amine in DMA solution. White solid, yield 0.175 g (59%). $^1$H NMR (DMSO-$d_6$, 400 MHz), δ: 10.55 (s, 1H); 10.48 (s, 1H); 10.41 (s, 1H); 9.88 (s, 1H); 8.32 (s, 1H); 8.28 (d, J=7.5 Hz, 1H); 7.98 (d, J=8.0 Hz, 1H); 7.93 (d, J=8.0 Hz, 2H); 7.80 (t, J=8.0 Hz, 1H); 7.69 (s, 1H); 7.66–7.48 (m, 3H); 7.08 (s, 1H). Anal: Calcd. for $C_{22}H_{16}F_3N_3O_4 \cdot (0.4\ H_2O)$: C, 58.64; H, 3.76; N, 9.33. Found: C, 58.62; H, 3.75; N, 9.31.

EXAMPLE 7

Synthesis of Exemplary Compounds 33 and 34

Exemplary Compounds 33 and 34 were prepared according to Scheme VII, below.

(~75 mL) and washed successively with water and brine. The organic phase was dried with $MgSO_4$, filtered and evaporated. Flash chromatography (20%EtOAc/hexane) gave 2.0 g of product in (81%) yield as a pale yellow solid: MS (EI) m/z 358 ($M^+$).

Scheme VII

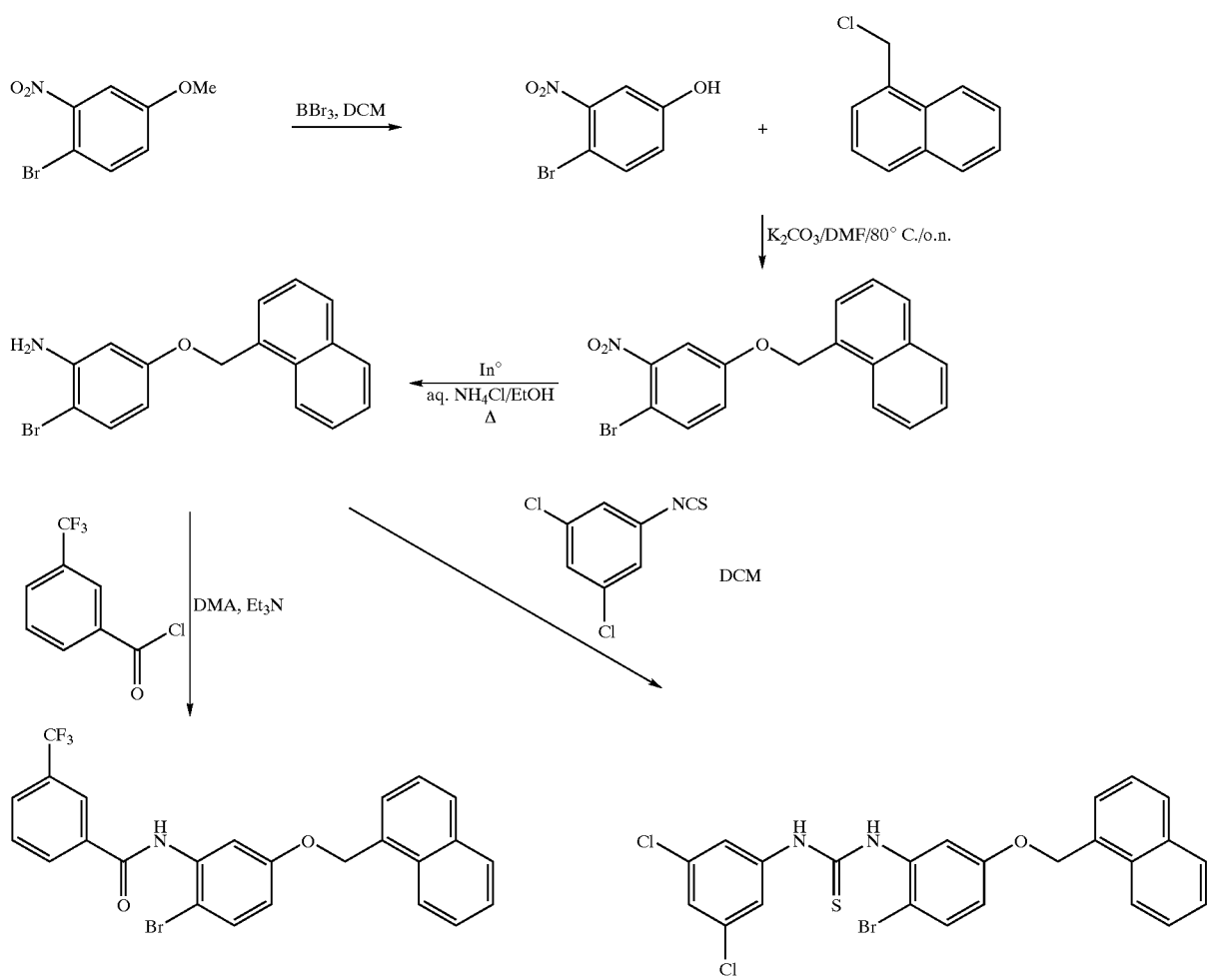

4-Bromo-3-nitrophenol. To a stirred solution of 1-bromo-4-methoxy-2-nitrobenzene (2.32 g, 10 mmol) in 75 mL of dichloromethane at 0° C. was added $BBr_3$ solution (1 M in DCM, 12 mL, 12 mmol) dropwise. The solution was allowed to warm to room temperature and stirred for 16 h. GC/MS showed starting material still left so another 12 mL of $BBr_3$ solution was added and the reaction mixture refluxed for 4 h. The reaction mixture was cooled in ice and quenched with water. After washing successively with saturated $NaHCO_{3(aq)}$ and brine, the organic layer was dried over $MgSO_4$, filtered and evaporated. The resulting yellow solid was flash chromatographed (25% EtOAc/hexane) to give 1.5 g of product in (69%) yield as a pale yellow solid: MS (EI) m/z 218 ($M^+$).

1-Bromo-4-(2-naphthylmethoxy)-2-nitrobenzene. A solution of 4-bromo-3-nitrophenol (1.5 g, 6.9 mmol), 1-(chloromethyl)naphthylene (1.34 g, 7.6 mmol) and $K_2CO_3$ (1.05 g, 7.6 mmol) in 50 mL of dry DMF was heated to 80° C. for 16 h. under nitrogen. The mixture was cooled, filtered and evaporated. The residue was taken up in ethyl acetate 2-Bromo-5-(2-naphthylmethoxy)phenylamine. To a solution of nitroether (1.0 g, 2.8 mmol) in 10 mL of absolute ethanol was added saturated $NH_4Cl_{(aq)}$ (3 mL) and indium powder (2.0 g, 17.4 mmol). The mixture was vigorously stirred under reflux for 4 h. The reaction mixture was filtered hot through Celite and the Celite washed generously with ethyl acetate. The organic phase was washed with water, brine, dried with $MgSO_4$, filtered and evaporated. The residue was flash chromatographed (25%EtOAc/hexane) to give 0.7 g of product in (76%) yield as a pale yellow solid. MS (EI) m/z 328 ($M^+$).

N-[2-bromo-5-(naphthylmethoxy)phenyl][3-(trifluoromethyl)phenyl]formamide (Exemplary Compound 34). 2-Bromo-5-(2-naphthylmethoxy)phenylamine (100 mg, 0.3 mmol) and 3-(trifluoromethyl)benzoyl chloride (63 mg, 0.3 mmol) in 10 mL of dimethyl acetamide containing triethylamine (0.5 mL, 3.6 mmol); stirred for 16 h., was obtained 5.2 mg of Exemplary Compound 34 as white needles after recrystallization from ethyl acetate/hexane: mp 125–127° C. $^1$H NMR (400 MHz, Me$_2$SO-d$_6$) δ5.59 (s, 2H); 7.05–8.33 (m, 14H); 10.35 (s, 1H). Anal. Calcd for C$_{25}$H$_{17}$BrF$_3$NO$_2$: C, 60.02; H, 3.42; N, 2.80. Found: C, 60.15; H, 3.52; N, 2.73.

[(3,5-Dichlorophenyl)amino]{[2-bromo-5-(naphthylmethoxy)phenyl]amino}methane-1-thione (Exemplary Compound 33). A solution of 2-bromo-5-(2-naphthylmethoxy)phenylamine (100 mg, 0.3 mmol) and 3,5-dichlorophenylisothiocyanate (60 mg, 0.3 mmol) in 10 mL of dichloromethane was stirred at room temperature for 16 h. The reaction mixture was evaporated to dryness and the residue recrystallized from ethyl acetate/hexane to give 60 mg of product in (38%) yield as a white solid: mp 149–151° C. $^1$H NMR (400 MHz, Me$_2$SO-d$_6$) δ5.56 (s, 2H); 7.02 (dd, 1H, J=3.0, 8.9); 7.29 (d, 1H, J=3.0); 7.35 (t, 1H, J=1.8); 7.49–7.69 (m, 7H); 7.93–7.99 (m, 2H); 8.07–8.10 (m, 1H); 9.78 (s, 1H); 10.10 (s, 1H). Anal. Calcd for C$_{24}$H$_{17}$BrCl$_2$N$_2$OS: C, 54.16; H, 3.22; N, 5.26; S, 6.02; Cl, 13.32; Br, 15.01. Found: C, 54.17; H, 3.32; N, 5.28; S,6.10; Cl, 13.31; Br, 15.00.

EXAMPLE 8

Preparation of Exemplary Compounds 45 and 46

Exemplary Compounds 45 and 46 were prepared according to Scheme VIII, below.

3-[(3,5-Dichlorophenoxy)methyl]-4-methoxyphenylamine hydrochloride. A mixture of 2-bromomethyl-1-methoxy-4-nitrobenzene (2.46 g, 0.01 M), 3,5-dichlorophenol (1.79 g, 0.011 M), and potassium carbonate (2.07 g, 0.015 M) in acetone (150 mL) was intensively stirred for 5 min, then dicyclohexano-18-crown-6 (80 mg) was added, and the whole was brought to reflux under continued stirring. After 4 h, the mixture was cooled to r.t., and stirring was continued for overnight. The solvent was evaporated in vacuo. A yellowish-white solid was triturated with water (200 mL) and stirred for 30 min. Liquids were removed from the flask using reversed filtration, and the resulting solid was diluted with EtOH (75 mL). To this suspension was added wet Ni Raney (2.0 g), and the whole was heated up to 60° C. A solution of hydrazine monohydrate (100%, 2.0 mL) in EtOH (5 mL) was added dropwise within 30 min under continued stirring. As soon as the mixture cleared, the whole was brought to reflux and kept under stirring for 1 h. The solution was cooled to room temperature, decanted from catalyst, and concentrated in vacuo. Oily residue was dissolved in MeOH (30 mL) and treated with HCl conc. (12 mL). The formed suspension was kept in the freezer overnight and then filtered. Microcrystals, yield 1.55 g. Filtrate was concentrated in vacuo, and the formed precipitate filtered to give additional amount of product (0.410 g). Total yield of the title compound was 1.960 g (59%).

Scheme VIII

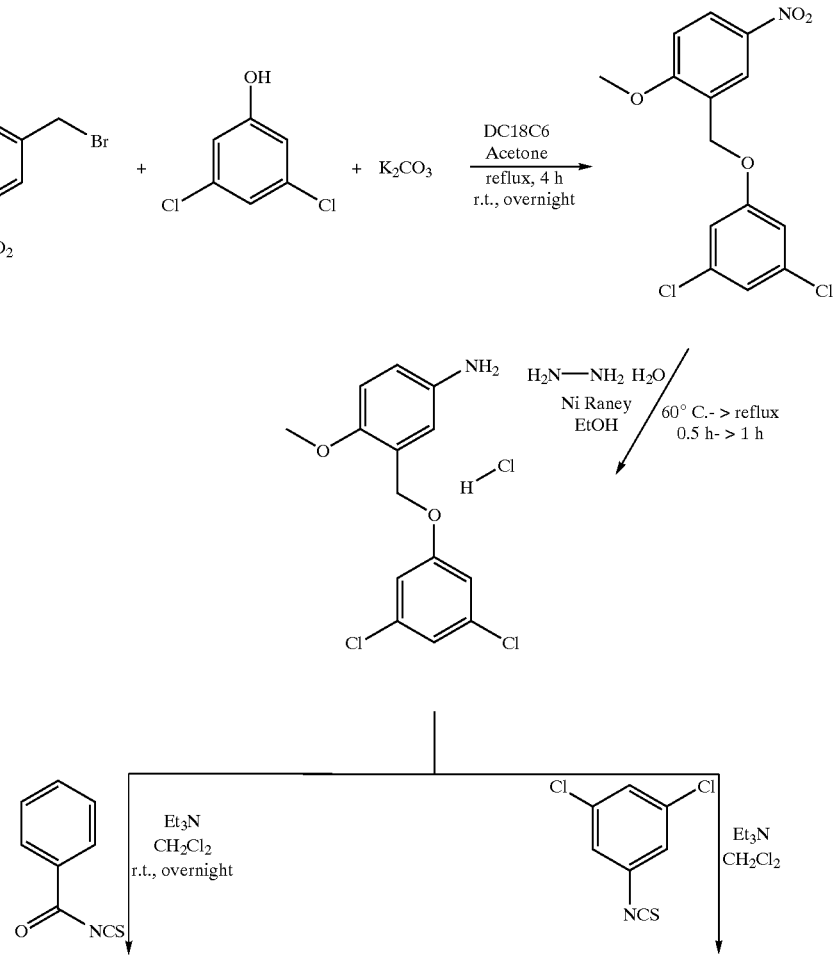

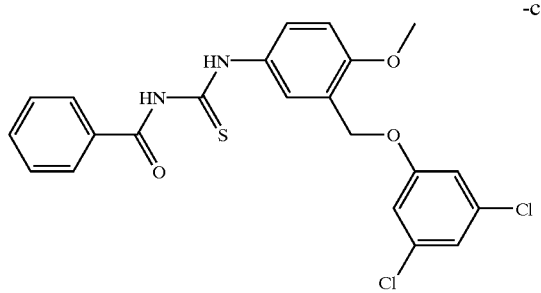
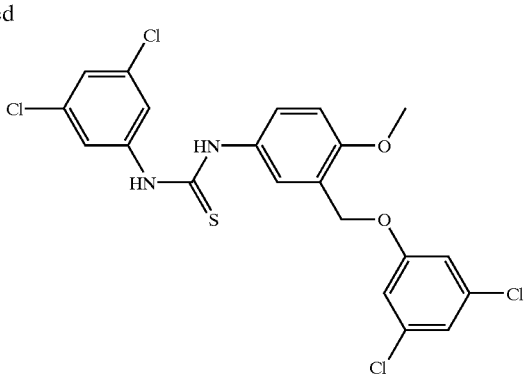

1-[3-(3,5-Dichlorophenoxy)methyl-4-methoxyphenyl]-3-benzoylthiourea (Exemplary Compound 46). A suspension of the above amine hydrochloride (0.167 g, 0.5 mmol) in dichloromethane (30 mL) was treated with triethylamine (0.076 mL, 0.55 mmol) at room temperature, stirred shortly (10 min), then benzoylisothiocyanate (0.067 mL, 0.5 mmol) was added to the formed solution in one portion. Stirring was continued overnight. Water (50 mL) was added to the mixture, and after extraction and separation of organic layer the solvent was evaporated in vacuo to give a solid, which was triturated with a mixture diethyl ether:hexanes and filtered. Yield 0.130 g (56%). Yellow crystals, m.p. 167–169° C. $^1$H NMR (DMSO-$d_6$, 400 MHz), δ: 12.45 (s, 1H); 11.53 (s, 1H); 7.98 (d, J=8.5 Hz, 2H); 7.69–7.61 (m, 3H); 7.56–7.51 (m, 2H); 7.18–7.09 (m, 4H); 5.12 (s, 2H); 3.86 (s, 3H). Anal: Calcd. for $C_{22}H_{18}Cl_2N_2O_3S$: C, 57.27; H, 3.93; N, 6.07. Found: C, 56.90; H, 4.01; N, 6.13.

1-[3-(3,5-Dichlorophenoxy)methyl-4-methoxyphenyl]-3-(3,5-dichlorophenyl)thiourea (Exemplary Compound 45). A suspension of the amine hydrochloride from Step 1 (0.167 g, 0.5 mmol) in dichloromethane (30 mL) was treated with triethylamine (0.076 mL, 0.55 mmol) at room temperature, stirred shortly (10 min), then 3,5-dichlorophenylisothiocyanate (0.102 g, 0.5 mmol) was added to the formed solution in one portion. Stirring was continued overnight. Water (50 mL) was added to the mixture, and after extraction and separation of organic layer the solvent was evaporated in vacuo to give a solid, which was triturated with a mixture diethyl ether:hexanes and filtered. Yield 0.145 g (57%). Pink microcrystals, m.p. 172–173° C. (dec.). $^1$H NMR (DMSO-$d_6$, 400 MHz), δ: 9.97 (s, 1H); 9.85 (s, 1H); 7.60 (s, 2H); 7.40–7.35 (m, 2H); 7.30 (s, 1H); 7.14 (s, 1H); 7.11 (s, 2H); 7.09–7.04 (m, 1H); 5.10 (s, 2H); 3.83 (s, 3H). Anal: Calcd. for $C_{21}H_{16}Cl_4N_2O_2S$: C, 50.22; H, 3.21; N, 5.58 Found: C, 50.29; H, 3.29; N, 5.49.

EXAMPLE 9

Preparation of Exemplary Compound 28

Exemplary Compound 28 was prepared according to Scheme IX, below.

3-[(3,5-Dichlorophenyl)methoxy]-4-methoxyphenylamine. The title compound was prepared according to the method of Scheme VIII, starting from 3-nitro-5-methoxyphenol and 3,5-dichlorobenzylchloride.

1-(3,5-Dichlorophenyl)-3-[3-(3,5-dichlorobenzyloxy)-4-methoxyphenyl]urea (Exemplary Compound 28). To a stirred solution of 3-[(3,5-dichlorophenyl)methoxy]-4-methoxyphenylamine (0.596 g, 2 mmol) in dichloromethane (30 mL) was added 3,5-dichlorophenylisothiocyanate (0.408 g, 2 mmol) in one portion. Stirring was continued overnight. Water (100 mL) was added to the mixture, and after extraction and separation of organic layer the solvent was evaporated in vacuo to give a solid, which was triturated with a mixture diethyl ether:hexanes and filtered. Yield 0.273 g (27%). White micro-crystals, m.p. 154–155° C. (dec.); $^1$H NMR (DMSO-d6, 400 MHz) 9.67 (s, 1H); 9.74 (s, 1H); 7.59 (s, 2H); 7.53 (s, 1H); 7.48 (s, 2H); 7.30 (s, 1H); 7.11 (s, 1H); 7.00 (d, J=8.5 Hz, 1H), 6.92 (dd, J=9.0 and 2.5 Hz, 1H); 5.10 (s, 2H); 3.79 (s, 3H). Anal: Calcd for: C, 50.22; H, 3.21; N, 5.58. Found: C, 50.50; H, 3.45; N, 5.56.

Scheme IX

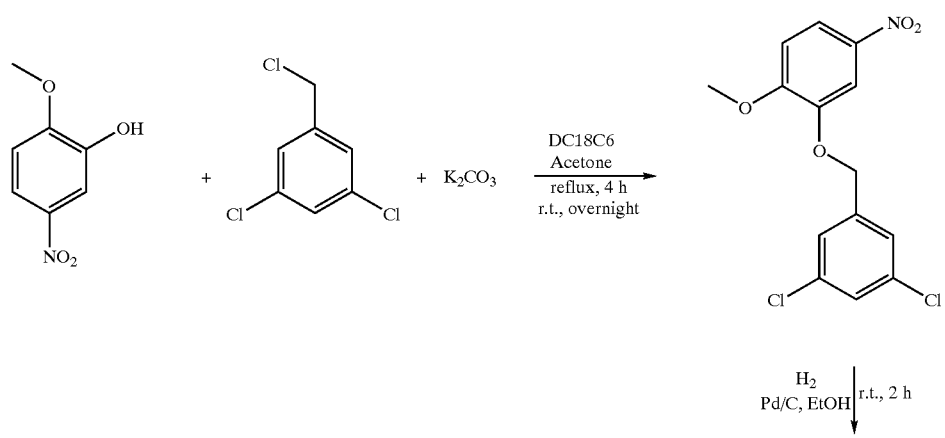

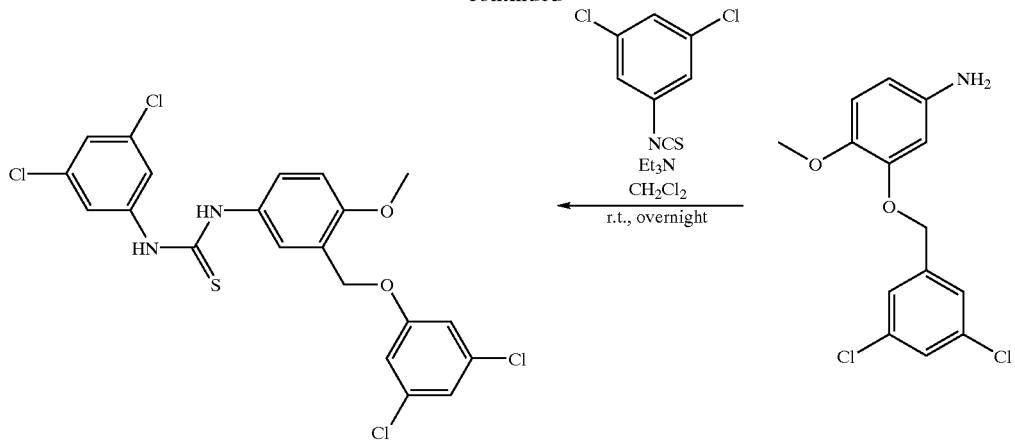

EXAMPLE 10

Preparation of Exemplary Compound 52

Exemplary Compound 52 was prepared according to Scheme X, below.

(Diphenylmethyl)[(4-chloro-3-nitrophenyl)sulfonyl]amine. To a stirred solution of aminodiphenylmethane (1.9 g, 11 mmol) and 4-chloro-3-nitrobenzenesulfonyl chloride (2.56 g, 10 mmol) in 75 mL of dichloromethane was added triethylamine (2 mL, 14.4 mmol). The solution was stirred for 16 h. The reaction mixture was washed successively with 1M HCl and brine. The organic layer was dried over $MgSO_4$, filtered and evaporated. The resulting yellow solid was recrystallized from ethyl acetate/hexane to give 2.98 g of product in (74%) yield as pale yellow crystals: $^1$H NMR (400 MHz, $CDCl_3$) δ5.34 (d, 1H, J=7.0 Hz), 5.73 (d, 1H, J=7.0 Hz), 7.11–7.14 (m, 4H), 7.23–7.26 (m, 6H), 7.43 (d, 1H, J=8.5 Hz), 7.67 (dd, 1H, J=2.0, 8.5 Hz), 7.93 (d, 1H, J=2.0 Hz).

Scheme X

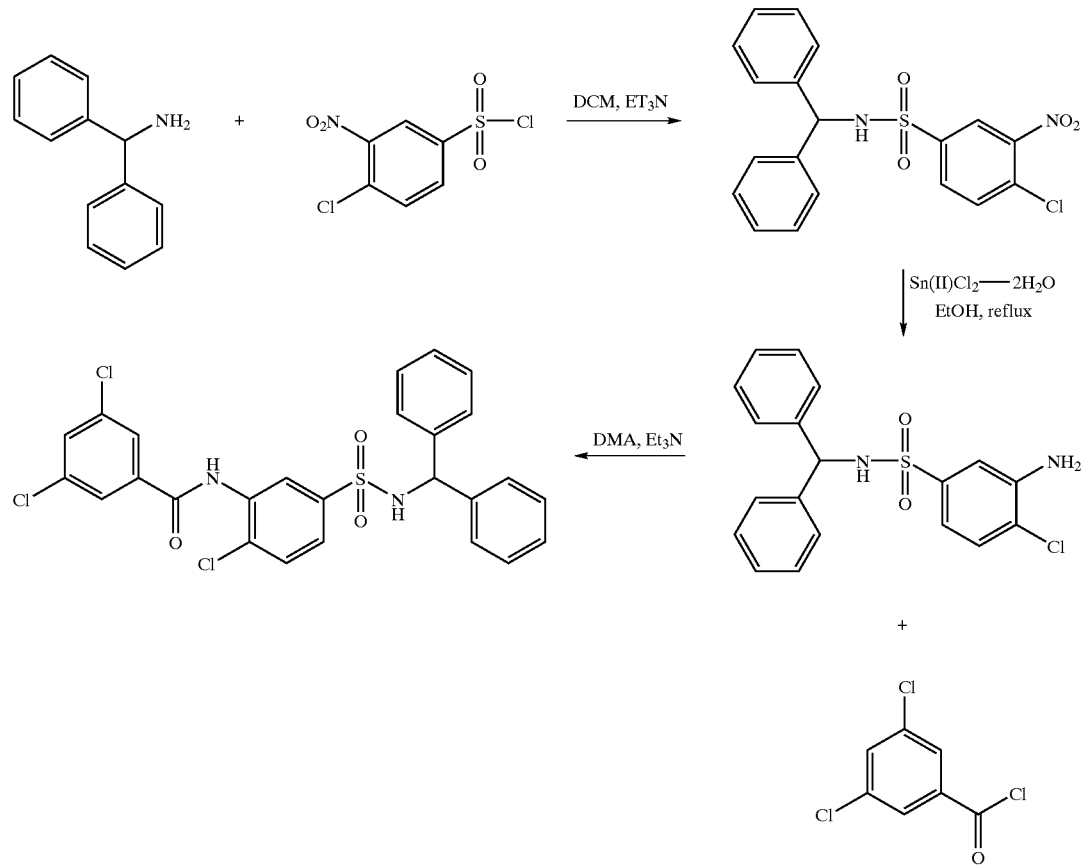

[(3-Amino-4-chlorophenyl)sulfonyl](diphenylmethyl) amine. A solution of the nitro compound from Step 1 (2.0 g, 5 mmol) and Sn(II)Cl$_2$ dihydrate (5.5 g, 24.4 mmol) in 50 mL of absolute ethanol was refluxed under nitrogen for 1 h. The reaction mixture was poured onto ice, neutralized with solid NaHCO$_3$ and extracted with ethyl acetate. The organic phase was washed with brine, dried over MgSO$_4$, filtered and evaporated to give 1.7 g of product (92%) as a white crystalline solid which was carried on without further purification. MS (EI) m/z 372 (M$^+$).

(3,5-Dichlorophenyl)-N-(5-{[(diphenylmethyl)amino]sulfonyl}-2-chlorophenyl)formamide (Exemplary Compound 52). To a stirred solution of (570 mg, 1.53 mmol) and 3,5-dichlorobenzoyl chloride (340 mg, 1.62 mmol) in 10 mL of dimethyl acetamide was added triethylamine (1 mL, 7.17 mmol). The solution was stirred at room temperature for 16 h. The reaction mixture was then poured onto ice and the precipitate that resulted on standing was collected by filtration. Washed generously with water and after drying, the solid was recrystallized from ethyl acetate/hexane to give 600 mg of product in (71%) yield as pale orange crystals: mp 196–198° C. $^1$H NMR (400 MHz, CDCl$_3$) δ5.21 (d, 1H, J=7.5 Hz); 5.69 (d, 1H, J=7.5 Hz); 7.14–7.24 (m, 10H); 7.33–7.39 (m, 2H); 7.61 (t, 1H, J=1.8 Hz); 7.75 (d, 2H, J=1.8 Hz); 8.22 (bs, 1H); 8.84 (d, 1H, J=2.0 Hz). Anal. Calcd for C$_{26}$H$_{19}$Cl$_3$N$_2$O$_3$S: C, 57.21; H, 3.51; N, 5.13; Cl, 19.48; S, 5.87. Found: C, 57.39; H, 3.54; N, 5.16; Cl, 19.40; S, 5.74.

EXAMPLE 11

Synthesis of Exemplary Compound 51

Exemplary Compound 51 was prepared as described in Scheme XI, below.

3-Amino-6-chlorophenyl phenyl ketone. From 2-chloro-5-nitrophenyl phenyl ketone (5.5 g, 21.0 mmol) and Sn(II)Cl$_2$ dihydrate (23.7 g, 107 mmol) in 200 mL of absolute ethanol refluxed for 2 h., was obtained 4.9 g of product in (100%) yield as an orange oil. This material was used without further purification. MS (EI) m/z 231 (M$^+$).

(3,5-Dichlorophenyl)-N-[4-chloro-3-(phenylcarbonyl)phenyl]formamide (Exemplary Compound 51) was prepared using the same experimental conditions used to prepare Exemplary Compound 52 (Scheme XI, above). From 3-amino-6-5 chlorophenyl phenyl ketone (1.62 g, 7 mmol) and 3,5-dichlorobenzoyl chloride (1.5 g, 7.2 mmol) in 25 mL of dimethyl acetamide containing triethylamine (2 mL, 14.4 mmol) stirred for 16 h., was obtained 2.1 g of product (74% yield) as fluffy white needles after recrystallization from ethyl acetate/hexane: mp 171–173° C. $^1$H NMR (400 MHz, CDCl$_3$) δ7.45–7.64 (m, 6H); 7.73 (d, 2H, J=1.9 Hz); 7.82–7.85 (m, 3H); 7.95 (bs, 1H). Anal. Calcd for C$_{20}$H$_{12}$Cl$_3$NO$_2$: C, 59.36; H, 2.99; N, 3.46; Cl, 26.28. Found: C, 59.55; H, 3.06; N, 3.50; Cl, 26.11.

EXAMPLE 12

Preparation of Exemplary Compound 50

Exemplary Compound 50 was prepared according to Scheme XII, below.

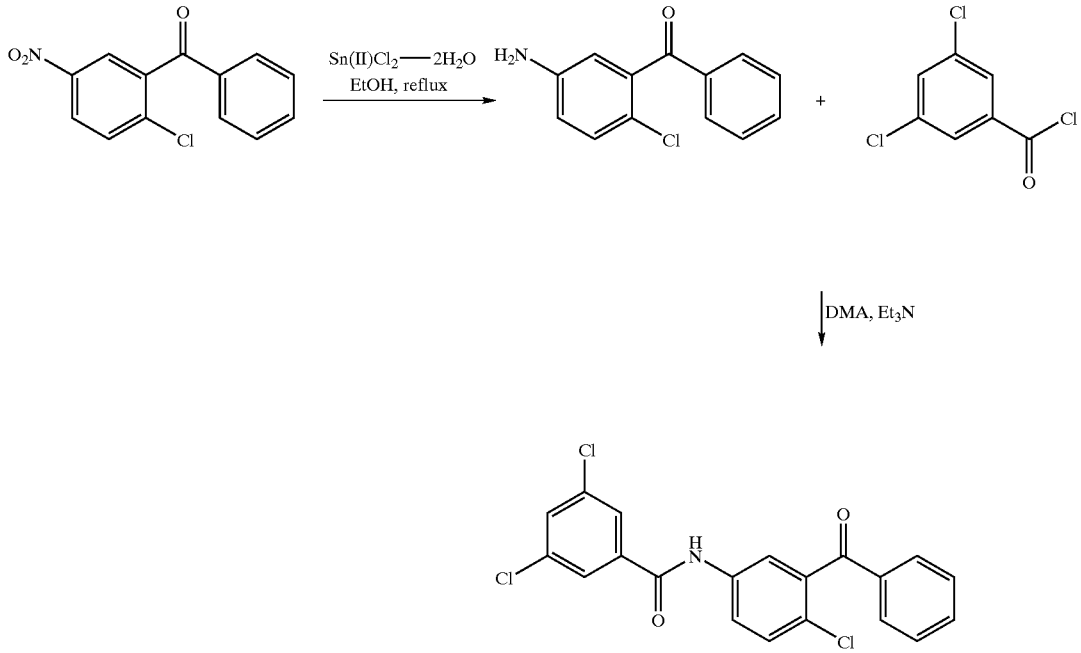

Scheme XI

Scheme XII

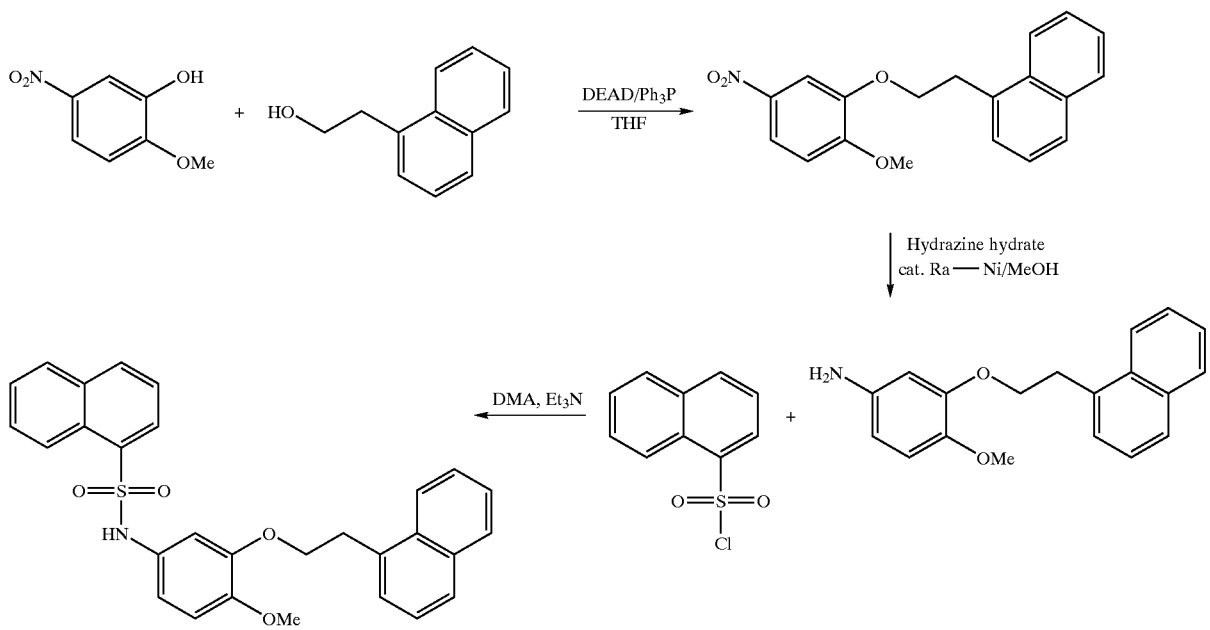

1-Methoxy-2-(2-naphthylethoxy)-4-nitrobenzene. To a stirred and cooled (in ice) solution of Ph$_3$P (9.3 g, 35.5 mmol) and 1-naphthyleneethanol (6.1 g, 35.5 mmol) in 250 mL of THF was added a solution of DEAD (6.18 g, 35.5 mmol) in 50 mL of THF dropwise. The solution was stirred for 0.5 h. and a solution of 2-methoxy-5-nitrophenol (5.0 g, 29.6 mmol) in 50 mL of THF was added dropwise. The reaction mixture was allowed to warm to room temperature and stirred for 48 h. The reaction mixture was evaporated to a brown oil which was taken up in ether (200 mL) and hexane added until a slight cloudiness persisted. Allowed this mixture to sit at room temperature until crystallization occurred and refrigerated overnight. The resulting solid was filtered, washed with ether/hexane (1:2) and dried to give ~18 g of a light brown solid. GC/MS showed this solid to contain only product and triphenylphosphine oxide. The solid was dissolved in ~150 mL of hot ethyl acetate and after cooling to room temperature, suction filtered through silica gel (~300 g) eluting with ethyl acetate/hexane (1:5). After collecting ~1 L of solvent, evaporation gave 4.80 g of product in (50%) yield as pale yellow powder: MS (EI) m/z 323 (M$^+$).

4-Methoxy-3-(2-naphthylethoxy)phenylamine. A solution of the above nitro compound (2.0 g, 6.18 mmol) and hydrazine hydrate (1.5 mL, 30.9 mmol) in 100 mL of methanol was warmed to near reflux. A spatula tip full of Raney nickel catalyst (50% slurry in water) was added and the solution immediately frothed. The mixture was brought to reflux for 0.5 h. As the reaction proceeds the color changes from yellow to colorless. The reaction mixture was cooled, filtered through Celite and evaporated. The resulting residue was redissolved in ethyl acetate, washed with brine, dried over MgSO$_4$, filtered and evaporated to give 1.5 g of product (88%) as a pale brown oil which crystallized on standing. This solid was carried on without further purification: $^1$H NMR (400 MHz, CDCl$_3$) δ3.38 (bs, 2H), 3.64 (t, 2H, J=8.0 Hz), 3.79 (s, 3H), 4.29 (t, 2H, J=8.0 Hz), 6.22–6.28 (m, 2H), 6.73 (d, 1H, J=8.0), 7.40–7.54 (m, 4H), 7.74–7.77 (m, 1H), 7.86–7.88 (m, 1H), 8.11 (d, 1H, J=8.5 Hz); MS (EI) m/z 293 (M$^+$).

[4-Methoxy-3-(2-naphthylethoxy)phenyl](naphthylsulfonyl)amine (Exemplary Compound 50). To a stirred solution of the aniline from Step 2 (250 mg, 0.85 mmol) and 1-naphthylenesulfonyl chloride (190 mg, 0.85 mmol) in 10 mL of dimethyl acetamide was added triethylamine (1 mL, 7.17 mmol). The solution was stirred at room temperature for 16 h. The reaction mixture was then poured onto ice. The resulting oil was extracted with ethyl acetate and washed successively with 1M HCl, saturated NaHCO$_3$ $_{(aq)}$ and brine. The organic phase was dried with MgSO$_4$, filtered and evaporated to give a white foam. This foam was crystallized from ether/hexane with vigorous stirring. The resulting solid was recrystallized from ethyl acetate/hexane to give 330 mg of product in (80%) yield as beige crystals: mp 127–131° C. $^1$H NMR (400 MHz, Me$_2$SO-d$_6$) δ3.36 (t, 2H, J=7.1); 3.57 (s, 3H); 3.92 (t, 2H, J=7.1); 6.48–6.50 (m, 2H); 6.70–6.72 (m, 1H); 7.34–8.07 (m, 13H); 8.68 (d, 1H, J=8.6); 10.21 (s, 1H). Anal. Calcd for C$_{29}$H$_{25}$NO$_4$S: C, 72.03; H, 5.21; N, 2.90; S, 6.63. Found: C, 71.93; H, 5.23; N, 2.88; S, 6.62.

EXAMPLE 13

Preparation of Exemplary Compounds 47, 48, and 49

Exemplary Compounds 47, 48 and 49 were prepared according to Scheme XIII, below.

1-Methoxy-2-(naphthylethoxy)-4-nitrobenzene. Nitroether was prepared using the same experimental conditions described in Scheme XII. From 2-methoxy-5-nitrophenol (5.0 g, 29.6 mmol), 1-naphthylenemethanol (5.62 g, 35.5 mmol), Ph$_3$P (9.3 g, 35.5 mmol) and DEAD (6.18 g, 35.5 mmol) in 250 mL of THF stirred at room temperature for 48 h., was isolated 10.4 g of crude product. This solid was recrystallized from ethyl acetate to give 3.8 g of product in (42%) yield as light yellow needles. MS (EI) m/z 309 (M$^+$).

4-Methoxy-3-(2-naphthylethoxy)phenylamine was prepared using the same experimental conditions described in Scheme XII. From 1-methoxy-2-(naphthylmethoxy)-4-nitrobenzene (3.8 g, 12.3 mmol), hydrazine hydrate (3.1 g, 61.4 mmol) and a catalytic amount of Raney nickel in 100 mL of methanol refluxed for 0.5 h., was obtained 3.5 g of product in (100%) yield as a brown oil that crystallized on standing. MS (EI) m/z 279 (M+).

Calcd for $C_{32}H_{27}NO_3$: C, 81.16; H, 5.75; N, 2.96. Found: C, 80.95; H, 5.76; N, 3.03.

N-[4-methoxy-3-(naphthylmethoxy)phenyl]-2-naphthylethanamide (Exemplary Compound 48) was prepared using the same experimental conditions used to prepare Exemplary Compound 52 (Scheme X, above). From

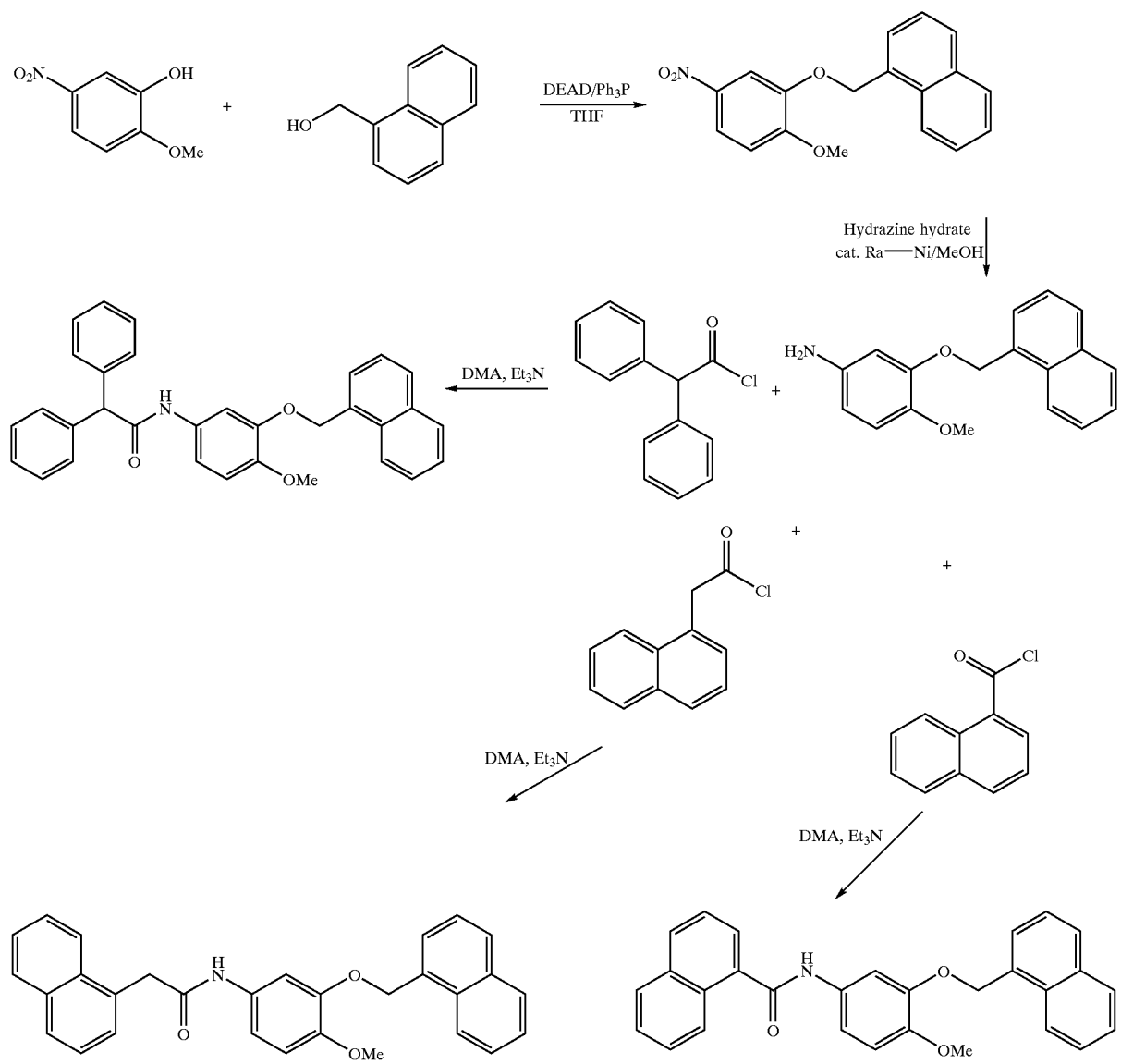

Scheme XIII

N-[4-methoxy-3-(naphthylmethoxy)phenyl]-2,2-diphenylethanamide (Exemplary Compound 49) was prepared using the same experimental conditions used to prepare Example 52 (Scheme X). From 4-methoxy-3-(2-naphthylethoxy)phenylamine (350 mg, 1.25 mmol) and diphenylacetyl chloride (290 mg, 1.25 mmol) in 10 mL of dimethyl acetamide containing triethylamine (1 mL, 7.17 mmol) stirred at room temperature for 16 h., was obtained 375 mg of product in (64%) yield as a white solid after recrystallization from ethyl acetate/hexane: mp 170–172° C. $^1$H NMR (400 MHz, Me$_2$SO-d$_6$) δ3.69 (s, 3H); 5.13 (s, 1H); 5.46 (s, 2H); 6.93 (d, 1H, J=8.7); 7.20–7.37 (m, 10H); 7.50–7.65 (m, 5H); 7.94–8.09 (m, 3H); 10.28 (s, 1H). Anal.

4-methoxy-3-(2-naphthylethoxy)phenylamine (350 mg, 1.25 mmol) and 1-naphthylacetyl chloride (260 mg, 1.25 mmol) in 10 mL of dimethyl acetamide containing triethylamine (1 mL, 7.17 mmol) stirred at room temperature for 16 h., was obtained 370 mg of product in (66%) yield as off white needles after recrystallization from ethyl acetate/hexane: mp 161–163° C. $^1$H NMR (400 MHz, Me$_2$SO-d$_6$) δ3.69 (s, 3H); 4.11 (s, 2H); 5.45 (s, 2H); 6.93 (d, 1H, J=8.8); 7.18 (dd, 1H, J=2.3, 8.7); 7.46–7.64 (m, 9H); 7.82–8.15 (m, 6H); 10.20 (s, 1H). Anal. Calcd for $C_{30}H_{25}NO_3$: C, 80.51; H, 5.63; N, 3.13. Found: C, 80.38; H, 5.70; N, 3.12.

N-[4-methoxy-3-(naphthylmethoxy)phenyl] naphthylformamide (Exemplary Compound 47) was prepared using the same experimental conditions used to prepare Exemplary Compound 52 (Scheme X, above). From 4-methoxy-3-(2-naphthylethoxy)phenylamine (350 mg, 1.25 mmol) and 1-naphthoyl chloride (240 mg, 1.25 mmol) in 10 mL of dimethyl acetamide containing triethylamine (1 mL, 7.17 mmol) stirred at room temperature for 16 h., was obtained 280 mg of product in (52%) yield as white needles after recrystallization from ethyl acetate/hexane: mp 161–163° C. $^1$H NMR (400 MHz, Me$_2$SO-d$_6$) δ3.74 (s, 3H); 5.52 (s, 2H); 7.01 (d, 1H, J=8.8); 7.43 (dd, 1H, J=2.3, 8.7); 7.51–7.74 (m, 9H); 7.94–8.21 (m, 6H); 10.43 (s, 1H). Anal. Calcd for C$_{29}$H$_{23}$NO$_3$: C, 80.35; H, 5.35; N, 3.23. Found: C, 80.25; H, 5.39; N, 3.19.

EXAMPLE 14

Preparation of Exemplary Compound 53

Exemplary Compound 53 was prepared according to the procedure of Scheme XIV, below:

3-(Acylamino)-5-bromobenzoic acid methyl ester (2a Scheme XIV). A mixture of the corresponding acid 1a (5 mmol), methyl 3-amino-5-bromobenzoate (5 mmol), and 1-[3-(dimethylamino)propyl]-3-ethylcarbodiimide hyfrochloride (EDC, 5.7 mmol) in dry THF (30 mL) is stirred at room temperature for 20 h. The whole is poured onto ice-water mixture (100 g) and left stand aside for 2 h. The product is extracted with methylene chloride (75 mL). The organic layer is separated, dried (Na$_2$SO$_4$ ahyd.), and solvents evaporated in vacuum. Depending on the appearance of the product, it is used as is (solid) or further subjected to column chromatography (oil), using silica gel and EtOAc:hexanes 1:2 eluting system.

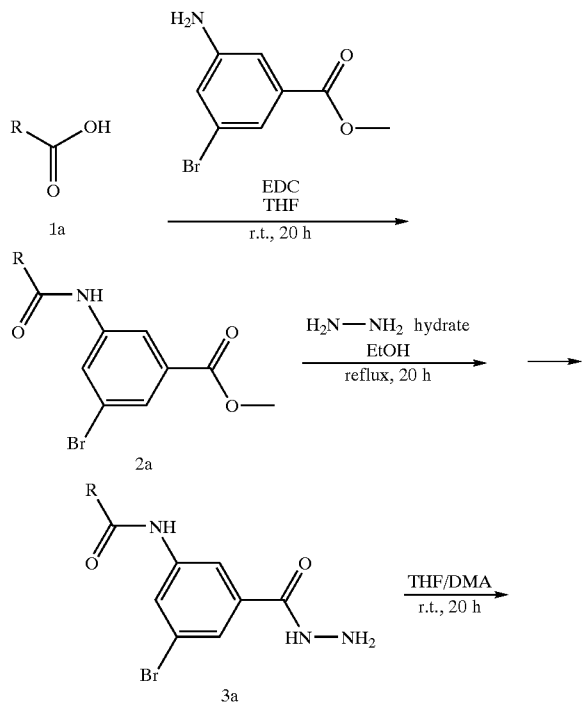

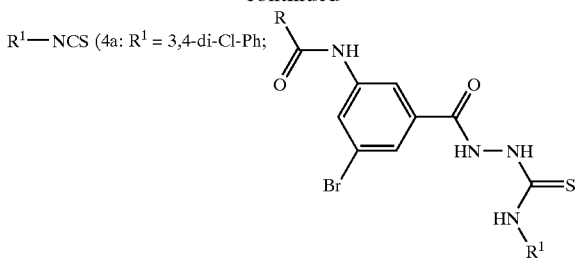

3-(Acylamino)-5-bromobenzoic acid hydrazide (3a, Scheme XIV). A solution of the corresponding ester 2a (5 mmol) and hydrazine hydrate (8 mL) in the mixture of propanol-2 or ethanol (100 mL) and water (1 mL) is stirred and refluxed for 20 h. Solvent evaporated in vacuum to produce yellowish-white solid, which is triturated with a minimum amount of ethanol (5–8 mL), filtered, and air-dried.

1-{3-[(5-Phenyl)valeroylamino]-5-bromobenzoyl}-4-(3,4-dichlorophenyl) thiosemicarbazide (Exemplary Compound 53; 5a in Scheme XIV). To a stirred solution of hydrazide 3a (0.3 mmol) in the mixture of THF (4 mL) and DMA (1 mL) is added a solution of isothiocyanate 4a (0.043 mL, 0.3 mmol) in THF (1 mL) in one portion. The whole is stirred for 18 h, poured onto ice-water. The residue formed is filtered and then recrystallized from aq. EtOH to give Compound 53.

EXAMPLE 15

Measuring the Inhibition of Rotamase (Prolyl Peptidyl Cis-Trans Isomerase) Activity A number of substrates for rotamase are known in the art or can be derived from those known. Typically, the substrate contacts a sample containing a protein with rotamase activity and the conversion of the substrate is detected after a period of time. The method for detecting conversion of the substrate will vary with the particular substrate chosen. One method has been termed the K$_i$ test (See Harding, et al., *Nature*, 341:758–760 (1989); and Holt et al., *J. Am. Chem. Soc.*, 115:9923–9938). The cis-trans isomerization of an alanine-proline bond in a model substrate, N-succinyl-Ala-Ala-Pro-Phe-p-nitroanilide (SEQ ID NO: 1), is monitored spectrophotometrically in a chymotrypsin-coupled assay. The action of chymotrypsin releases p-nitroaniline from only the trans form of the substrate. The amount of p-nitroaniline can be monitored in a spectrophotometer, for example. Other methods of detecting the presence of p-nitroaniline can also be used. The inhibition of this reaction caused by different concentrations of inhibitor is determined and the data are analyzed as a change in first-order rate constant as a function of inhibitor concentration, which yields the K$_i$ value.

The following were added to a plastic cuvette: 950 μl of ice cold assay buffer (25 mM HEPES, pH 7.8, 100 mM NaCl), 10 μL of CyP A (2.5 μM in 10 mM Tris-Cl pH 7.5, 100 mM NaCl, 1 mM dithiothreitol), 25 μL of chymotrypsin (50 mg/ml in 1 mM HCl), and 10 μL of test compound, at various concentrations, in dimethyl sulfoxide. The reaction was initiated by the addition of 5 μL of substrate (succinyl-Ala-Phe-Pro-Phe-para-nitroanilide (SEQ ID NO: 1), 5 mg/mL in 470 mM LiCl in trifluoroethanol). The absorbance at 390 nm versus time was monitored for 90 seconds using a spectrophotometer and the rate constants were determined from the absorbance versus time data files.

The $IC_{50}$ values which were obtained for representative compounds are given in the following Table A, and refer to the concentration that inhibits 50% of the rotamase activity in a sample. The lower the value, the more active the compound is at binding or interacting with CyP.

TABLE A

| Compound # | $IC_{50}$ (nM) |
|---|---|
| 13 | 456 |
| 15 | 18,700 |
| 20 | 153 |
| 21 | 490 |
| 25 | 297 |
| 26 | 909 |
| 27 | 214* |
| 28 | 914* |
| 29 | 10,000* |
| 31 | 1,580/3,530* |
| 32 | 164/102* |
| 33 | 707* |
| 34 | 11,700/12,000* |
| 35 | 1,310* |
| 36 | 609* |
| 37 | 1,200 |
| 38 | 736 |
| 41 | 1,370 |
| 42 | 230* |
| 43 | 377* |
| 44 | 374* |
| 45 | 609* |
| 46 | 3,770* |
| 47 | 1,220* |
| 48 | 1,190* |
| 49 | 1,020* |
| 50 | 978* |
| 51 | 1,550* |
| 52 | 861* |

The Cyclophilin utilized was a human recombinant CyPA, [Yoo et al., *J. Mol. Biol.*, 269 (1997) 780–95]. An asterisk indicates that the compound was evaluated using a recombinant rat CyPA-GST fusion protein: CypA was amplified from rat brain cDNA using standard PCR methods, primed with the following sequences:

```
                                         (SEQ ID NO: 2)
5' CCC CCC GGG AGT CAA CCC CAC CGT GTT CTT CGA 3'
``` and

```
                                         (SEQ ID NO: 3)
5' GGA GAT CTA GAG TTG TCC ACA GTC GGA GAT GGT 3'.
```

The resulting fragment (573 base pairs) was cloned into pCRII and amplified. The CyP sequence was cut out with Sma1 and EcoR1 and cloned into the Sma1/EcoR1 sites in pGEX2TK (Pharmacia). This plasmid was transformed into BL21 *E. coli* cells for expression of the GST-CyPA fusion protein.

EXAMPLE 16

Semiautomated Assay of Rotamase Activity Inhibition

Rotamase inhibition was determined using a semiautomated microtiter plate assay modification of the above described assay [see Küllertz et al., *Clin. Chem.* 44, 502–508 (1998)]. All dilutions of CyPA, peptide substrate, and chymotrypsin were made in 35 mM ice-cold HEPES buffer. Fifty μL of CyPA solution is added to 50 μL of the peptide substrate solution (Phe-Pro-Phe p-nitroanilide, 0.16 mg/ml) in a glass microtiter well plate (the concentration of human recombinant CyP being adjusted so that the reaction rate is increased by a factor of 3 as compared to an uncatalyzed control reaction wherein the peptide substrate is degraded by chymotrypsin alone, in the absence of CyPA and test compound). Using a Beckman Multimek™ 96 automated 96-channel pipettor, 5 μL of test compound solution, or a DMSO blank, were added to each well for a 30 minute preincubation at 4° C. One hundred μL of chymotrypsin solution (1 mg/mL) were added to each well and the absorbance at 390 nm versus time was monitored for 9–10 minutes using a BioRad Ultramark plate reader maintained at 4° C. and the rate constants were determined from the absorbance versus time data files.

$IC_{50}$ values which were obtained for representative compounds are presented in the following Table B. The cyclophilin utilized was a human recombinant CyPA. An asterisk indicates that the compound was evaluated using a recombinant rat CyPA-GST fusion protein (see supra, Example 15). While CyP A was used in these examples, other CyP proteins can be substituted. Similar methods can be used with other immunophilins, such as the FKBPs, to demonstrate the presence or absence of FKBP binding activity.

TABLE B

| Compound # | $IC_{50}$ (nM) |
|---|---|
| 1 | 2,940 |
| 2 | 15,900 |
| 3 | 3,420 |
| 4 | 833 |
| 5 | 1,300 |
| 6 | 3,790 |
| 7 | 2,110 |
| 8 | 4,760 |
| 9 | 1,580 |
| 10 | 933 |
| 11 | 807 |
| 12 | 7,710 |
| 13 | 1,370 |
| 14 | 15,100 |
| 15 | 9,100 |
| 16 | n.d. |
| 17 | 1,980 |
| 18 | 1,320 |
| 19 | 2,800 |
| 20 | 499 |
| 21 | 1,730 |
| 22 | 4,710 |
| 23 | 7,850 |
| 24 | 7,170 |
| 25 | 2,030 |
| 26 | 2,540 |
| 30 | 10,000 |
| 31 | 6,940* |
| 32 | 51.5/91.7* |
| 34 | 9,720* |
| 35 | 353* |
| 39 | 1,120 |
| 40 | 719 |
| 43 | 287* |
| 53 | 392 |

As noted above, a number of methods can be used to assay for the bioactivity of the compounds of the invention. These assays can be in vivo or in vitro methods. The examples below illustrate assays for the ability of the compounds to protect neuronal cells from toxic treatments and the ability of the compounds to elicit neuronal cell growth, regeneration, or neurite extension.

EXAMPLE 17

Immunostaining and Neurite Outgrowth Quantitation in Dorsal Root Gangila Preparations Dorsal root ganglia (DRG) from adult mice can be isolated by micro-dissection. The spinal cord with attached DRGs from an adult mouse (15–20 g) is removed. Spinal nerves are cut away using micro-dissection scissors and any excess material is trimmed until the DRG is free. Using sharp micro-dissecting scissors, a transverse cut is made in the peripheral nerve, leaving 1–2 mm attached, and the explant placed into Petri dish and covered with plating media. When finished collecting all DRGs, the spinal nerve is trimmed to about 1 mm in length. The explant is then embedded in 30 µl of reduced growth factor Matrigel on a circular coverslip, and placed in a 35 mm culture dish. The sensory ganglion explant is then covered with 2 ml of media. Compounds, drugs or control solutions are added from 10×stocks, and incubated at 37° C., 5% $CO_2$, 95% humidity for 48 hrs. Cultures are washed twice with PBS, and fixed with 10% formalin for 30 minutes. Fixed cultures are rinsed twice with PBS and stored in PBS under refrigeration pending staining and analysis.

For staining, cultures are incubated in Block Buffer (5% Horse Serum, 5% Goat Serum, 1% Triton X, PBS pH=7.4) overnight, while rotating, at a temperature of 4° C. A primary antibody against beta tubulin (Sigma Chemical Co.) is diluted in Block Buffer and cultures are incubated overnight at 4° C. Preparations are washed 5 times with PBS and a secondary antibody (Alexa 488 Goat Anti-Mouse), diluted in block buffer, is applied overnight at 4° C. Preparations are washed 5 times with PBS and left overnight at 4° C. Cultures are coverslipped and total neurite length from the end of the attached spinal nerve is measured using commercially available microscopic image analysis software. Lengths of all neurites are quantitated and compared to those present in vehicle-treated control DRGs. Compounds of this invention elicit a significant increase in the number and/or average length of neurites as compared to vehicle-treated control preparations.

EXAMPLE 18

Neuroprotection Assay in Spinal Cord Slice Preparations

All cultures were derived from postnatal day 8 (P8) Sprague-Dawley rat lumbar spinal cord slices of 325 micrometer thickness, prepared using a commercially available McIlwain tissue chopper. Each experiment consisted of two 6-well plates with 5 slices from 4 different animals per well. Media changes were performed every 3 to 4 days. Cultures were treated with THA [L(−)-threo-3-hydroxyaspartic acid; Tocris Cookson Inc., Ballwin, Mo.] at 200 µM+compound (10 µM) after one week in culture. The control was an untreated sample with 0.1% DMSO as vehicle. The THA control was a THA treated sample with 0.1% DSMO as vehicle. Two wells were used per condition. One media change with new THA and compounds was performed. The experiment was stopped 6 to 8 days following drug treatment (13–15 total days in vitro, DIV) as dictated by visual assessment of lesion, by fixation with 4% paraformaldehyde/0.1 M phosphate buffer for 30 minutes.

Slices were permeabilized with 100% cold methanol for 10 minutes, subsequently washed 3×in 0.1M phosphate buffer and transferred to staining wells. The slices were blocked with 10% horse serum/0.05M tris buffered saline. Primary antibody incubation was conducted overnight at 4° C. with anti-neurrofilament H (non-phosphorylated) (SMI-32) antibody 1:5000 in 2% HS/TBS. The Vectastain ABC Elite Kit with rat absorbed anti-mouse secondary antibody was used with diaminobenzidine (DAB) as a chromogen to stain the slices. The slices were mounted onto a slide and coverslips were sealed with DPX mounting solution. Quantification of surviving neurons was performed on a Zeiss Axiovert microscope. Neuronal survival was determined by observing an intact neuronal cell body with processes located ventrally of the central canal in each hemisphere. This correlated to laminae VII, VIII and IX. Each hemisphere was counted individually. The statistics were performed with StatView™ software on a minimum of three different experiments per condition and significance was determined as compared to THA control. The percent of protection was determined from the average number of living neurons by the following equation: (drug treatment condition−THA control)/(Untreated control−THA control). Untreated control cultures displayed an average of 26.4±4.2 (mean±standard error) SMI-32 immunoreactive neurons per ventral hemisphere of the spinal cord slices at the end of the culturing interval, while THA-treated control cultures displayed a significantly reduced number of 18.97±2.04 cells. Addition of Exemplary Compound 43 to THA-treated cultures caused a complete protection from THA-induced cell death (28.14±2.4 cells/ventral hemisphere). Other compounds of this invention are equally expected to elicit a significant increase in the numbers of surviving neurons as compared to control cultures.

EXAMPLE 19

Inhibition of Mitochondrial Permeability Transition in a Spectrophotometric Large Amplitude Mitochondrial Swelling Assay Fresh rat liver mitochondria are prepared from male Sprague-Dawley rats as described by Broekemeier, et al., *J. Biol Chem.* 260:105–113 (1985). Incubations are conducted at room temperature in an assay buffer containing 10 mM sodium succinate, 3 mM Hepes (pH 7.4), 5 µM rotenone, 0.5 µg/ml oligomycin, 10 µM $CaCl_2$, and mannitol/sucrose at a ratio of 3:1 to yield an osmotic strength of 300 mosmoles. Five µl of the isolated mitochondria preparation and 5 µl of compound or vehicle solution are added at various concentrations and optical density (OD) is read at 540 nm for one minute to obtain a baseline reading. Ten µl of ruthenium red solution is added to yield a final concentration of 1 µM, and $OD_{540}$ is monitored for an additional minute. Twenty-five µl of fluoro-carbonyl cyanide solution is added to yield a final concentration of 4 µM, and $OD_{540}$ is monitored for an additional 4–5 minutes. Mitochondrial permeability transition is manifested as a progressive drop in net absorbance as the mitochondria swell. The ability of the compounds of the invention to inhibit mitochondrial permeability transition and swelling can be expressed as $IC_{50}$ values. Compounds of this invention significantly inhibit the progressive drop of net absorbance at $OD_{540}$, and inhibit the mitochondrial permeability transition in a dose-dependent manner.

EXAMPLE 20

In Vivo Protective Effects in an Animal Model of Cerebral Stroke

Male Sprague Dawley rats, weighing 260–290 g, are used in determining the protective effects of the compounds of the invention against ischemia-induced brain damage. The compounds are dissolved in 50 mM Hepes buffered saline or another physiologically acceptable vehicle, and the pH is adjusted to 7.4 before administration. The compound is administered intravenously 60 min following experimental medial cerebral artery occlusion (MCAO) at a bolus dose of, e.g., 100 mg/kg immediately followed by an infusion dose of 20 mg/kg/hr for 4 hours. The intraluminal filament model of transient MCAO is well established in the art [see, e.g., Lu, et al., Eur. J. Pharmacol. 408: 233–239 (2000)]. Briefly, under 1.5% halothane anesthesia, the rat common carotid artery is exposed at the level of external and internal carotid artery bifurcation. The external carotid artery (ECA) and its branches are cauterized and cut. A piece of 3-0 monofilament nylon suture with a blunted tip is introduced into the internal carotid artery (ICA) via the proximal end of the ECA stump. The suture is advanced through the carotid canal to the origin of the MCA where it blocks the blood flow to its entire territory. At the end of the 2 hour occlusion period, the rat is re-anesthetized and the suture is carefully pulled back to the ECA stump to allow reperfusion. During the surgery, the animal's body temperature is maintained at 37.0° C. via a heating blanket. The experimental animals are sacrificed following 22 hr of reperfusion. The brains are removed and cut into seven 2-mm thick coronal slices, stained with 1% 2,3,5-triphenytetrazolium chloride (TTC), and subsequently imaged using a computer-assisted digital imaging analysis system. The ischemic injury is quantified based on the volume of the infarct tissue completely lacking TTC staining. The total infarct volume and the infarct volumes of the cortical and subcortical regions of each rat are used for statistical analysis. A one-factor analysis of variance can be used for comparison of treatment effects. The difference between groups is considered statistically significant at $p<0.05$. Administration of compounds of this invention leads to a significant reduction in infarct volume as compared to vehicle-treated animals.

EXAMPLE 21

In Vivo Protective Effects in an Animal Model of Myocardial Infarction

The surgical procedures and protocol for inducing experimental myocardial infarction is itself well-established in the art [see, e.g., Kukreja, et al., Mol. Cell. Biochem., 195: 123–131 (1999)]. Briefly, male Sprague-Dawley rats (225–300 g) are anaesthetized with 65 mg/kg sodium pentobarbital i.p;. Following tracheotomy, animals are mechanically ventilated using 35% $O_2$/65% $N_2$ at 50 strokes/min. and a stroke volume of 2 ml, and maintained at 37.0° C. using a heating blanket. Electrocardiographic leads are attached to subcutaneous electrodes to monitor either limb leads I, II or III. The right carotid artery is cannulated and connected to a pressure transducer to monitor arterial pressure throughout the experiment, and the right jugular vein is cannulated to allow intravenous administration of compounds of the invention. The compounds are dissolved in 50 mM Hepes buffered saline or another physiologically acceptable vehicle, and the pH is adjusted to 7.4 before administration. The compound is administered intravenously 20 min prior to experimental coronary artery occlusion at a bolus dose of, e.g., 100 mg/kg, immediately followed by an infusion dose of 20 mg/kg/hr for 140 minutes. A left thoracotomy is performed at the fourth intercostal space and the heart exposed. A 5-0 silk suture with a traumatic needle is then passed around the left coronary artery midway between the atrioventricular groove and the apex, and the ends of the suture thread are passed through a piece of vinyl tubing to form a snare. The coronary artery is transiently occluded by tightening and fixing the snare. Myocardial ischemia can be confirmed visually by regional cyanosis of the exposed heart, hypokinetic movement of the heart muscle, or by ST segment elevation/depression or T wave inversion on the electrocardiogram. The snare is released after 30 minutes and reperfusion is visually confirmed by hyperemia over the previously cyanotic area of the heart muscle, and by hemodynamic improvement in blood pressure. Following 90 minutes of reperfusion, the snare is again tightened and approximately 1 ml of Evan's blue dye is injected as a bolus vial the jugular vein catheter. The animals are sacrificed immediately, the hearts are removed, frozen, and cut from apex to base into 6–8 transverse 2 mm-thick slabs. The area at risk is determined by the absence of Evan's blue staining. The slices are then incubated in 1% TTC solution for visualization of viable tissue. The infarct volume and area at risk are quantitated using a commercially available image analysis system. Administration of compounds of this invention leads to a significant dose-dependent reduction in infarct volume as compared to animals treated with vehicle alone.

EXAMPLE 22

In Vivo Reinnervation of the Denervated Striatum by Nigrostriatal Dopaminergic Fibers The MPTP-lesioned mouse model of Parkinson's disease was utilized to demonstrate in vivo efficacy of the compounds of this invention. MPTP (N-methyl-4-phenyl-1,2,3, 6-tetrahydropyridine) is a systemically available neurotoxin specific to nigrostriatal dopaminergic neurons, i.e. to the cells that degenerate in human Parkinson's disease. Administration of MPTP to mice leads to a selective partial destruction of the mesotelencephalic dopaminergic projection, and to a loss of dopamine and dopaminergic fibres in the corpus striatum, which is the main forebrain target of midbrain dopaminergic neurons.

Young adult male CD1 albino mice (Harlan-Sprague Dawley; 22–25 g) were dosed i.p. with the dopamine cell-specific neurotoxin N-methyl-4-phenyl-1,2,3,6-tetrahydropyridine (MPTP hydrochloride, calculated as 34 mg/kg free base), dissolved in saline at a concentration of 3.4 mg/ml free base once daily on days one to five. Experimental compounds were administered once daily on days 1–5 (10 mg/kg in Intralipid vehicle, s.c.), one hour prior to MPTP-administration.

On day seven, animals were perfused transcardially with 10% neutral buffered formalin. Sagittal sections of striatal tissue were cut at 20 μm thickness on a freezing microtome and processed for free-floating tyrosine hydroxylase immunocytochemistry using a polyclonal TH antibody (Pel Freeze, 1:2500 under refrigeration for 4 nights), further processed using the avidin:biotin peroxidase method (Vector Elite kit), and visualized with Diamino benzidine (DAB-HCl, Polysciences).

Blinded analysis of TH fiber density in the central striatum was performed at 630×magnification. For each mouse striatum, five representative 100 μm×100 μm fields in the central striatum were photographed using a digital video camera. The percentage of sample field covered by TH positive processes and terminals was calculated using an image analysis program ("Simple," Compix Inc., Pittsburgh, Pa.). The mean striatal innervation density was calculated for each group. The magnitude of striatal deafferentation due to the MPTP lesion was assessed by dividing the observed striatal innervation values obtained in MPTP/vehicle treated cases by the mean striatal innervation density in the Vehicle/Vehicle group and expressed as %loss. The relative efficacy of the compounds of this invention was expressed as % protection of striatal innervation density, i.e., the degree to which the density of TH positive fibres in the striatum of lesioned/compound-treated animals exceeded the loss observed in lesioned-alone animals.

Experimental animals treated with Exemplary Compound 42 of this invention according to the above protocol displayed a 44.1% protection of striatal tyrosine hydroxylase-immunorecative fibres. Treatment with Exemplary Compound 44 resulted in a 25.1% protection of striatal tyrosine hydroxylase-immunoreactive fibres relative to control animals.

In order to assess the capacity of the compounds of this invention to induce regeneration of MPTP-lesioned nigrostriatal dopaminergic fibers, mice were treated with MPTP once daily on days 1–5, and Exemplary Compound 42 was administered once daily on days 8–12. Mice were perfused on day 18 and brain tissue was processed and analyzed as described above. The density of TH positive fibres in the striatum of lesioned/compound-treated animals exceeded the loss observed in lesioned-only animals by 88%.

Administration of other compounds of this invention is expected to lead to a significant protection of striatal dopaminergic innervation density from neurotoxin-induced lesion.

EXAMPLE 23

In Vivo Hair Generation

Experimental methods useful in assessing the ability of the present compounds to protect from cancer chemotherapy-induced alopecia are themselves established in the art. [See, e.g., Maurer, et al. *Am. J. Pathol.* 150(4):1433–41 (1997)]. In addition, a useful experimental model for assessing the ability of compounds to induce hair growth in bald human scalp from subjects with male pattern baldness has been reported. [Sintov, et al., *Int. J. Pharm.* 194:125–134 (2000)]. Simple procedures for the assessment of hair revitalizing properties of experimental compounds have been disclosed previously by the inventors. See, e.g., U.S. Pat. No. 6,194,440 B1. These and other publications referenced herein can be relied upon to assess the hair growth-promoting and hair loss-retarding properties of compounds of Formula I. The following procedure illustrates:

Mice of the C57B1/6 strain, aged 7–8 weeks, are housed individually. Under light ether anaesthesia, an area of about 2 cm by 2 cm of the lower back/hindquarter region is shaved to remove all existing hair. Care is taken to avoid scrapes, cuts or abrasions of the skin. A pinkish color of the skin confirms that all animals are in the telogen phase of the hair growth cycle. Groups of 10 animals are treated topically with 20% propylene glycol vehicle, or with compounds of the invention at concentrations ranging from 0.1 $\mu$M to 100 $\mu$M per milliliter vehicle. Compounds are topically administered three times per week, and hair growth is assessed weekly by a blinded observer on a scale of 0 (no growth) to 5 (complete hair growth over shaved area). The compounds of the invention induce the growth of hair in a dose-dependent manner, and significantly shorten the time elapsed until the shaved area is covered by hair as compared to the shaved area of vehicle-treated animals.

As noted above, the specific examples recited above should not be interpreted as a limitation to the scope of the invention. Instead, they are merely exemplary embodiments one skilled in the art would understand from the entire disclosure of this invention. The invention being thus described, it will be obvious that the same may be varied in many ways. Such variations are not to be regarded as a departure from the spirit and scope of the invention and all such modifications are included to be within the scope of the following claims.

REFERENCES CITED

Each of the references cited below or in the text above can be relied on to make and use any aspect of this invention. While particular uses and references are discussed above, this should not be taken as a limitation on the use of any particular reference. All the references are specifically included into this text by reference, in their entirety.

Apfel, et al., *Brain Res.* 634: 7–12 (1994);
Ausubel, et al., eds., *Current Protocols in Molecular Biology*, John Wiley & Sons, N.Y., (and supplements through December 2000);
Bell, et al., *Biochem. Pharmacol.* 48:495–503 (1994);
Berriman and Fairlamb, *Biochem. J.* 334:437–445 (1998);
Broekemeier, et al., *J. Biol. Chem.* 264: 7826–7830 (1989);
Coligan, et al., eds., *Current Protocols in Immunology*, John Wiley and Sons, N.Y., (and supplements through December 2000);
Enna, et al., eds., *Current Protocols in Pharmacology*, John Wiley & Sons, N.Y., (and supplements through December 2000);
Fingl, et al., in *The Pharmacological Basis of Therapeutics*, Ch. 1, (1975);
Fischer, et al., *Biomed. Biochem. Acta* 43: 1101–1112 (1984);
Friedman et al., *Proc. Natl. Acad. Sci.*, 90:6815–6819 (1993);
Gash, et al., *Nature* 380: 252–255 (1996);
Gerlach, et al., *Eur. J. Pharmacol.-Mol. Pharmacol.* 208: 273–286 (1991);
Gold, et al., *Exp. Neurol.* 147: 269–278 (1997);
Gold, *Mol. Neurobiol.* 15: 285–306 (1997);
Griffiths and Halestrap, *J. Mol. Cell Cardiol.* 25: 1461–1469 (1993);
Hamilton and Steiner, *J. Med. Chem.* 41: 5119–5143 (1998);
Hamilton, et al., *Bioorgan. Med. Chem. Lett.* 7: 1785–1790 (1997);
Handschumacher, et al., *Science* 226:544 (1984);
Harding, et al., *Nature*, 341:758–760 (1989);
Harrison, et al., *Biochem.* 29: 3813–3816 (1990);
Hoffer, et al., *J. Neural Transm.* [*Suppl.*] 49: 1–10 (1997);
Holt, et al., *Bioorg. Med. Chem. Letters*, 4: 315–320 (1994);
Hsu, et al., *J. Am. Chem. Soc.* 112: 6745–6747 (1990);
Iwabuchi, et al., *J. Dermatol. Sci.* 9: 64–69 (1995);
Jiang, et al., *J. Invest. Dermatol.*, 104 523–525 (1995);
Justice, et al., *Biochem. Biophys. Res. Commun.* 171: 445–450 (1990);
Khattab, et al., *Exp. Parasitol.* 90:103–109 (1998);
Kofron, et al., *Biochem.* 30: 6127–6134 (1991);
Kofron, et al., *J. Am. Chem. Soc.* 114: 2670–2675 (1992);
Kukreja, et al., *Mol. Cell. Biochem.*, 195: 123–131 (1999);
Kütllertz, et al., *Clin. Chem.* 44: 502–508 (1998);
Lang, et al., *Nature* 329: 268–270 (1987);
Leducq, et al., *Biochem. J.* 336: 501–506 (1998);
Lemasters, et al., *Mol. Cell. Biochem.* 174: 159–165 (1997);
Li, et al., *J. Med. Chem.* 43: 1770–9 (2000);
Lu, et al., *Eur. J. Pharmacol.* 408: 233–239 (2000);
Lyons, et al., *Proc. Natl. Acad. Sci. U.S.A.* 91:3191–3195 (1994);
Marchetti, et al., *J. Exp. Med.* 184: 1155–1160 (1996);
Matsumoto, et al., *J. Cereb. Blood Flow Metab.* 19: 736–41 (1999);

Maurer, et al. *Am. J. Pathol.* 150(4):1433–41 (1997);
McLauchlan, et al., *Parasitology* 121:661–70 (2000);
McMahon, et al., *Curr. Opin. Neurobiol.* 5: 616–624 (1995);
Mucke, et al., *Biochem.* 31: 7848–7854 (1992);
Palacios, *J. Immunol.* 128:337 (1982);
Paus, et al., *Am. J. Pathol.* 144: 719–34 (1994);
Perkins, et al., *Antimicrob. Agents Chemother.* 42: 843–848 (1998)
*Remington's Pharmaceutical Sciences,* Mack Publishing Co., Easton, Pa., 18$^{th}$ edition (1990);
Schonbrunner, et al., *J. Biol. Chem.* 266: 3630–3635 (1991);
Sintov, et al., *Int. J. Pharm.* 194:125–134 (2000);
Snyder, *Nat. Med.* 1:32–37 (1995);
Steiner, et al., *Proc. Natl. Acad. Sci. U.S.A.* 94: 2019–2024 (1997);
Streblow, et al., *Virology* 245: 197–202 (1998);
Wang, et al., *J. Pharmacol. Exp. Therap.* 282: 1084–1093 (1997);
Yamamoto, et al., *J. Invest. Dermatol.* 102 (1994) 160–164;
Yoo, et al., *J. Mol. Biol.,* 269: 780–795 (1997);
Zahner and Schultheiss, *J. Helminthol.* 61:282–90 (1987);
Zamzami, et al., *FEBS Lett.* 384: 53–57 (1996).

We claim:
1. A compound of the following Formula I:

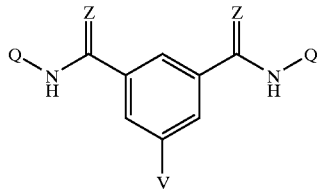

Formula I and pharmaceutically acceptable derivatives thereof;
where V is Q-substituted $C_1$–$C_6$ alkyl, or —$(CH_2)_n$—W; wherein W is Q, or —O—$(CH_2)_m$—Q;
n and m are independently 0–4;
Z is Q or S;
and Q is a mono-, bi-, or tricyclic, carbocyclic ring which is saturated, partially saturated, or aromatic, and wherein the individual ring sizes are 5–6 members, and wherein Q is optionally substituted in one or several positions with:
halo; hydroxyl; mercaptyl; nitro; trifluoromethyl; aminocarbonyl; arylaminocarbonyl in which the aryl is optionally halogenated and optionally substituted with trifluoromethyl or cyano; $C_1$–$C_4$ alkylsulfonyl; $C_1$–$C_4$ alklylthio; oxo; cyano; $C_1$–$C_6$ alkyl or alkenyl; $C_1$–$C_5$ alkoxycarbonyl; $C_1$–$C_4$ alkenyloxy; phenoxy; phenyl; cyanophenyl; benzyloxy; benzyl; amino; $C_1$–$C_4$ alkylamino; di-($C_1$–$C_4$) alkylamino; $C_1$–$C_4$ alkylcarbamoyl; di($C_1$–$C_4$)alkylcarbamoyl; or a combination thereof.

2. The compound of claim 1, wherein V is —$(CH_2)_n$—W; and W is —O—$(CH_2)_m$—Q.

3. A pharmaceutical composition, comprising:
(i.) a compound of Formula I as defined in claim 1, and
(ii.) a pharmaceutically acceptable carrier, diluent, or excipient.

4. A compound of the following formula

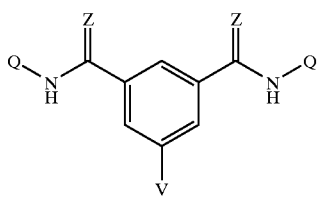

and pharmaceutically acceptable derivatives thereof;
where V is —$CH_2$—O—Q;
Z is O or S;
and Q is a mono-, bi-, or tricyclic, carbocyclic ring which is saturated, partially saturated, or aromatic, and wherein the individual ring sizes are 5–6 members, and wherein Q is optionally substituted in one or several positions with:
halo; hydroxyl; mercaptyl; nitro; trifluoromethyl; aminocarbonyl; arylaminocarbonyl in which the aryl is optionally halogenated and optionally substituted with trifluoromethyl or cyano; $C_1$–$C_4$ alkylsulfonyl; $C_1$–$C_4$ alkylthio; oxo; cyano; carboxy; $C_1$–$C_6$ alkyl or alkenyl; $C_1$–$C_4$ alkoxy; $C_1$–$C_5$ alkoxycarbonyl; $C_1$–$C_4$ alkenyloxy; phenoxy; phenyl; cyanophenyl; benzyloxy; benzyl; amino; $C_1$–$C_4$ alkylamino; di-($C_1$–$C_4$) alkylamino; $C_1$–$C_4$ alkylcarbamoyl; di($C_1$–$C_4$)alkylcarbamoyl; or a combination thereof.

5. A compound of the following formula

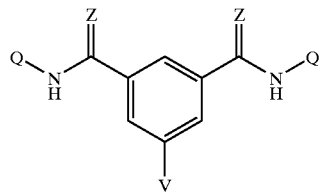

and pharmaceutically acceptable derivatives thereof;
where V is —O—$CH_2$—Q;
and wherein Z and Q are as defined in claim 4, above.

6. A compound of the following formula

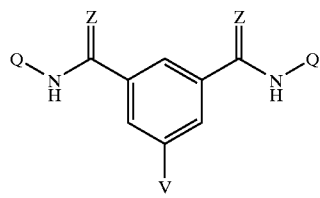

and pharmaceutically acceptable derivatives thereof;
wherein V is Q-substituted $C_1$–$C_6$ straight or branched chain alkyl;
and wherein Z and Q are as defined in claim 4, above.

7. A compound selected from:
5-Naphthalen-1-yl-N,N'-bis-(3-trifluoromethyl-phenyl) isophthalamide;
(5-(2-naphthyloxy)-3-{N-[3-(trifluoromethyl)phenyl] carbamoyl}phenyl)-N-[3-(trifluoromethyl)phenyl] formamide;
(5-(2-naphthyl)-3-{N-[3-(trifluoromethyl)phenyl] carbamoyl}phenyl)-N-[3-(trifluoromethyl)phenyl] formamide;
1-[(3,4-dichlorophenyl)oxymethyl]-3,5-bis-[(3,5-dichlorophenyl) aminocarbonyl]benzene;
1-[4-(2-cyanophenyl)benzy]loxy-3,5-bis-[(3-cyanophenyl) aminocarbonyl]benzene;
(5-(2-(2-5,6,7,8-tetrahydronaphthyl)ethyl)-3-{N-[3-(trifluoromethyl) phenyl]carbamoyl}phenyl)-N-[3-(trifluoromethyl)phenyl]formamide;
(5-(2-(2-naphthyl)ethyl)-3-{N-[3-(trifluoromethyl) phenyl]carbamoyl}phenyl)-N-[3-(trifluoromethyl) phenyl]formamide;
1-(3,4-dichlorobenzyloxy)-3,5-bis-[(3,4,5-trichlorophenyl) aminocarbonyl]benzene;
3-{[(3-Trifluoromethyl-4-chlorophenyl)aminocarbonyl] benzyloxy}-1,5-bis-[(3-trifluoromethyl-4-chlorophenyl)aminocarbonyl]benzene;
3-{[(3,4-dichlorophenyl)aminocarbonyl]benzyloxy}-1,5-bis-[(3,4-dichloro-phenyl)aminocarbonyl]benzene;
1,3-Bis[(3-trifluoromethylphenyl)aminocarbonyl]-5-[(2-naphthyl) methyloxy]benzene; and
1,3-Bis-[3,4-dichlorophenyl)aminocarbonyl]-5-(benzyloxy)benzene.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Artificial substrate for measuring cyclophilin
      rotamase activity
<220> FEATURE:
<221> NAME/KEY: MISC_FEATURE
<222> LOCATION: (1)..(1)
<223> OTHER INFORMATION: Xaa at position 1 is N-succinyl-Ala
<220> FEATURE:
<221> NAME/KEY: MISC_FEATURE
<222> LOCATION: (5)..(5)
<223> OTHER INFORMATION: Xaa at position 5 is p-nitroanilide

<400> SEQUENCE: 1

Xaa Ala Pro Phe Xaa
1               5

<210> SEQ ID NO 2
<211> LENGTH: 33
<212> TYPE: DNA
<213> ORGANISM: Artificial Sequence
<220> FEATURE:
<223> OTHER INFORMATION: PCR primer

<400> SEQUENCE: 2 cccccggga gtcaacccca ccgtgttctt cga                              33

<210> SEQ ID NO 3
<211> LENGTH: 33
<212> TYPE: DNA
<213> ORGANISM: Artificial Sequence
<220> FEATURE:
<223> OTHER INFORMATION: PCR primer

<400> SEQUENCE: 3
ggagatctag agttgtccac agtcggagat ggt                             33
```